(12) United States Patent
Glenn, Jr. et al.

(10) Patent No.: US 9,074,305 B2
(45) Date of Patent: *Jul. 7, 2015

(54) METHOD FOR DELIVERING AN ACTIVE AGENT

(75) Inventors: Robert Wayne Glenn, Jr., Liberty Township, OH (US); Gregory Charles Gordon, Loveland, OH (US); Mark Robert Sivik, Mason, OH (US); Mark Ryan Richards, Hamilton, OH (US); Stephen Wayne Heinzman, Cincinnati, OH (US); Michael David James, Cincinnati, OH (US); Geoffrey William Reynolds, Montgomery, OH (US); Paul Dennis Trokhan, Hamilton, OH (US); Alyssandrea Hope Hamad-Ebraminpour, Cincinnati, OH (US); Frank William Denome, Cincinnati, OH (US); Stephen Joseph Hodson, Franklin, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/229,838

(22) Filed: Sep. 12, 2011

(65) Prior Publication Data
US 2012/0053108 A1  Mar. 1, 2012

Related U.S. Application Data

(63) Continuation of application No. PCT/US2011/042667, filed on Jun. 30, 2011.

(60) Provisional application No. 61/361,159, filed on Jul. 2, 2010.

(51) Int. Cl.
*C11D 17/04* (2006.01)
*D06L 1/00* (2006.01)
(Continued)

(52) U.S. Cl.
CPC ...... *D01F 1/10* (2013.01); *B08B 9/20* (2013.01); *D06L 1/00* (2013.01); *A61L 27/50* (2013.01); *A61L 27/54* (2013.01);
(Continued)

(58) Field of Classification Search
USPC .............. 510/296, 283, 439, 519, 220, 108; 8/137; 134/25.2, 42
See application file for complete search history.

(56) References Cited

U.S. PATENT DOCUMENTS 3,293,718 A  12/1966 Thomas
3,859,125 A  1/1975 Miller et al.
(Continued)

FOREIGN PATENT DOCUMENTS

AU  2004/202461 B2  11/2007
CA  2695068 A1  9/2010
(Continued)

OTHER PUBLICATIONS

Wang, et al., "A Novel Controlled Release Drug Delivery System for Multiple Drugs Based on Electrospun Nanofibers Containing Nanoparticles", *Journal of Pharmaceutical Sciences*, vol. 99, No. 12 (Dec. 2010).
(Continued)

*Primary Examiner* — Lorna M Douyon
(74) *Attorney, Agent, or Firm* — C. Brant Cook

(57) ABSTRACT

A method for delivering an active agent is provided.

22 Claims, 3 Drawing Sheets

(51) Int. Cl.
  *B08B 9/20* (2006.01)
  *D01F 1/10* (2006.01)
  *A61L 27/50* (2006.01)
  *A61L 27/54* (2006.01)

(52) U.S. Cl.
  CPC ........ *A61L 2300/602* (2013.01); *C11D 17/042* (2013.01); *C11D 17/047* (2013.01)

(56) References Cited

U.S. PATENT DOCUMENTS

| | | |
|---|---|---|
| 3,904,543 A | 9/1975 | Knighten |
| 4,180,558 A | 12/1979 | Goldberg et al. |
| 4,286,016 A * | 8/1981 | Dimond et al. ................. 206/0.5 |
| 4,287,219 A | 9/1981 | Fabre |
| 4,349,531 A | 9/1982 | Mlodozeniec et al. |
| 4,377,615 A * | 3/1983 | Suzuki et al. .................. 428/213 |
| 4,415,617 A | 11/1983 | D'Elia |
| 4,639,390 A | 1/1987 | Shoji |
| 4,892,758 A | 1/1990 | Serbiak et al. |
| 4,923,660 A | 5/1990 | Willenberg et al. |
| 5,041,252 A | 8/1991 | Fujii et al. |
| 5,110,678 A | 5/1992 | Narukawa et al. |
| 5,120,888 A | 6/1992 | Nohr et al. |
| 5,135,804 A | 8/1992 | Harpell et al. |
| 5,158,810 A | 10/1992 | Oishi et al. |
| 5,208,104 A | 5/1993 | Ueda et al. |
| 5,230,853 A | 7/1993 | Colegrove et al. |
| 5,342,335 A | 8/1994 | Rhim |
| 5,362,532 A | 11/1994 | Famili et al. |
| 5,364,627 A | 11/1994 | Song |
| 5,387,147 A | 2/1995 | Ohshima et al. |
| 5,429,874 A | 7/1995 | Vanputte |
| 5,455,114 A | 10/1995 | Ohmory et al. |
| 5,470,653 A | 11/1995 | Honeycutt et al. |
| 5,486,418 A | 1/1996 | Ohmory et al. |
| 5,518,730 A | 5/1996 | Fuisz |
| 5,520,924 A | 5/1996 | Chapman et al. |
| 5,538,735 A | 7/1996 | Ahn |
| 5,585,059 A | 12/1996 | Kobayashi et al. |
| 5,651,987 A | 7/1997 | Fuisz |
| 5,691,015 A | 11/1997 | Tsukamoto et al. |
| 5,705,183 A | 1/1998 | Phillips et al. |
| 5,716,692 A | 2/1998 | Warner et al. |
| 5,717,026 A | 2/1998 | Ikimine et al. |
| 5,735,812 A | 4/1998 | Hardy |
| 5,780,418 A | 7/1998 | Niinaka et al. |
| 5,827,586 A | 10/1998 | Yamashita et al. |
| 5,840,423 A | 11/1998 | Sano et al. |
| 5,863,887 A | 1/1999 | Gillette |
| 5,879,493 A | 3/1999 | Johnson et al. |
| 5,911,224 A | 6/1999 | Berger |
| 5,914,124 A | 6/1999 | Mahoney et al. |
| 5,942,179 A | 8/1999 | Tallentire et al. |
| 6,037,319 A | 3/2000 | Dickler et al. |
| 6,066,396 A | 5/2000 | Inada et al. |
| 6,080,346 A | 6/2000 | Jack |
| 6,130,193 A | 10/2000 | Gillette |
| 6,175,054 B1 | 1/2001 | Jacques |
| 6,197,238 B1 | 3/2001 | Wang et al. |
| 6,207,274 B1 | 3/2001 | Ferenc et al. |
| 6,274,162 B1 | 8/2001 | Steffenino et al. |
| 6,319,510 B1 | 11/2001 | Yates |
| 6,406,797 B1 | 6/2002 | Vanputte |
| 6,417,156 B1 * | 7/2002 | Smith et al. ................... 510/515 |
| 6,420,625 B1 | 7/2002 | Jones et al. |
| 6,448,462 B2 | 9/2002 | Groitzsch et al. |
| 6,465,407 B2 | 10/2002 | Hayashi et al. |
| 6,552,123 B1 | 4/2003 | Katayama et al. |
| 6,576,575 B2 | 6/2003 | Griesbach, III et al. |
| 6,608,121 B2 | 8/2003 | Isozaki et al. |
| 6,657,004 B2 | 12/2003 | Mizutani |
| 6,699,826 B1 | 3/2004 | Saijo et al. |
| 6,730,648 B2 | 5/2004 | Gorlin et al. |
| 6,783,852 B2 | 8/2004 | Inada et al. |
| 6,787,512 B1 | 9/2004 | Verrall et al. |
| 6,808,598 B1 | 10/2004 | Takeuchi et al. |
| 6,818,606 B1 | 11/2004 | Hanada et al. |
| 6,898,921 B2 | 5/2005 | Duffield |
| 6,949,498 B2 | 9/2005 | Murphy et al. |
| 6,956,070 B2 | 10/2005 | Fujiwara et al. |
| 6,977,116 B2 | 12/2005 | Cabell et al. |
| 7,026,049 B2 | 4/2006 | Endo et al. |
| 7,067,575 B2 | 6/2006 | Kitamura et al. |
| 7,083,047 B2 | 8/2006 | Bone et al. |
| 7,094,744 B1 | 8/2006 | Kobayashi et al. |
| 7,115,551 B2 * | 10/2006 | Hasenoehrl et al. ........... 510/438 |
| 7,169,740 B2 | 1/2007 | Sommerville-Roberts et al. |
| 7,196,026 B2 | 3/2007 | Di Luccio et al. |
| RE39,557 E | 4/2007 | Moe |
| 7,226,899 B2 * | 6/2007 | Cole et al. ..................... 510/296 |
| 7,285,520 B2 | 10/2007 | Krzysik et al. |
| 7,387,787 B2 | 6/2008 | Fox |
| 7,407,669 B2 | 8/2008 | Leung et al. |
| 7,429,273 B2 | 9/2008 | DeDominicis et al. |
| 7,446,084 B2 | 11/2008 | Barthel et al. |
| 7,491,407 B2 | 2/2009 | Pourdeyhimi et al. |
| 7,507,698 B2 * | 3/2009 | Franzolin et al. ............. 510/295 |
| 7,547,737 B2 | 6/2009 | Kochvar et al. |
| 7,563,757 B2 | 7/2009 | Kouvroukoglou et al. |
| 7,708,840 B2 | 5/2010 | Wiedemann et al. |
| 7,727,946 B2 | 6/2010 | Catalfamo et al. |
| 7,824,588 B2 | 11/2010 | Yang et al. |
| 7,856,989 B2 | 12/2010 | Karles et al. |
| 7,967,801 B2 | 6/2011 | Hammons et al. |
| 8,349,232 B2 | 1/2013 | Pourdeyhimi et al. |
| 2001/0037851 A1 | 11/2001 | Mortellite et al. |
| 2002/0018906 A1 | 2/2002 | Clark |
| 2002/0098994 A1 | 7/2002 | Zafar |
| 2002/0161088 A1 | 10/2002 | Kochvar et al. |
| 2002/0173213 A1 | 11/2002 | Chu et al. |
| 2003/0017208 A1 | 1/2003 | Ignatious et al. |
| 2003/0045446 A1 | 3/2003 | Dihora et al. |
| 2003/0166495 A1 | 9/2003 | Wang et al. |
| 2003/0185872 A1 | 10/2003 | Kochinke |
| 2003/0216098 A1 | 11/2003 | Carlyle et al. |
| 2003/0224959 A1 | 12/2003 | Smith |
| 2004/0167256 A1 | 8/2004 | Verrall et al. |
| 2004/0170836 A1 | 9/2004 | Bond et al. |
| 2004/0180597 A1 | 9/2004 | Kamada et al. |
| 2004/0204543 A1 | 10/2004 | Yang |
| 2005/0003048 A1 | 1/2005 | Pearce et al. |
| 2005/0003991 A1 | 1/2005 | MacQuarrie |
| 2005/0008776 A1 | 1/2005 | Chhabra et al. |
| 2005/0010010 A1 | 1/2005 | Kitamura et al. |
| 2005/0136112 A1 | 6/2005 | Gonzales et al. |
| 2005/0136780 A1 | 6/2005 | Clark et al. |
| 2005/0186256 A1 | 8/2005 | Dihel et al. |
| 2005/0281757 A1 | 12/2005 | Ibrahim et al. |
| 2006/0035042 A1 | 2/2006 | Morken |
| 2006/0083784 A1 | 4/2006 | Ignatious et al. |
| 2006/0127458 A1 | 6/2006 | Kiser et al. |
| 2006/0160453 A1 | 7/2006 | Suh |
| 2006/0189772 A1 | 8/2006 | Scheibel et al. |
| 2006/0254013 A1 | 11/2006 | Konishi et al. |
| 2006/0254014 A1 | 11/2006 | Konishi et al. |
| 2006/0258251 A1 | 11/2006 | Konishi et al. |
| 2006/0264130 A1 | 11/2006 | Karles et al. |
| 2007/0054579 A1 | 3/2007 | Baker et al. |
| 2007/0110792 A9 | 5/2007 | Simon |
| 2007/0128256 A1 | 6/2007 | Aubrun-Sonneville |
| 2007/0134304 A1 | 6/2007 | Aubrun-Sonneville et al. |
| 2007/0134481 A1 | 6/2007 | Aubrun-Sonneville |
| 2007/0253926 A1 | 11/2007 | Tadrowski et al. |
| 2007/0259170 A1 | 11/2007 | Brown et al. |
| 2007/0259996 A1 | 11/2007 | Vicari et al. |
| 2007/0298064 A1 * | 12/2007 | Koslow .......................... 424/409 |
| 2008/0035174 A1 | 2/2008 | Aubrun-Sonneville et al. |
| 2008/0095828 A1 * | 4/2008 | Privitera et al. ............... 424/443 |
| 2008/0108748 A1 | 5/2008 | Buckley et al. |
| 2008/0118727 A1 | 5/2008 | Andersen |
| 2008/0146481 A1 | 6/2008 | Brown et al. |
| 2008/0149119 A1 | 6/2008 | Marquez et al. |
| 2008/0220054 A1 | 9/2008 | Shastri et al. |

(56) References Cited

U.S. PATENT DOCUMENTS

| | | |
|---|---|---|
| 2008/0226919 A1 | 9/2008 | Hosoda et al. |
| 2008/0242572 A1 | 10/2008 | Icht et al. |
| 2008/0269095 A1 | 10/2008 | Aubrun-Sonneville |
| 2009/0004254 A1 | 1/2009 | Maibach |
| 2009/0041820 A1* | 2/2009 | Wu et al. ............... 424/409 |
| 2009/0061496 A1 | 3/2009 | Kuhn et al. |
| 2009/0061719 A1 | 3/2009 | Shibutani et al. |
| 2009/0155326 A1 | 6/2009 | Mack et al. |
| 2009/0181587 A1 | 7/2009 | Kang et al. |
| 2009/0249558 A1 | 10/2009 | Fileccia et al. |
| 2009/0285718 A1 | 11/2009 | Privitera et al. |
| 2009/0291282 A1 | 11/2009 | Kitamura et al. |
| 2010/0018641 A1 | 1/2010 | Branham et al. |
| 2010/0021517 A1 | 1/2010 | Ahlers et al. |
| 2010/0105821 A1 | 4/2010 | Verrall et al. |
| 2010/0166854 A1 | 7/2010 | Michniak-Kohn et al. |
| 2010/0196440 A1 | 8/2010 | Stark et al. |
| 2010/0266668 A1 | 10/2010 | Coffee et al. |
| 2010/0279905 A1 | 11/2010 | Glenn, Jr. et al. |
| 2010/0285101 A1 | 11/2010 | Moore et al. |
| 2011/0136719 A1 | 6/2011 | Jalbert et al. |
| 2011/0159267 A1 | 6/2011 | Lee et al. |
| 2011/0223381 A1 | 9/2011 | Sauter et al. |
| 2011/0230112 A1 | 9/2011 | Rosé et al. |
| 2011/0301070 A1 | 12/2011 | Ochomogo et al. |
| 2012/0021026 A1 | 1/2012 | Chhabra et al. |
| 2012/0027838 A1 | 2/2012 | Gordon et al. |
| 2012/0048769 A1 | 3/2012 | Sivik et al. |
| 2012/0052036 A1 | 3/2012 | Glen, Jr. et al. |
| 2012/0053103 A1 | 3/2012 | Sivik et al. |
| 2012/0053108 A1 | 3/2012 | Glen, Jr. et al. |
| 2012/0058166 A1 | 3/2012 | Glen, Jr. et al. |
| 2012/0082037 A1 | 3/2012 | Sivik et al. |
| 2012/0172831 A1 | 7/2012 | Darcy et al. |
| 2012/0215148 A1 | 8/2012 | Ewert et al. |

FOREIGN PATENT DOCUMENTS

| | | |
|---|---|---|
| DE | 10 2007 011606 A1 | 9/2008 |
| EP | 1 275 368 A1 | 1/2003 |
| EP | 1 306 425 A2 | 5/2003 |
| EP | 1 409 628 B1 | 2/2006 |
| EP | 1 512 701 B1 | 6/2006 |
| EP | 1 887 036 A2 | 2/2008 |
| EP | 1 436 376 B1 | 4/2010 |
| EP | 2 226 379 A1 | 9/2010 |
| EP | 1 948 771 B1 | 12/2010 |
| EP | 2 319 965 A1 | 5/2011 |
| EP | 2 363 432 A1 | 9/2011 |
| EP | 2 363 517 A1 | 9/2011 |
| EP | 2 395 142 A1 | 12/2011 |
| GB | 2107579 A | 5/1993 |
| GB | 2375542 | 11/2002 |
| GB | 2449418 | 11/2008 |
| HU | 221299 B1 | 9/2002 |
| JP | 62-156348 | 7/1987 |
| JP | 3040879 A | 2/1991 |
| JP | 3101618 A | 4/1991 |
| JP | 09279457 | 10/1997 |
| JP | 10008364 | 1/1998 |
| JP | 10158700 A | 6/1998 |
| JP | 2000169896 A | 6/2000 |
| JP | 2009079329 | 4/2009 |
| WO | WO 92/06603 A1 | 4/1992 |
| WO | WO 94/02377 A1 | 2/1994 |
| WO | WO 94/04656 A2 | 3/1994 |
| WO | WO 95/23888 A1 | 9/1995 |
| WO | WO 99/57155 | 11/1999 |
| WO | WO 00/13680 A2 | 3/2000 |
| WO | WO 01/25322 A1 | 4/2001 |
| WO | WO 01/54667 A1 | 8/2001 |
| WO | WO 03/060007 A1 | 7/2003 |
| WO | WO 2004/009335 A1 | 1/2004 |
| WO | WO 2004/081162 A1 | 9/2004 |
| WO | WO 2005/068604 A1 | 7/2005 |
| WO | WO 2006/106514 A2 | 10/2006 |
| WO | WO 2007/089259 A1 | 8/2007 |
| WO | WO 2007/093558 A3 | 1/2008 |
| WO | WO 2009/022761 A1 | 2/2009 |
| WO | WO 2007/014221 A3 | 4/2009 |
| WO | WO 2009/103576 A1 | 8/2009 |
| WO | WO 2009/121900 A1 | 10/2009 |
| WO | WO 2010/015709 A2 | 2/2010 |

OTHER PUBLICATIONS

All Office Actions in U.S. Appl. Nos. 13/229,791, 13/229,812, 13/229,818, 13/229,825, 13/229,833, 13/229,838, 13/229,845, 13/229,852.

International Search Report mailed Dec. 16, 2011, PCT/US2011/042667.

All Office Actions in U.S. Appl. No. 13/229,791, U.S. Appl. No. 13/229,812, U.S. Appl. No. 13/229,818, U.S. Appl. No. 13/229,825, U.S. Appl. No. 13/229,833, U.S. Appl. No. 13/229,845, U.S. Appl. No. 13/229,852.

U.S. Appl. No. 13/229,812, filed Sep. 12, 2011, Gordon, et al.

Smith, et al., "Nanofibrous Scaffolds and Their Biological Effects", *Nanotechnologies for the Life Sciences*, vol. 9, pp. 188-215 (2006).

* cited by examiner

METHOD FOR DELIVERING AN ACTIVE AGENT

CROSS REFERENCE TO RELATED APPLICATION

This application is a continuation application of prior copending International Application No. PCT/US2011/042667, filed Jun. 30, 2011, designating the U.S., which claims the benefit of U.S. Provisional Application No. 61/361,159, filed Jul. 2, 2010.

FIELD OF THE INVENTION

The present invention relates to a method for delivering an active agent, in particular a method for delivering an active agent from a filament and/or a fiber, a nonwoven web made from filaments and/or fibers, a film made from filaments and/or fibers, and/or a film made from a nonwoven web.

BACKGROUND OF THE INVENTION

Filaments and/or fibers comprising a filament-forming material and an additive, such as a surfactant, a perfume, a filler, and/or other ingredient, are known in the art. For example, nonwoven fabrics comprising fibers made from an aqueous solution comprising 5-95 wt % pullulan and 50 wt % or less based on the pullulan of a perfume (an active agent) that slowly releases ("blooms") from the fiber while the fiber's morphology does not change during use are known in the art and are used as sanitary products. The aqueous solution used to make the pullulan fibers further comprises 15 wt % or less based on the pullulan of a surfactant that functions as a processing aid, which does not release from the fiber until the fiber undergoes natural decomposition after its use.

Fibers comprising polyvinyl alcohol and/or a polysaccharide and significantly less than 5% by weight of active agents, wherein the active agents release from the fibers while the fibers maintain their fiber properties during use are also known.

A cigarette filter made from electrospun fibers comprising a polysaccharide and 10% or less by weight of an active agent, such as a flavorant, that releases from the fibers as the fibers dissolve after being contacted with moist air is also known in the art.

In addition, fibers made from a non-aqueous solution formed by melting a synthetic wax and adding a primary surfactant and a secondary surfactant to the melted synthetic wax and then cooling the synthetic wax/surfactant mixture such that fibers are formed are known in the art.

Further, fibers and/or filaments that comprise processing aids, such as surfactants, and/or fillers are also known. Such processing aids and/or fillers are not designed to be released from the fibers and/or filaments when the fibers and/or filaments are exposed to conditions of intended use. Further, the total level of the processing aids within the fibers and/or filaments is significantly less than 35% by weight on a dry filament basis and the total level of fillers present in the fibers and/or filaments is typically less than 45% by weight on a dry filament basis.

From the known examples described above, it is clear that the previously existing knowledge suggested that the total level of filament-forming materials needed to exceed the total level of additives, especially active agents, in order for the filament to exhibit a filament structure.

As is evident from the above discussion, known fibers and/or filaments contain less than 50% by weight on a dry fiber/filament basis of active agents that may released from the fibers and/or filaments when exposed to conditions of intended use.

In addition to the known fibers and/or filaments, there are known foams that comprise a foam-forming polymer, such as polyvinylalcohol, and an active agent, such as a surfactant. Such foams do not contain filaments and/or fibers and/or are not nonwoven substrates containing such filaments and/or fibers.

Lastly, as shown in prior art FIGS. 1 and 2, there are known nonwoven substrates 10 that are made of dissolvable fibers 12 wherein the nonwoven substrates 10 are coated and/or impregnated with an additive 14, such as a skin care benefit agent, rather than the additive 14 being present in the dissolvable fibers 12.

As can be seen from the state of the art, there exists a need for a filament and/or fiber that comprises one or more filament-forming materials and one or more active agents that are releasable from the filament, such as when exposed to conditions of intended use and/or when the filament's morphology changes, wherein the total level of the one or more filament-forming materials present in the filament is 50% or less by weight on a dry filament basis and the total level of the one or more active agents present in the filament is 50% or greater by weight on a dry filament basis. Such a filament would be suitable for carrying and/or delivering the active agents in various applications. Further, there is a desire to produce a filament that has a greater level of additive, for example an active agent, than the filament-forming material, for example a polymer in order to optimize the delivery of the active agent with minimal cost and a relatively faster rate of delivery compared to filaments that have a greater level of filament-forming material than active agent.

It is also desirable to incorporate active agents into filaments that otherwise are incompatible with carrier substrates. The present invention also allows normally incompatible active agents to be incorporated into the filament, either into the same filament and/or into different filaments within a nonwoven web comprising the different filaments.

Accordingly, there exists a need for a method for delivering active agents and for novel filaments that comprise a filament-forming material and an active agent that is releasable from the filament and/or fiber and/or from a nonwoven web made from filaments and/or fibers, and/or a film made from filaments and/or a nonwoven web.

SUMMARY OF THE INVENTION

The present invention fulfills the need described above by providing a method for delivering an active agent.

In one example of the present invention, a method for delivering one or more active agents, the method comprising the steps of:

a. providing a nonwoven web comprising a plurality of filaments, wherein at least one of the filaments comprises one or more filament-forming materials and one or more active agents that are releasable from the filament when the filament is exposed to conditions of intended use, wherein the total level of the one or more filament-forming materials present in the filament is 50% or less by weight on a dry filament basis and the total level of the one or more active agents present in the filament is 50% or greater by weight on a dry filament basis; and b. triggering the release of one or more of the active agents from the filament, is provided.

In another example of the present invention, a method for delivering one or more active agents, the method comprising the steps of:

a. providing a nonwoven web comprising a plurality of filaments, wherein at least one of the filaments comprises one or more filament-forming materials and one or more active agents that are releasable from the filament as the filament's morphology changes, wherein the total level of the one or more filament-forming materials present in the filament is less than 65% by weight on a dry filament basis and the total level of the one or more active agents present in the filament is greater than 35% by weight on a dry filament basis; and b. triggering the release of one or more of the active agents from the filament, is provided.

In another example of the present invention, a method for delivering one or more active agents, the method comprising the steps of:

a. providing a nonwoven web comprising a plurality of filaments, wherein at least one of the filaments comprises one or more filament-forming materials and one or more ingestible active agents that are releasable from the filament upon ingesting by an animal, wherein the total level of the one or more filament-forming materials present in the filament is less than 80% by weight on a dry filament basis and the total level of the one or more active agents present in the filament is greater than 20% by weight on a dry filament basis; and b. triggering the release of one or more of the ingestible active agents from the filament, is provided.

In still another example of the present invention, a method for delivering one or more active agents, the method comprising the steps of:

a. providing a nonwoven web comprising a plurality of filaments, wherein at least one of the filaments comprises one or more filament-forming materials and one or more non-perfume active agents, wherein the total level of the non-perfume active agents present in the filament is greater than 35% by weight on a dry filament basis and wherein the filament releases one or more of the non-perfume active agents when the filament is exposed to conditions of intended use; and b. triggering the release of one or more of the non-perfume active agents from the filament, is provided.

In still another example of the present invention, a method for delivering one or more active agents, the method comprising the steps of:

a. providing a filament and/or fiber comprising one or more filament-forming materials and one or more active agents that are releasable from the filament when the filament is exposed to conditions of intended use, wherein the total level of the one or more filament-forming materials present in the filament is 50% or less by weight on a dry filament basis and the total level of the one or more active agents present in the filament is 50% or greater by weight on a dry filament basis; and b. triggering the release of one or more of the active agents from the filament and/or fiber, is provided.

In still another example of the present invention, a method for delivering one or more active agents, the method comprising the steps of:

a. providing a filament and/or fiber comprising one or more filament-forming materials and one or more active agents that are releasable from the filament as the filament's morphology changes, wherein the total level of the one or more filament-forming materials present in the filament is less than 65% by weight on a dry filament basis and the total level of the one or more active agents present in the filament is greater than 35% by weight on a dry filament basis; and b. triggering the release of one or more of the active agents from the filament and/or fiber, is provided.

In still another example of the present invention, a method for delivering one or more active agents, the method comprising the steps of:

a. providing a filament and/or fiber comprising one or more filament-forming materials and one or more ingestible active agents that are releasable from the filament upon ingesting by an animal, wherein the total level of the one or more filament-forming materials present in the filament is less than 80% by weight on a dry filament basis and the total level of the one or more active agents present in the filament is greater than 20% by weight on a dry filament basis; and b. triggering the release of one or more of the ingestible active agents from the filament and/or fiber, is provided.

In even still another example of the present invention, a method for delivering one or more active agents, the method comprising the steps of:

a. providing a filament and/or fiber comprising one or more filament-forming materials and one or more non-perfume active agents, wherein the total level of the non-perfume active agents present in the filament is greater than 35% by weight on a dry filament basis and wherein the filament releases one or more of the non-perfume active agents when the filament is exposed to conditions of intended use; and b. triggering the release of one or more of the non-perfume active agents from the filament and/or fiber, is provided.

In yet another example of the present invention, the filaments and/or fibers and/or nonwoven web of the present invention may be converted into a film and one or more of the active agents may be delivered from the film rather than the filaments and/or fibers and/or nonwoven web upon triggering the release of one or more of the active agents from the film.

Accordingly, the present invention provides a method for delivering an active agent.

DETAILED DESCRIPTION OF THE INVENTION

Definitions

"Filament" as used herein means an elongate particulate having a length greatly exceeding its diameter, i.e. a length to diameter ratio of at least about 10.

The filaments of the present invention may be spun from filament-forming compositions via suitable spinning processes operations, such as meltblowing and/or spunbonding.

The filaments of the present invention may be monocomponent and/or multicomponent. For example, the filaments may comprise bicomponent filaments. The bicomponent filaments may be in any form, such as side-by-side, core and sheath, islands-in-the-sea and the like.

The filaments of the present invention exhibit a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers (which are less than 5.08 cm in length). Non-limiting examples of filaments include meltblown and/or spunbond filaments.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more filament-forming materials and one or more additives, such as active agents. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" as used herein means a composition that is suitable for making a filament of the present invention such as by meltblowing and/or spunbonding. The filament-forming composition comprises one or more filament-forming materials that exhibit properties that make them suitable for spinning into a filament. In one example, the filament-forming material comprises a polymer. In addition to one or more filament-forming materials, the filament-forming composition may comprise one or more additives, for example one or more active agents. In addition, the filament-forming composition may comprise one or more polar solvents, such as water, into which one or more, for example all, of the filament-forming materials and/or one or more, for example all, of the active agents are dissolved and/or dispersed.

Figure 1:
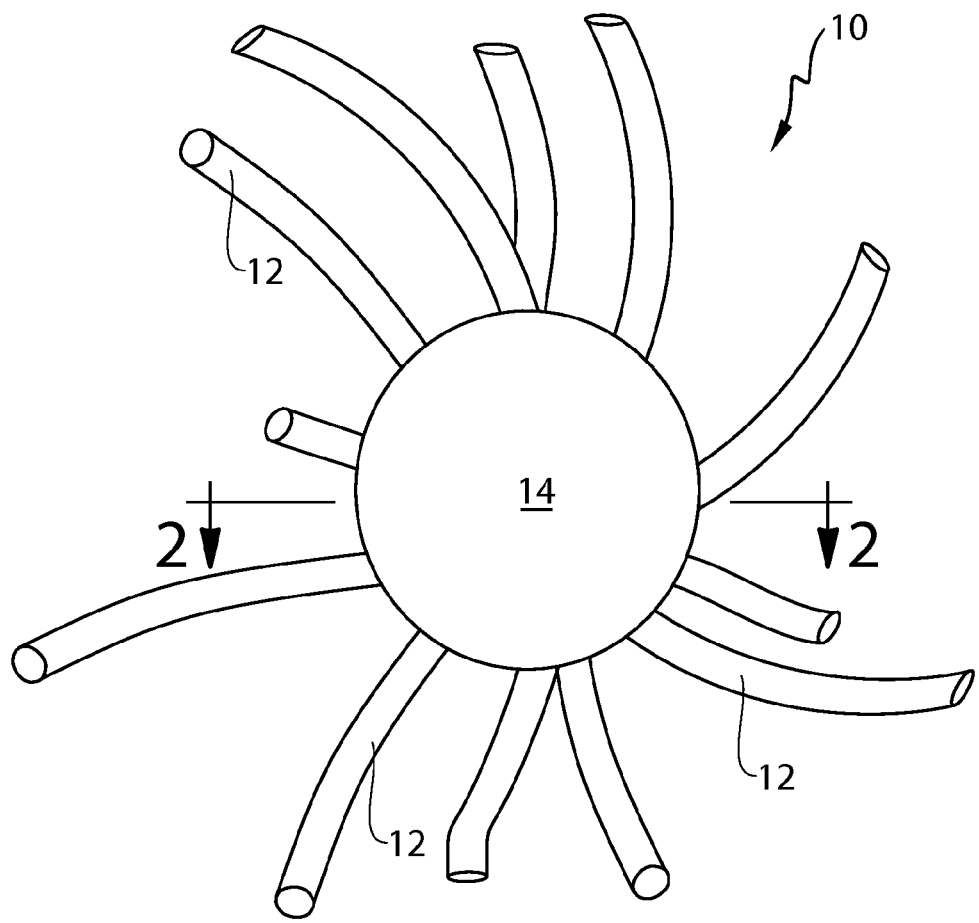
FIG. 1 is a schematic representation of a prior art nonwoven substrate made of dissolvable fibers that is coated with an additive.
Figure 2:
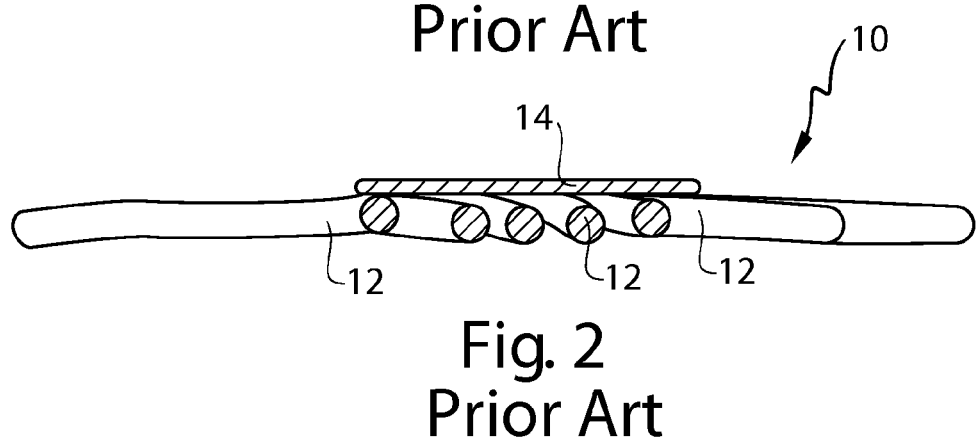
FIG. 2 is a cross-sectional view of FIG. 1 taken along line 2-2 of FIG. 1.
Figure 3:
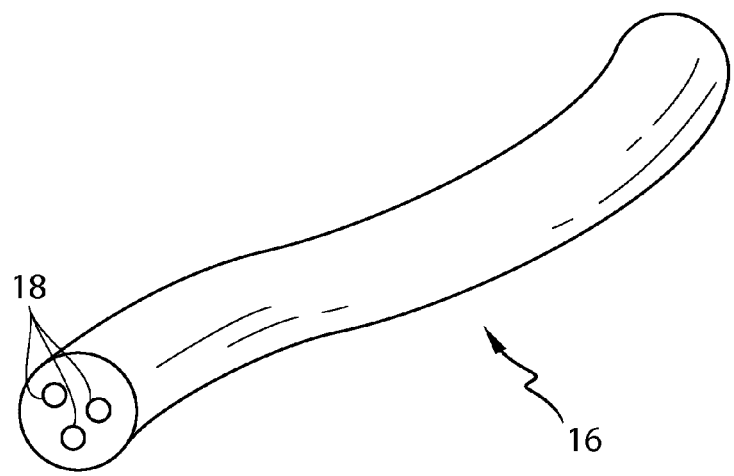
FIG. 3 is a schematic representation of a filament according to the present invention.

In one example as shown in FIG. 3 a filament 16 of the present invention made from a filament-forming composition of the present invention is such that one or more additives 18, for example one or more active agents, may be present in the filament rather than on the filament, such as a coating as shown in prior art FIGS. 1 and 2. The total level of filament-forming materials and total level of active agents present in the filament-forming composition may be any suitable amount so long as the filaments of the present invention are produced therefrom.

In one example, one or more additives, such as active agents, may be present in the filament and one or more additional additives, such as active agents, may be present on a surface of the filament. In another example, a filament of the present invention may comprise one or more additives, such as active agents, that are present in the filament when originally made, but then bloom to a surface of the filament prior to and/or when exposed to conditions of intended use of the filament.

"Filament-forming material" as used herein means a material, such as a polymer or monomers capable of producing a polymer that exhibits properties suitable for making a filament. In one example, the filament-forming material comprises one or more substituted polymers such as an anionic, cationic, zwitterionic, and/or nonionic polymer. In another example, the polymer may comprise a hydroxyl polymer, such as a polyvinyl alcohol ("PVOH") and/or a polysaccharide, such as starch and/or a starch derivative, such as an ethoxylated starch and/or acid-thinned starch. In another example, the polymer may comprise polyethylenes and/or terephthalates. In yet another example, the filament-forming material is a polar solvent-soluble material.

"Additive" as used herein means any material present in the filament of the present invention that is not a filament-forming material. In one example, an additive comprises an active agent. In another example, an additive comprises a processing aid. In still another example, an additive comprises a filler. In one example, an additive comprises any material present in the filament that its absence from the filament would not result in the filament losing its filament structure, in other words, its absence does not result in the filament losing its solid form. In another example, an additive, for example an active agent, comprises a non-polymer material.

In another example, an additive comprises a plasticizer for the filament. Non-limiting examples of suitable plasticizers for the present invention include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexanediol, 2,2,4-trimethylpentane-1,3-diol, polyethylene glycol (200-600), pentaerythritol, sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, high fructose corn syrup solids, and dextrins, and ascorbic acid.

In one example, the plasticizer includes glycerin and/or propylene glycol and/or glycerol derivatives such as propoxylated glycerol. In still another example, the plasticizer is selected from the group consisting of glycerin, ethylene glycol, polyethylene glycol, propylene glycol, glycidol, urea, sorbitol, xylitol, maltitol, sugars, ethylene bisformamide, amino acids, and mixtures thereof.

In another example, an additive comprises a crosslinking agent suitable for crosslinking one or more of the filament-forming materials present in the filaments of the present invention. In one example, the crosslinking agent comprises a crosslinking agent capable of crosslinking hydroxyl polymers together, for example via the hydroxyl polymers hydroxyl moieties. Non-limiting examples of suitable crosslinking agents include imidazolidinones, polycarboxylic acids and mixtures thereof. In one example, the crosslinking agent comprises a urea glyoxal adduct crosslinking agent, for example a dihydroxyimidazolidinone, such as dihydroxyethylene urea ("DHEU"). A crosslinking agent can be present in the filament-forming composition and/or filament of the present invention to control the filament's solubility and/or dissolution in a solvent, such as a polar solvent.

In another example, an additive comprises a rheology modifier, such as a shear modifier and/or an extensional modifier. Non-limiting examples of rheology modifiers include but not limited to polyacrylamide, polyurethanes and polyacrylates that may be used in the filaments of the present invention. Non-limiting examples of rheology modifiers are commercially available from The Dow Chemical Company (Midland, Mich.).

In yet another example, an additive comprises one or more colors and/or dyes that are incorporated into the filaments of the present invention to provide a visual signal when the filaments are exposed to conditions of intended use and/or when an active agent is released from the filaments and/or when the filament's morphology changes.

In still yet another example, an additive comprises one or more release agents and/or lubricants. Non-limiting examples of suitable release agents and/or lubricants include fatty acids, fatty acid salts, fatty alcohols, fatty esters, sulfonated fatty acid esters, fatty amine acetates, fatty amide, silicones, aminosilicones, fluoropolymers, and mixtures thereof. In one example, the release agents and/or lubricants are applied to the filament, in other words, after the filament is formed. In one example, one or more release agents/lubricants are applied to the filament prior to collecting the filaments on a collection device to form a nonwoven. In another example, one or more release agents/lubricants are applied to a nonwoven web formed from the filaments of the present invention prior to contacting one or more nonwoven webs, such as in a stack of nonwoven webs. In yet another example, one or more release agents/lubricants are applied to the filament of the present invention and/or nonwoven comprising the filament prior to the filament and/or nonwoven contacting a surface, such as a surface of equipment used in a processing system so as to facilitate removal of the filment and/or nonwoven web and/or to avoid layers of filaments and/or nonwoven webs of the present invention sticking to one another, even inadvertently. In one example, the release agents/lubricants comprise particulates.

In even still yet another example, an additive comprises one or more anti-blocking and/or detackifying agents. Non-limiting examples of suitable anti-blocking and/or detackifying agents include starches, starch derivatives, crosslinked polyvinylpyrrolidone, crosslinked cellulose, microcrystalline cellulose, silica, metallic oxides, calcium carbonate, talc, mica, and mixtures thereof.

"Conditions of intended use" as used herein means the temperature, physical, chemical, and/or mechanical conditions that a filament of the present invention is exposed to when the filament is used for one or more of its designed purposes. For example, if a filament and/or a nonwoven web comprising a filament is designed to be used in a washing machine for laundry care purposes, the conditions of intended use will include those temperature, chemical, physical and/or mechanical conditions present in a washing machine, including any wash water, during a laundry washing operation. In another example, if a filament and/or a nonwoven web comprising a filament is designed to be used by a human as a shampoo for hair care purposes, the conditions of intended use will include those temperature, chemical, physical and/or mechanical conditions present during the shampooing of the human's hair. Likewise, if a filament and/or nonwoven web comprising a filament is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active agent" as used herein means an additive that produces an intended effect in an environment external to a filament and/or nonwoven web comprising the filament of the present, such as when the filament is exposed to conditions of intended use of the filament and/or nonwoven web comprising the filament. In one example, an active agent comprises an additive that treats a surface, such as a hard surface (i.e., kitchen countertops, bath tubs, toilets, toilet bowls, sinks, floors, walls, teeth, cars, windows, mirrors, dishes) and/or a soft surface (i.e., fabric, hair, skin, carpet, crops, plants,). In another example, an active agent comprises an additive that creates a chemical reaction (i.e., foaming, fizzing, coloring, warming, cooling, lathering, disinfecting and/or clarifying and/or chlorinating, such as in clarifying water and/or disinfecting water and/or chlorinating water). In yet another example, an active agent comprises an additive that treats an environment (i.e., deodorizes, purifies, perfumes air). In one example, the active agent is formed in situ, such as during the formation of the filament containing the active agent, for example the filament may comprise a water-soluble polymer (e.g., starch) and a surfactant (e.g., anionic surfactant), which may create a polymer complex or coacervate that functions as the active agent used to treat fabric surfaces.

"Treats" as used herein with respect to treating a surface means that the active agent provides a benefit to a surface or environment. Treats includes regulating and/or immediately improving a surface's or environment's appearance, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

In another example, treating means removing stains and/or odors from fabric articles, such as clothes, towels, linens, and/or hard surfaces, such as countertops and/or dishware including pots and pans.

"Personal care active agent," as used herein, means an active agent that may be applied to mammalian keratinous tissue without undue undesirable effects.

"Keratinous tissue," as used herein, means keratin-containing layers disposed as the outermost protective covering of mammals and includes, but is not limited to, skin, hair, scalp and nails.

"Beauty benefit," as used herein in reference to mammalian keratinous tissue includes, but is not limited to cleansing, sebum inhibition, reducing the oily and/or shiny appearance of skin and/or hair, reducing dryness, itchiness and/or flakiness, reducing skin pore size, exfoliation, desquamation, improving the appearance of the keratinous tissue, conditioning, smoothening, deodorizing skin and/or providing antiperspirant benefits, etc.

"Beauty benefit active agent," as used herein, refers to an active agent that can deliver one or more beauty benefits.

"Skin care active agent" as used herein, means an active agent that when applied to the skin provides a benefit or improvement to the skin. It is to be understood that skin care active agents are useful not only for application to skin, but also to hair, scalp, nails and other mammalian keratinous tissue.

"Hair care active agent" as used herein, means an active agent that when applied to mammalian hair provides a benefit and/or improvement to the hair. Non-limiting examples of benefits and/or improvements to hair include softness, static control, hair repair, dandruff removal, dandruff resistance, hair coloring, shape retention, hair retention, and hair growth.

"Fabric care active agent" as used herein means an active agent that when applied to fabric provides a benefit and/or improvement to the fabric. Non-limiting examples of benefits and/or improvements to fabric include cleaning (for example by surfactants), stain removal, stain reduction, wrinkle removal, color restoration, static control, wrinkle resistance, permanent press, wear reduction, wear resistance, pill removal, pill resistance, soil removal, soil resistance (including soil release), shape retention, shrinkage reduction, softness, fragrance, anti-bacterial, anti-viral, odor resistance, and odor removal.

"Dishwashing active agent" as used herein means an active agent that when applied to dishware, glassware, pots, pans, utensils, and/or cooking sheets provides a benefit and/or improvement to the dishware, glassware, pots, pans and/or cooking sheets. Non-limiting example of benefits and/or improvements to the dishware, glassware, pots, pans, utensils, and/or cooking sheets include food and/or soil removal, cleaning (for example by surfactants) stain removal, stain reduction, grease removal, water spot removal and/or water spot prevention, shining, and polishing.

"Hard surface active agent" as used herein means an active agent when applied to floors, countertops, sinks, windows, mirrors, showers, baths, and/or toilets provides a benefit and/or improvement to the floors, countertops, sinks, windows, mirrors, showers, baths, and/or toilets. Non-limiting example of benefits and/or improvements to the floors, countertops, sinks, windows, mirrors, showers, baths, and/or toilets include food and/or soil removal, grease removal, water spot removal and/or water spot prevention, shining, and polishing.

"Agricultural active agent" as used herein means an active agent that when applied to crops and/or plants provides a benefit and/or improvement to the crops and/or plants. For example, insecticides, herbicides, fertilizers, drought resistant agents, are non-limiting examples of suitable agricultural active agents that may be present in the filaments of the present invention.

"Ingestible active agent" as used herein means an active agent that is suitable for ingestion and/or consuming by an animal, for example a mammal, such as a human, by way of mouth, nose, eyes, ears, skin pores, rectum, vagina, or other orifice or wound (such as delivering an active agent by wound dressing) in the animal. Non-limiting examples of ingestible active agents include feminine hygiene active agents, baby care active agents, oral care active agents, medicinal active agents, vitamins, dietary active agents (for example delivered in a new food form), pet care active agents, and mixtures thereof.

"Liquid treatment active agent" as used herein means an active agent that when applied to a liquid such as water and/or alcohol, provides a benefit and/or improvement to the liquid. For example, chlorine and/or other swimming pool chemicals are non-limiting examples of suitable liquid treatment active agents. In another example, water clarifying and/or water disinfecting active agents, such as are used in commercial water filtering and/or water treatment technologies such as PUR® are non-limiting examples of suitable liquid treatment active agents that may be present in the filaments of the present invention. Further, oil dispersants and/or oil scavenging agents are non-limiting examples of other suitable liquid treatment active agents.

"Industrial active agent" as used herein means an active agent that provides a benefit within an article of manufacture. For example, glue and/or adhesive to provide bonding between two object, insecticides incorporated into insulation, such as housing insulation, oxygen scavenging active agents incorporated into packaging for food and/or perishable goods, insect repellants incorporated into articles used by humans to repel insects, and moisture scavengers incorporated into desiccants are non-limiting examples of industrial active agents that may be present in the filaments of the present invention.

"Weight ratio" as used herein means the weight of filament-forming material (g or %) on a dry weight basis in the filament to the weight of additive, such as active agent(s) (g or %) on a dry weight basis in the filament.

"Hydroxyl polymer" as used herein includes any hydroxyl-containing polymer that can be incorporated into a filament of the present invention, for example as a filament-forming material. In one example, the hydroxyl polymer of the present invention includes greater than 10% and/or greater than 20% and/or greater than 25% by weight hydroxyl moieties.

"Biodegradable" as used herein means, with respect to a material, such as a filament as a whole and/or a polymer within a filament, such as a filament-forming material, that the filament and/or polymer is capable of undergoing and/or does undergo physical, chemical, thermal and/or biological degradation in a municipal solid waste composting facility such that at least 5% and/or at least 7% and/or at least 10% of the original filament and/or polymer is converted into carbon dioxide after 30 days as measured according to the OECD (1992) Guideline for the Testing of Chemicals 301B; Ready Biodegradability—$CO_2$ Evolution (Modified Sturm Test) Test incorporated herein by reference.

"Non-biodegradable" as used herein means, with respect to a material, such as a filament as a whole and/or a polymer within a filament, such as a filament-forming material, that the filament and/or polymer is not capable of undergoing physical, chemical, thermal and/or biological degradation in a municipal solid waste composting facility such that at least 5% of the original filament and/or polymer is converted into carbon dioxide after 30 days as measured according to the OECD (1992) Guideline for the Testing of Chemicals 301B; Ready Biodegradability—$CO_2$ Evolution (Modified Sturm Test) Test incorporated herein by reference.

"Non-thermoplastic" as used herein means, with respect to a material, such as a filament as a whole and/or a polymer within a filament, such as a filament-forming material, that the filament and/or polymer exhibits no melting point and/or softening point, which allows it to flow under pressure, in the absence of a plasticizer, such as water, glycerin, sorbitol, urea and the like.

"Non-thermoplastic, biodegradable filament" as used herein means a filament that exhibits the properties of being biodegradable and non-thermoplastic as defined above.

"Non-thermoplastic, non-biodegradable filament" as used herein means a filament that exhibits the properties of being non-biodegradable and non-thermoplastic as defined above.

"Thermoplastic" as used herein means, with respect to a material, such as a filament as a whole and/or a polymer within a filament, such as a filament-forming material, that the filament and/or polymer exhibits a melting point and/or softening point at a certain temperature, which allows it to flow under pressure, in the absence of a plasticizer "Thermoplastic, biodegradable filament" as used herein means a filament that exhibits the properties of being biodegradable and thermoplastic as defined above.

"Thermoplastic, non-biodegradable filament" as used herein means a filament that exhibits the properties of being non-biodegradable and thermoplastic as defined above.

"Non-cellulose-containing" as used herein means that less than 5% and/or less than 3% and/or less than 1% and/or less than 0.1% and/or 0% by weight of cellulose polymer, cellulose derivative polymer and/or cellulose copolymer is present in filament. In one example, "non-cellulose-containing" means that less than 5% and/or less than 3% and/or less than 1% and/or less than 0.1% and/or 0% by weight of cellulose polymer is present in filament.

"Polar solvent-soluble material" as used herein means a material that is miscible in a polar solvent. In one example, a polar solvent-soluble material is miscible in alcohol and/or water. In other words, a polar solvent-soluble material is a material that is capable of forming a stable (does not phase separate for greater than 5 minutes after forming the homogeneous solution) homogeneous solution with a polar solvent, such as alcohol and/or water at ambient conditions.

"Alcohol-soluble material" as used herein means a material that is miscible in alcohol. In other words, a material that is capable of forming a stable (does not phase separate for greater than 5 minutes after forming the homogeneous solution) homogeneous solution with an alcohol at ambient conditions.

"Water-soluble material" as used herein means a material that is miscible in water. In other words, a material that is capable of forming a stable (does not separate for greater than 5 minutes after forming the homogeneous solution) homogeneous solution with water at ambient conditions.

"Non-polar solvent-soluble material" as used herein means a material that is miscible in a non-polar solvent. In other words, a non-polar solvent-soluble material is a material that is capable of forming a stable (does not phase separate for greater than 5 minutes after forming the homogeneous solution) homogeneous solution with a non-polar solvent.

"Ambient conditions" as used herein means 73° F.±4° F. (about 23° C.±2.2° C.) and a relative humidity of 50%±10%.

"Weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

"Length" as used herein, with respect to a filament, means the length along the longest axis of the filament from one terminus to the other terminus. If a filament has a kink, curl or curves in it, then the length is the length along the entire path of the filament.

"Diameter" as used herein, with respect to a filament, is measured according to the Diameter Test Method described herein. In one example, a filament of the present invention exhibits a diameter of less than 100 μm and/or less than 75 μm and/or less than 50 μm and/or less than 25 μm and/or less than 20 μm and/or less than 15 μm and/or less than 10 μm and/or less than 6 μm and/or greater than 1 μm and/or greater than 3 μm.

"Triggering condition" as used herein in one example means anything, as an act or event, that serves as a stimulus and initiates or precipitates a change in the filament, such as a loss or altering of the filament's physical structure and/or a release of an additive, such as an active agent. In another example, the triggering condition may be present in an environment, such as water, when a filament and/or nonwoven web and/or film of the present invention is added to the water. In other words, nothing changes in the water except for the fact that the filament and/or nonwoven and/or film of the present invention is added to the water.

"Morphology changes" as used herein with respect to a filament's morphology changing means that the filament experiences a change in its physical structure. Non-limiting examples of morphology changes for a filament of the present invention include dissolution, melting, swelling, shrinking, breaking into pieces, exploding, lengthening, shortening, and combinations thereof. The filaments of the present invention may completely or substantially lose their filament physical structure or may have their morphology changed or they may retain or substantially retain their filament physical structure as they are exposed to conditions of intended use.

"By weight on a dry filament basis" means that the weight of the filament measured immediately after the filament has been conditioned in a conditioned room at a temperature of 73° F.±4° F. (about 23° C.±2.2° C.) and a relative humidity of 50%±10% for 2 hours. In one example, "by weight on a dry filament basis" means that the filament comprises less than 20% and/or less than 15% and/or less than 10% and/or less than 7% and/or less than 5% and/or less than 3% and/or to 0% and/or to greater than 0% based on the weight of the filament of moisture, such as water, for example free water, as measured according to the Water Content Test Method described herein.

"Total level" as used herein, for example with respect to the total level of one or more active agents present in the filament, means the sum of the weights or weight percent of all of the subject materials, for example active agents. In other words, a filament may comprise 25% by weight on a dry filament basis of an anionic surfactant, 15% by weight on a dry filament basis of a nonionic surfactant, 10% by weight of a chelant, and 5% of a perfume so that the total level of active agents present in the filament is greater than 50%; namely 55% by weight on a dry filament basis.

"Web" as used herein means a collection of formed fibers and/or filaments, such as a fibrous structure, and/or a sheet formed of fibers and/or filaments, such as continuous filaments, of any nature or origin associated with one another. In one example, the web is a sheet that is formed via a spinning process, not a cast process.

"Nonwoven web" for purposes of the present invention as used herein and as defined generally by European Disposables and Nonwovens Association (EDANA) means a sheet of fibers and/or filaments, such as continuous filaments, of any nature or origin, that have been formed into a web by any means, and may be bonded together by any means, with the exception of weaving or knitting. Felts obtained by wet milling are not nonwoven webs. In one example, a nonwoven web according to the present invention means an orderly arrangement of filaments within a structure in order to perform a function. In one example, a nonwoven web of the present invention is an arrangement comprising a plurality of two or more and/or three or more filaments that are inter-entangled or otherwise associated with one another to form a nonwoven web. In one example, the nonwoven web of the present invention may comprise, in addition to the filaments of the present invention, one or more solid additives, such as particulates and/or fibers.

"Particulates" as used herein means granular substances and/or powders.

As used herein, the articles "a" and "an" when used herein, for example, "an anionic surfactant" or "a fiber" is understood to mean one or more of the material that is claimed or described.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Filament

The filament of the present invention comprises one or more filament-forming materials. In addition to the filament-forming materials, the filament may further comprise one or more active agents that are releasable from the filament, such as when the filament is exposed to conditions of intended use, wherein the total level of the one or more filament-forming materials present in the filament is less than 80% by weight on a dry filament basis and the total level of the one or more active agents present in the filament is greater than 20% by weight on a dry filament basis, is provided.

In one example, the filament of the present invention comprises about 100% and/or greater than 95% and/or greater than 90% and/or greater than 85% and/or greater than 75% and/or greater than 50% by weight on a dry filament basis of one or more filament-forming materials. For example, the filament-forming material may comprise polyvinyl alcohol and/or starch.

In another example, the filament of the present invention comprises one or more filament-forming materials and one or more active agents wherein the total level of filament-forming materials present in the filament is from about 5% to less than 80% by weight on a dry filament basis and the total level of active agents present in the filament is greater than 20% to about 95% by weight on a dry filament basis.

In one example, the filament of the present invention comprises at least 10% and/or at least 15% and/or at least 20% and/or less than less than 80% and/or less than 75% and/or less than 65% and/or less than 60% and/or less than 55% and/or less than 50% and/or less than 45% and/or less than 40% by weight on a dry filament basis of the filament-forming materials and greater than 20% and/or at least 35% and/or at least 40% and/or at least 45% and/or at least 50% and/or at least 60% and/or less than 95% and/or less than 90% and/or less than 85% and/or less than 80% and/or less than 75% by weight on a dry filament basis of active agents.

In one example, the filament of the present invention comprises at least 5% and/or at least 10% and/or at least 15% and/or at least 20% and/or less than 50% and/or less than 45% and/or less than 40% and/or less than 35% and/or less than 30% and/or less than 25% by weight on a dry filament basis of the filament-forming materials and greater than 50% and/or at least 55% and/or at least 60% and/or at least 65% and/or at least 70% and/or less than 95% and/or less than 90% and/or less than 85% and/or less than 80% and/or less than 75% by weight on a dry filament basis of active agents. In one example, the filament of the present invention comprises greater than 80% by weight on a dry filament basis of active agents.

In another example, the one or more filament-forming materials and active agents are present in the filament at a weight ratio of total level of filament-forming materials to active agents of 4.0 or less and/or 3.5 or less and/or 3.0 or less and/or 2.5 or less and/or 2.0 or less and/or 1.85 or less and/or less than 1.7 and/or less than 1.6 and/or less than 1.5 and/or less than 1.3 and/or less than 1.2 and/or less than 1 and/or less than 0.7 and/or less than 0.5 and/or less than 0.4 and/or less than 0.3 and/or greater than 0.1 and/or greater than 0.15 and/or greater than 0.2.

In still another example, the filament of the present invention comprises from about 10% and/or from about 15% to less than 80% by weight on a dry filament basis of a filament-forming material, such as polyvinyl alcohol polymer and/or a starch polymer, and greater than 20% to about 90% and/or to about 85% by weight on a dry filament basis of an active agent. The filament may further comprise a plasticizer, such as glycerin and/or pH adjusting agents, such as citric acid.

In yet another example, the filament of the present invention comprises from about 10% and/or from about 15% to less than 80% by weight on a dry filament basis of a filament-forming material, such as polyvinyl alcohol polymer and/or a starch polymer, and greater than 20% to about 90% and/or to about 85% by weight on a dry filament basis of an active agent, wherein the weight ratio of filament-forming material to active agent is 4.0 or less. The filament may further comprise a plasticizer, such as glycerin and/or pH adjusting agents, such as citric acid.

In even another example of the present invention, a filament comprises one or more filament-forming materials and one or more active agents selected from the group consisting of: enzymes, bleaching agents, builder, chelants, sensates, dispersants, and mixtures thereof that are releasable and/or released when the filament is exposed to conditions of intended use. In one example, the filament comprises a total level of filament forming materials of less than 95% and/or less than 90% and/or less than 80% and/or less than 50% and/or less than 35% and/or to about 5% and/or to about 10% and/or to about 20% by weight on a dry filament basis and a total level of active agents selected from the group consisting of: enzymes, bleaching agents, builder, chelants, and mixtures thereof of greater than 5% and/or greater than 10% and/or greater than 20% and/or greater than 35% and/or greater than 50% and/or greater than 65% and/or to about 95% and/or to about 90% and/or to about 80% by weight on a dry filament basis. In one example, the active agent comprises one or more enzymes. In another example, the active agent comprises one or more bleaching agents. In yet another example, the active agent comprises one or more builders. In still another example, the active agent comprises one or more chelants.

In yet another example of the present invention, the filaments of the present invention may comprise active agents that may create health and/or safety concerns if they become airborne. For example, the filament may be used to inhibit enzymes within the filament from becoming airborne.

In one example, the filaments of the present invention may be meltblown filaments. In another example, the filaments of the present invention may be spunbond filaments. In another example, the filaments may be hollow filaments prior to and/or after release of one or more of its active agents.

The filaments of the present invention may be hydrophilic or hydrophobic. The filaments may be surface treated and/or internally treated to change the inherent hydrophilic or hydrophobic properties of the filament.

In one example, the filament exhibits a diameter of less than 100 µm and/or less than 75 µm and/or less than 50 µm and/or less than 25 µm and/or less than 10 µm and/or less than 5 µm and/or less than 1 µm as measured according to the Diameter Test Method described herein. In another example, the filament of the present invention exhibits a diameter of greater than 1 µm as measured according to the Diameter Test Method described herein. The diameter of a filament of the present invention may be used to control the rate of release of one or more active agents present in the filament and/or the rate of loss and/or altering of the filament's physical structure.

The filament may comprise two or more different active agents. In one example, the filament comprises two or more different active agents, wherein the two or more different active agents are compatible with one another. In another example, the filament comprises two or more different active agents, wherein the two or more different active agents are incompatible with one another.

In one example, the filament may comprise an active agent within the filament and an active agent on an external surface of the filament, such as coating on the filament. The active agent on the external surface of the filament may be the same or different from the active agent present in the filament. If different, the active agents may be compatible or incompatible with one another.

In one example, one or more active agents may be uniformly distributed or substantially uniformly distributed throughout the filament. In another example, one or more active agents may be distributed as discrete regions within the filament. In still another example, at least one active agent is distributed uniformly or substantially uniformly throughout the filament and at least another active agent is distributed as one or more discrete regions within the filament. In still yet another example, at least one active agent is distributed as one or more discrete regions within the filament and at least another active agent is distributed as one or more discrete regions different from the first discrete regions within the filament.

The filaments may be used as discrete articles. In one example, the filaments may be applied to and/or deposited on a carrier substrate, for example a wipe, paper towel, bath tissue, facial tissue, sanitary napkin, tampon, diaper, adult incontinence article, washcloth, dryer sheet, laundry sheet, laundry bar, dry cleaning sheet, netting, filter paper, fabrics, clothes, undergarments, and the like.

In addition, a plurality of the filaments of the present invention may be collected and pressed into a film thus resulting in the film comprising the one or more filament-forming materials and the one or more active agents that are releasable from the film, such as when the film is exposed to conditions of intended use.

In one example, a film of the present invention exhibits an average disintegration time per g of sample of less than 120 and/or less than 100 and/or less than 80 and/or less than 55 and/or less than 50 and/or less than 40 and/or less than 30 and/or less than 20 seconds/gram (s/g) as measured according to the Dissolution Test Method described herein.

In another example, a film of the present invention exhibits an average dissolution time per g of sample of less than 950 and/or less than 900 and/or less than 800 and/or less than 700 and/or less than 600 and/or less than 550 seconds/gram (s/g) as measured according to the Dissolution Test Method described herein.

In one example, a film of the present invention exhibits a thickness of greater than 0.01 mm and/or greater than 0.05 mm and/or greater than 0.1 mm and/or to about 20 mm and/or to about 10 mm and/or to about 5 mm and/or to about 2 mm and/or to about 0.5 mm and/or to about 0.3 mm as measured by the Thickness Test Method described herein.

Filament-forming Material

The filament-forming material is any suitable material, such as a polymer or monomers capable of producing a polymer that exhibits properties suitable for making a filament, such as by a spinning process.

In one example, the filament-forming material may comprise a polar solvent-soluble material, such as an alcohol-soluble material and/or a water-soluble material.

In another example, the filament-forming material may comprise a non-polar solvent-soluble material.

In still another example, the filament forming material may comprise a polar solvent-soluble material and be free (less than 5% and/or less than 3% and/or less than 1% and/or 0% by weight on a dry filament basis) of non-polar solvent-soluble materials.

In yet another example, the filament-forming material may be a film-forming material. In still yet another example, the filament-forming material may be synthetic or of natural origin and it may be chemically, enzymatically, and/or physically modified.

In even another example of the present invention, the filament-forming material may comprise a polymer selected from the group consisting of: polymers derived from acrylic monomers such as the ethylenically unsaturated carboxylic monomers and ethylenically unsaturated monomers, polyvinyl alcohol, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methycelluloses, and carboxymethycelluloses.

In still another example, the filament-forming material may comprises a polymer selected from the group consisting of: polyvinyl alcohol, polyvinyl alcohol derivatives, starch, starch derivatives, cellulose derivatives, hemicellulose, hemicellulose derivatives, proteins, sodium alginate, hydroxypropyl methylcellulose, chitosan, chitosan derivatives, polyethylene glycol, tetramethylene ether glycol, polyvinyl pyrrolidone, hydroxymethyl cellulose, hydroxyethyl cellulose, and mixtures thereof.

In another example, the filament-forming material comprises a polymer is selected from the group consisting of: pullulan, hydroxypropylmethyl cellulose, hydroxyethyl cellulose, hydroxypropyl cellulose, polyvinyl pyrrolidone, carboxymethyl cellulose, sodium alginate, xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, and mixtures thereof.

Polar Solvent-soluble Materials

Non-limiting examples of polar solvent-soluble materials include polar solvent-soluble polymers. The polar solvent-soluble polymers may be synthetic or natural original and may be chemically and/or physically modified. In one example, the polar solvent-soluble polymers exhibit a weight average molecular weight of at least 10,000 g/mol and/or at least 20,000 g/mol and/or at least 40,000 g/mol and/or at least 80,000 g/mol and/or at least 100,000 g/mol and/or at least 1,000,000 g/mol and/or at least 3,000,000 g/mol and/or at least 10,000,000 g/mol and/or at least 20,000,000 g/mol and/or to about 40,000,000 g/mol and/or to about 30,000,000 g/mol.

In one example, the polar solvent-soluble polymers are selected from the group consisting of: alcohol-soluble polymers, water-soluble polymers and mixtures thereof. Non-limiting examples of water-soluble polymers include water-soluble hydroxyl polymers, water-soluble thermoplastic polymers, water-soluble biodegradable polymers, water-soluble non-biodegradable polymers and mixtures thereof. In one example, the water-soluble polymer comprises polyvinyl alcohol. In another example, the water-soluble polymer comprises starch. In yet another example, the water-soluble polymer comprises polyvinyl alcohol and starch.

a. Water-soluble Hydroxyl Polymers—Non-limiting examples of water-soluble hydroxyl polymers in accordance with the present invention include polyols, such as polyvinyl alcohol, polyvinyl alcohol derivatives, polyvinyl alcohol copolymers, starch, starch derivatives, starch copolymers, chitosan, chitosan derivatives, chitosan copolymers, cellulose derivatives such as cellulose ether and ester derivatives, cellulose copolymers, hemicellulose, hemicellulose derivatives, hemicellulose copolymers, gums, arabinans, galactans, proteins and various other polysaccharides and mixtures thereof.

In one example, a water-soluble hydroxyl polymer of the present invention comprises a polysaccharide.

"Polysaccharides" as used herein means natural polysaccharides and polysaccharide derivatives and/or modified polysaccharides. Suitable water-soluble polysaccharides include, but are not limited to, starches, starch derivatives, chitosan, chitosan derivatives, cellulose derivatives, hemicellulose, hemicellulose derivatives, gums, arabinans, galactans and mixtures thereof. The water-soluble polysaccharide may exhibit a weight average molecular weight of from about 10,000 to about 40,000,000 g/mol and/or greater than 100,000 g/mol and/or greater than 1,000,000 g/mol and/or greater than 3,000,000 g/mol and/or greater than 3,000,000 to about 40,000,000 g/mol.

The water-soluble polysaccharides may comprise non-cellulose and/or non-cellulose derivative and/or non-cellulose copolymer water-soluble polysaccharides. Such non-cellulose water-soluble polysaccharides may be selected from the group consisting of: starches, starch derivatives, chitosan, chitosan derivatives, hemicellulose, hemicellulose derivatives, gums, arabinans, galactans and mixtures thereof.

In another example, a water-soluble hydroxyl polymer of the present invention comprises a non-thermoplastic polymer.

The water-soluble hydroxyl polymer may have a weight average molecular weight of from about 10,000 g/mol to about 40,000,000 g/mol and/or greater than 100,000 g/mol and/or greater than 1,000,000 g/mol and/or greater than 3,000,000 g/mol and/or greater than 3,000,000 g/mol to about 40,000,000 g/mol. Higher and lower molecular weight water-soluble hydroxyl polymers may be used in combination with hydroxyl polymers having a certain desired weight average molecular weight.

Well known modifications of water-soluble hydroxyl polymers, such as natural starches, include chemical modifications and/or enzymatic modifications. For example, natural starch can be acid-thinned, hydroxy-ethylated, hydroxy-propylated, and/or oxidized. In addition, the water-soluble hydroxyl polymer may comprise dent corn starch.

Naturally occurring starch is generally a mixture of linear amylose and branched amylopectin polymer of D-glucose units. The amylose is a substantially linear polymer of D-glucose units joined by (1,4)-α-D links. The amylopectin is a highly branched polymer of D-glucose units joined by (1,4)-α-D links and (1,6)-α-D links at the branch points. Naturally occurring starch typically contains relatively high levels of amylopectin, for example, corn starch (64-80% amylopectin), waxy maize (93-100% amylopectin), rice (83-84% amylopectin), potato (about 78% amylopectin), and wheat (73-83% amylopectin). Though all starches are potentially useful herein, the present invention is most commonly practiced with high amylopectin natural starches derived from agricultural sources, which offer the advantages of being abundant in supply, easily replenishable and inexpensive.

As used herein, "starch" includes any naturally occurring unmodified starches, modified starches, synthetic starches and mixtures thereof, as well as mixtures of the amylose or amylopectin fractions; the starch may be modified by physical, chemical, or biological processes, or combinations thereof. The choice of unmodified or modified starch for the present invention may depend on the end product desired. In one embodiment of the present invention, the starch or starch mixture useful in the present invention has an amylopectin content from about 20% to about 100%, more typically from about 40% to about 90%, even more typically from about 60% to about 85% by weight of the starch or mixtures thereof.

Suitable naturally occurring starches can include, but are not limited to, corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches particularly, corn starch and wheat starch, are the preferred starch polymers due to their economy and availability.

Polyvinyl alcohols herein can be grafted with other monomers to modify its properties. A wide range of monomers has been successfully grafted to polyvinyl alcohol. Non-limiting examples of such monomers include vinyl acetate, styrene, acrylamide, acrylic acid, 2-hydroxyethyl methacrylate, acrylonitrile, 1,3-butadiene, methyl methacrylate, methacrylic acid, maleic acid, itaconic acid, sodium vinylsulfonate, sodium allylsulfonate, sodium methylallyl sulfonate, sodium phenylallylether sulfonate, sodium phenylmethallylether sulfonate, 2-acrylamido-methyl propane sulfonic acid (AMPs), vinylidene chloride, vinyl chloride, vinyl amine and a variety of acrylate esters.

In one example, the water-soluble hydroxyl polymer is selected from the group consisting of: polyvinyl alcohols, hydroxymethylcelluloses, hydroxyethylcelluloses, hydroxypropylmethylcelluloses and mixtures thereof. A non-limiting example of a suitable polyvinyl alcohol includes those commercially available from Sekisui Specialty Chemicals America, LLC (Dallas, Tex.) under the CELVOL® trade name. A non-limiting example of a suitable hydroxypropylmethylcellulose includes those commercially available from the Dow Chemical Company (Midland, Mich.) under the METHOCEL® trade name including combinations with above mentioned hydroxypropylmethylcelluloses.

b. Water-soluble Thermoplastic Polymers—Non-limiting examples of suitable water-soluble thermoplastic polymers include thermoplastic starch and/or starch derivatives, polylactic acid, polyhydroxyalkanoate, polycaprolactone, polyesteramides and certain polyesters, and mixtures thereof.

The water-soluble thermoplastic polymers of the present invention may be hydrophilic or hydrophobic. The water-soluble thermoplastic polymers may be surface treated and/or internally treated to change the inherent hydrophilic or hydrophobic properties of the thermoplastic polymer.

The water-soluble thermoplastic polymers may comprise biodegradable polymers.

Any suitable weight average molecular weight for the thermoplastic polymers may be used. For example, the weight average molecular weight for a thermoplastic polymer in accordance with the present invention is greater than about 10,000 g/mol and/or greater than about 40,000 g/mol and/or greater than about 50,000 g/mol and/or less than about 500,000 g/mol and/or less than about 400,000 g/mol and/or less than about 200,000 g/mol.

Non-polar Solvent-soluble Materials

Non-limiting examples of non-polar solvent-soluble materials include non-polar solvent-soluble polymers. Non-limiting examples of suitable non-polar solvent-soluble materials include cellulose, chitin, chitin derivatives, polyolefins, polyesters, copolymers thereof, and mixtures thereof. Non-limiting examples of polyolefins include polypropylene, polyethylene and mixtures thereof. A non-limiting example of a polyester includes polyethylene terephthalate.

The non-polar solvent-soluble materials may comprise a non-biodegradable polymer such as polypropylene, polyethylene and certain polyesters.

Any suitable weight average molecular weight for the thermoplastic polymers may be used. For example, the weight average molecular weight for a thermoplastic polymer in accordance with the present invention is greater than about 10,000 g/mol and/or greater than about 40,000 g/mol and/or greater than about 50,000 g/mol and/or less than about 500,000 g/mol and/or less than about 400,000 g/mol and/or less than about 200,000 g/mol.

Active Agents

Active agents are a class of additives that are designed and intended to provide a benefit to something other than the filament itself, such as providing a benefit to an environment external to the filament. Active agents may be any suitable additive that produces an intended effect under intended use conditions of the filament. For example, the active agent may be selected from the group consisting of: personal cleansing and/or conditioning agents such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; hard surface care agents, and/or conditioning agents such as liquid and/or powder dishwashing agents (for hand dishwashing and/or automatic dishwashing machine applications), and polishing agents; other cleaning and/or conditioning agents such as antimicrobial agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, and mixtures thereof.

Non-limiting examples of suitable cosmetic agents, skin care agents, skin conditioning agents, hair care agents, and hair conditioning agents are described in CTFA Cosmetic Ingredient Handbook, Second Edition, The Cosmetic, Toiletries, and Fragrance Association, Inc. 1988, 1992.

One or more classes of chemicals may be useful for one or more of the active agents listed above. For example, surfactants may be used for any number of the active agents described above. Likewise, bleaching agents may be used for fabric care, hard surface cleaning, dishwashing and even teeth whitening. Therefore, one of ordinary skill in the art will appreciate that the active agents will be selected based upon the desired intended use of the filament and/or nonwoven made therefrom.

For example, if the filament of the present invention and/or nonwoven made therefrom is to be used for hair care and/or conditioning then one or more suitable surfactants, such as a lathering surfactant could be selected to provide the desired benefit to a consumer when exposed to conditions of intended use of the filament and/or nonwoven incorporating the filament.

In one example, if the filament of the present invention and/or nonwoven made therefrom is designed or intended to be used for laundering clothes in a laundry operation, then one or more suitable surfactants and/or enzymes and/or builders and/or perfumes and/or suds suppressors and/or bleaching agents could be selected to provide the desired benefit to a consumer when exposed to conditions of intended use of the filament and/or nonwoven incorporating the filament. In another example, if the filament of the present invention and/or nonwoven made therefrom is designed to be used for laundering clothes in a laundry operation and/or cleaning dishes in a dishwashing operation, then the filament may comprise a laundry detergent composition or dishwashing detergent composition.

In one example, the active agent comprises a non-perfume active agent. In another example, the active agent comprises a non-surfactant active agent. In still another example, the active agent comprises a non-ingestible active agent, in other words an active agent other than an ingestible active agent.

Surfactants

Non-limiting examples of suitable surfactants include anionic surfactants, cationic surfactants, nonionic surfactants, zwitterionic surfactants, amphoteric surfactants, and mixtures thereof. Co-surfactants may also be included in the filaments. For filaments designed for use as laundry detergents and/or dishwashing detergents, the total level of surfactants should be sufficient to provide cleaning including stain and/or odor removal, and generally ranges from about 0.5% to about 95%. Further, surfactant systems comprising two or more surfactants that are designed for use in filaments for laundry detergents and/or dishwashing detergents may include all-anionic surfactant systems, mixed-type surfactant systems comprising anionic-nonionic surfactant mixtures, or nonionic-cationic surfactant mixtures.

The surfactants herein can be linear or branched. In one example, suitable linear surfactants include those derived from agrochemical oils such as coconut oil, palm kernel oil, soybean oil, or other vegetable-based oils.

a. Anionic Surfactants

Non-limiting examples of suitable anionic surfactants include alkyl sulfates, alkyl ether sulfates, branched alkyl sulfates, branched alkyl alkoxylates, branched alkyl alkoxylate sulfates, mid-chain branched alkyl aryl sulfonates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Alkyl sulfates and alkyl ether sulfates suitable for use herein include materials with the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. Other suitable anionic surfactants are described in McCutcheon's Detergents and Emulsifiers, North American Edition (1986), Allured Publishing Corp. and McCutcheon's, Functional Materials, North American Edition (1992), Allured Publishing Corp.

In one example, anionic surfactants useful in the filaments of the present invention include $C_9$-$C_{15}$ alkyl benzene sulfonates (LAS), $C_8$-$C_{20}$ alkyl ether sulfates, for example alkyl poly(ethoxy) sulfates, $C_8$-$C_{20}$ alkyl sulfates, and mixtures thereof. Other anionic surfactants include methyl ester sulfonates (MES), secondary alkane sulfonates, methyl ester ethoxylates (MEE), sulfonated estolides, and mixtures thereof.

In another example, the anionic surfactant is selected from the group consisting of: $C_{11}$-$C_{18}$ alkyl benzene sulfonates ("LAS") and primary, branched-chain and random $C_{10}$-$C_{20}$ alkyl sulfates ("AS"), $C_{10}$-$C_{18}$ secondary (2,3) alkyl sulfates of the formula $CH_3(CH_2)_x(CHOSO_3^-M^+)$ $CH_3$ and $CH_3(CH_2)_y(CHOSO_3^-M^+)$ $CH_2CH_3$ where x and (y+1) are integers of at least about 7, preferably at least about 9, and M is a water-solubilizing cation, especially sodium, unsaturated sulfates such as oleyl sulfate, the $C_{10}$-$C_{18}$ alpha-sulfonated fatty acid esters, the $C_{10}$-$C_{18}$ sulfated alkyl polyglycosides, the $C_{10}$-$C_{18}$ alkyl alkoxy sulfates ("AE$_x$S") wherein x is from 1-30, and $C_{10}$-$C_{18}$ alkyl alkoxy carboxylates, for example comprising 1-5 ethoxy units, mid-chain branched alkyl sulfates as discussed in U.S. Pat. Nos. 6,020,303 and 6,060,443; mid-chain branched alkyl alkoxy sulfates as discussed in U.S. Pat. Nos. 6,008,181 and 6,020,303; modified alkylbenzene sulfonate (MLAS) as discussed in WO 99/05243, WO 99/05242 and WO 99/05244; methyl ester sulfonate (MES); and alpha-olefin sulfonate (AOS).

Other suitable anionic surfactants that may be used are alkyl ester sulfonate surfactants including sulfonated linear esters of $C_8$-$C_{20}$ carboxylic acids (i.e., fatty acids). Other suitable anionic surfactants that may be used include salts of soap, $C_8$-$C_{22}$ primary of secondary alkanesulfonates, $C_8$-$C_{24}$ olefinsulfonates, sulfonated polycarboxylic acids, $C_8$-$C_{24}$ alkylpolyglycolethersulfates (containing up to 10 moles of ethylene oxide); alkyl glycerol sulfonates, fatty acyl glycerol sulfonates, fatty oleoyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (for example saturated and unsaturated $C_{12}$-$C_{18}$ monoesters) and diesters of sulfosuccinates (for example saturated and unsaturated $C_6$-$C_{12}$ diesters), sulfates of alkylpolysaccharides such as the sulfates of alkylpolyglucoside, and alkyl polyethoxy carboxylates such as those of the formula $RO(CH_2CH_2O)_k$—$CH_2COO$-$M+$ wherein R is a $C_8$-$C_{22}$ alkyl, k is an integer from 0 to 10, and M is a soluble salt-forming cation.

Other exemplary anionic surfactants are the alkali metal salts of $C_{10}$-$C_{16}$ alkyl benzene sulfonic acids, preferably $C_{11}$-$C_{14}$ alkyl benzene sulfonic acids. In one example, the alkyl group is linear. Such linear alkyl benzene sulfonates are known as "LAS". Such surfactants and their preparation are described for example in U.S. Pat. Nos. 2,220,099 and 2,477,383. IN another example, the linear alkyl benzene sulfonates include the sodium and/or potassium linear straight chain alkylbenzene sulfonates in which the average number of carbon atoms in the alkyl group is from about 11 to 14. Sodium $C_{11}$-$C_{14}$ LAS, e.g., $C_{12}$ LAS, is a specific example of such surfactants.

Another exemplary type of anionic surfactant comprises linear or branched ethoxylated alkyl sulfate surfactants. Such materials, also known as alkyl ether sulfates or alkyl polyethoxylate sulfates, are those which correspond to the formula: $R'$—O—$(C_2H_4O)_n$—$SO_3M$ wherein R' is a $C_8$-$C_{20}$ alkyl group, n is from about 1 to 20, and M is a salt-forming cation. In a specific embodiment, R' is $C_{10}$-$C_{18}$ alkyl, n is from about 1 to 15, and M is sodium, potassium, ammonium, alkylammonium, or alkanolammonium. In more specific embodiments, R' is a $C_{12}$-$C_{16}$, n is from about 1 to 6 and M is sodium. The alkyl ether sulfates will generally be used in the form of mixtures comprising varying R' chain lengths and varying degrees of ethoxylation. Frequently such mixtures will inevitably also contain some non-ethoxylated alkyl sulfate materials, i.e., surfactants of the above ethoxylated alkyl sulfate formula wherein n=0. Non-ethoxylated alkyl sulfates may also be added separately to the compositions of this invention and used as or in any anionic surfactant component which may be present. Specific examples of non-alkoyxylated, e.g., non-ethoxylated, alkyl ether sulfate surfactants are those produced by the sulfation of higher $C_8$-$C_{20}$ fatty alcohols. Conventional primary alkyl sulfate surfactants have the general formula: $R''OSO_3^-M^+$ wherein R'' is typically a $C_8$-$C_{20}$ alkyl group, which may be straight chain or branched chain, and M is a water-solubilizing cation. In specific embodiments, R'' is a $C_{10}$-$C_{15}$ alkyl group, and M is alkali metal, more specifically R'' is $C_{12}$-$C_{14}$ alkyl and M is sodium. Specific, non-limiting examples of anionic surfactants useful herein include: a) $C_{11}$-$C_{18}$ alkyl benzene sulfonates (LAS); b) $C_{10}$-$C_{20}$ primary, branched-chain and random alkyl sulfates (AS); c) $C_{10}$-$C_{18}$ secondary (2,3)-alkyl sulfates having following formulae:

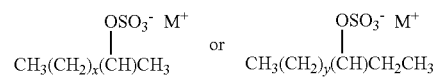

wherein M is hydrogen or a cation which provides charge neutrality, and all M units, whether associated with a surfactant or adjunct ingredient, can either be a hydrogen atom or a cation depending upon the form isolated by the artisan or the relative pH of the system wherein the compound is used, with non-limiting examples of suitable cations including sodium, potassium, ammonium, and mixtures thereof, and x is an integer of at least 7 and/or at least about 9, and y is an integer of at least 8 and/or at least 9; d) $C_{10}$-$C_{18}$ alkyl alkoxy sulfates (AE$_z$S) wherein z, for example, is from 1-30; e) $C_{10}$-$C_{18}$ alkyl alkoxy carboxylates preferably comprising 1-5 ethoxy units; f) mid-chain branched alkyl sulfates as discussed in U.S. Pat. Nos. 6,020,303 and 6,060,443; g) mid-chain branched alkyl alkoxy sulfates as discussed in U.S. Pat. Nos. 6,008,181 and 6,020,303; h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548.; i) methyl ester sulfonate (MES); and j) alpha-olefin sulfonate (AOS).

b. Cationic Surfactants

Non-limiting examples of suitable cationic surfactants include, but are not limited to, those having the formula (I):

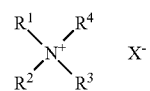

in which $R^1$, $R^2$, $R^3$, and $R^4$ are each independently selected from (a) an aliphatic group of from 1 to 26 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate, nitrate, sulphate, and alkylsulphate radicals. In one example, the alkylsulphate radical is methosulfate and/or ethosulfate.

Suitable quaternary ammonium cationic surfactants of general formula (I) may include cetyltrimethylammonium chloride, behenyltrimethylammonium chloride (BTAC), stearyltrimethyl ammonium chloride, cetylpyridinium chloride, octadecyltrimethylammonium chloride, hexadecyltrimethylammonium chloride, octyldimethylbenzyl ammonium chloride, decyldimethylbenzylammonium chloride, stearyldimethylbenzylammonium chloride, didodecyldimethylammonium chloride, didecyldimethylammonium chloride, dioctadecyldimethylammonium chloride, distearyldimethyl ammonium chloride, tallowtrimethyl ammonium chloride, cocotrimethylammonium chloride, 2-ethyl hexyl stearyldimethylammonum chloride, dipalmitoylethyl dimethyl ammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate.

Non-limiting examples of suitable cationic surfactants are commercially available under the trade names ARQUAD® from Akzo Nobel Surfactants (Chicago, Ill.).

In one example, suitable cationic surfactants include quaternary ammonium surfactants, for example that have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and 6,022,844; and amino surfactants as discussed in U.S. Pat. No. 6,221,825 and WO 00/47708, for example amido propyldimethyl amine (APA).

Other suitable cationic surfactants include salts of primary, secondary, and tertiary fatty amines. In one embodiment, the alkyl groups of such amines have from about 12 to about 22 carbon atoms, and can be substituted or unsubstituted. These amines are typically used in combination with an acid to provide the cationic species.

The cationic surfactant may include cationic ester surfactants having the formula:

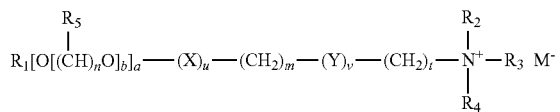

wherein $R_1$ is a $C_5$-$C_{31}$ linear or branched alkyl, alkenyl or alkaryl chain or $M^-.N^+(R_6R_7R_8)(CH_2)_s$; X and Y, independently, are selected from the group consisting of COO, OCO, O, CO, OCOO, CONH, NHCO, OCONH and NHCOO wherein at least one of X or Y is a COO, OCO, OCOO, OCONH or NHCOO group; $R_2$, $R_3$, $R_4$, $R_6$, $R_7$ and $R_8$ are independently selected from the group consisting of alkyl, alkenyl, hydroxyalkyl, hydroxyalkenyl and alkaryl groups having from 1 to 4 carbon atoms; and $R_5$ is independently H or a $C_1$-$C_3$ alkyl group; wherein the values of m, n, s and t independently lie in the range of from 0 to 8, the value of b lies in the range from 0 to 20, and the values of a, u and v independently are either 0 or 1 with the proviso that at least one of u or v must be 1; and wherein M is a counter anion. In one example, $R_2$, $R_3$ and $R_4$ are independently selected from $CH_3$ and —$CH_2CH_2OH$. In another example, M is selected from the group consisting of halide, methyl sulfate, sulfate, nitrate, chloride, bromide, or iodide.

The cationic surfactants of the present invention may be chosen for use in personal cleansing applications. In one example, such cationic surfactants may be included in the filament and/or fiber at a total level by weight of from about 0.1% to about 10% and/or from about 0.5% to about 8% and/or from about 1% to about 5% and/or from about 1.4% to about 4%, in view of balance among ease-to-rinse feel, rheology and wet conditioning benefits. A variety of cationic surfactants including mono- and di-alkyl chain cationic surfactants can be used in the compositions of the present invention. In one example, the cationic surfactants include mono-alkyl chain cationic surfactants in view of providing desired gel matrix and wet conditioning benefits. The mono-alkyl cationic surfactants are those having one long alkyl chain which has from 12 to 22 carbon atoms and/or from 16 to 22 carbon atoms and/or from 18 to 22 carbon atoms in its alkyl group, in view of providing balanced wet conditioning benefits. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. Such mono-alkyl cationic surfactants include, for example, mono-alkyl quaternary ammonium salts and mono-alkyl amines. Mono-alkyl quaternary ammonium salts include, for example, those having a non-functionalized long alkyl chain. Mono-alkyl amines include, for example, mono-alkyl amidoamines and salts thereof. Other cationic surfactants such as di-alkyl chain cationic surfactants may also be used alone, or in combination with the mono-alkyl chain cationic surfactants. Such di-alkyl chain cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

In one example the cationic ester surfactants are hydrolyzable under the conditions of a laundry wash.

c. Nonionic Surfactants

Non-limiting examples of suitable nonionic surfactants include alkoxylated alcohols (AE's) and alkyl phenols, polyhydroxy fatty acid amides (PFAA's), alkyl polyglycosides (APG's), $C_{10}$-$C_{18}$ glycerol ethers, and the like.

In one example, non-limiting examples of nonionic surfactants useful in the present invention include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates such as PLURONIC® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, $BAE_x$, wherein x is from 1-30, as discussed in U.S. Pat. Nos. 6,153,577, 6,020,303 and 6,093,856; alkylpolysaccharides as discussed in U.S. Pat. No. 4,565,647 Llenado, issued Jan. 26, 1986; specifically alkylpolyglycosides as discussed in U.S. Pat. Nos. 4,483,780 and 4,483,779; polyhydroxy detergent acid amides as discussed in U.S. Pat. No. 5,332,528; and ether capped poly(oxyalkylated) alcohol surfactants as discussed in U.S. Pat. No. 6,482,994 and WO 01/42408.

Examples of commercially available nonionic surfactants suitable for the present invention include: Tergitol® 15-S-9 (the condensation product of $C_{11}$-$C_{15}$ linear alcohol with 9 moles ethylene oxide) and Tergitol® 24-L-6 NMW (the condensation product of $C_{12}$-$C_{14}$ primary alcohol with 6 moles ethylene oxide with a narrow molecular weight distribution), both marketed by Dow Chemical Company; Neodol® 45-9 (the condensation product of $C_{14}$-$C_{15}$ linear alcohol with 9 moles of ethylene oxide), Neodol® 23-3 (the condensation product of $C_{12}$-$C_{13}$ linear alcohol with 3 moles of ethylene oxide), Neodol® 45-7 (the condensation product of $C_{14}$-$C_{15}$ linear alcohol with 7 moles of ethylene oxide) and Neodol® 45-5 (the condensation product of $C_{14}$-$C_{15}$ linear alcohol with 5 moles of ethylene oxide) marketed by Shell Chemical Company; Kyro® EOB (the condensation product of $C_{13}$-$C_{15}$ alcohol with 9 moles ethylene oxide), marketed by The Procter & Gamble Company; and Genapol LA 030 or 050 (the condensation product of $C_{12}$-$C_{14}$ alcohol with 3 or 5 moles of ethylene oxide) marketed by Hoechst. The nonionic surfactants may exhibit an HLB range of from about 8 to about 17 and/or from about 8 to about 14. Condensates with propylene oxide and/or butylene oxides may also be used.

Non-limiting examples of semi-polar nonionic surfactants useful in the present invention include: water-soluble amine oxides containing one alkyl moiety of from about 10 to about 18 carbon atoms and 2 moieties selected from the group consisting of alkyl moieties and hydroxyalkyl moieties containing from about 1 to about 3 carbon atoms; water-soluble phosphine oxides containing one alkyl moiety of from about 10 to about 18 carbon atoms and 2 moieties selected from the group consisting of alkyl moieties and hydroxyalkyl moieties containing from about 1 to about 3 carbon atoms; and water-soluble sulfoxides containing one alkyl moiety of from about 10 to about 18 carbon atoms and a moiety selected from the group consisting of alkyl moieties and hydroxyalkyl moieties of from about 1 to about 3 carbon atoms. See WO 01/32816, U.S. Pat. Nos. 4,681,704, and 4,133,779.

Another class of nonionic surfactants that may be used in the present invention includes polyhydroxy fatty acid amide surfactants of the following formula:

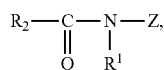

wherein $R^1$ is H, or $C_{1-4}$ hydrocarbyl, 2-hydroxy ethyl, 2-hydroxy propyl or a mixture thereof, $R_2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. In one example, $R^1$ is methyl, $R_2$ is a straight $C_{11-15}$ alkyl or $C_{15-17}$ alkyl or alkenyl chain such as coconut alkyl or mixtures thereof, and Z is derived from a reducing sugar such as glucose, fructose, maltose, lactose, in a reductive amination reaction. Typical examples include the $C_{12}$-$C_{18}$ and $C_{12}$-$C_{14}$ N-methylglucamides.

Alkylpolyaccharide surfactants may also be used as a nonionic surfactant in the present invention.

Polyethylene, polypropylene, and polybutylene oxide condensates of alkyl phenols are also suitable for use as a nonionic surfactant in the present invention. These compounds include the condensation products of alkyl phenols having an alkyl group containing from about 6 to about 14 carbon atoms, in either a straight-chain or branched-chain configuration with the alkylene oxide. Commercially available nonionic surfactants of this type include Igepal CO-630, marketed by the GAF Corporation; and Triton® X-45, X-114, X-100 and X-102, all marketed by the Dow Chemical Company.

Examples of other suitable nonionic surfactants are the commercially-available Pluronic® surfactants, marketed by BASF, the commercially available Tetronic® compounds, marketed by BASF.

d. Zwitterionic Surfactants

Non-limiting examples of zwitterionic or ampholytic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{12}$ to $C_{18}$) amine oxides and sulfo and hydroxy betaines, such as N-alkyl-N,N-dimethylammino-1-propane sulfonate where the alkyl group can be $C_8$ to $C_{18}$ and in certain embodiments from $C_{10}$ to $C_{14}$.

e. Amphoteric Surfactants

Non-limiting examples of amphoteric surfactants include: aliphatic derivatives of secondary or tertiary amines, or aliphatic derivatives of heterocyclic secondary and tertiary amines in which the aliphatic radical can be straight- or branched-chain and mixtures thereof. One of the aliphatic substituents may contain at least about 8 carbon atoms, for example from about 8 to about 18 carbon atoms, and at least one contains an anionic water-solubilizing group, e.g. carboxy, sulfonate, sulfate. See U.S. Pat. No. 3,929,678 at column 19, lines 18-35, for suitable examples of amphoteric surfactants.

f. Co-surfactants

In addition to the surfactants described above, the filaments may also contain co-surfactants. In the case of laundry detergents and/or dishwashing detergents, they typically contain a mixture of surfactant types in order to obtain broad-scale cleaning performance over a variety of soils and stains and under a variety of usage conditions. A wide range of these co-surfactants can be used in the filaments of the present invention. A typical listing of anionic, nonionic, ampholytic and zwitterionic classes, and species of these co-surfactants, is given herein above, and may also be found in U.S. Pat. No. 3,664,961. In other words, the surfactant systems herein may also include one or more co-surfactants selected from non-ionic, cationic, anionic, zwitterionic or mixtures thereof. The selection of co-surfactant may be dependent upon the desired benefit. The surfactant system may comprise from 0% to about 10%, or from about 0.1% to about 5%, or from about 1% to about 4% by weight of the composition of other co-surfactant(s).

g. Amine-neutralized anionic Surfactants

The anionic surfactants and/or anionic co-surfactants of the present invention may exist in an acid form, which may be neutralized to form a surfactant salt. In one example, the filaments may comprise a surfactant salt form. Typical agents for neutralization include a metal counterion base such as hydroxides, eg, NaOH or KOH. Other agents for neutralizing the anionic surfactants and anionic co-surfactants in their acid forms include ammonia, amines, or alkanolamines. In one example, the neutralizing agent comprises an alkanolamine, for example an alkanolamine selected from the group consisting of: monoethanolamine, diethanolamine, triethanolamine, and other linear or branched alkanolamines known in the art; for example, 2-amino-1-propanol, 1-aminopropanol, monoisopropanol amine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Perfumes

One or more perfume and/or perfume raw materials such as accords and/or notes may be incorporated into one or more of the filaments of the present invention. The perfume may comprise a perfume ingredient selected from the group consisting of: aldehyde perfume ingredients, ketone perfume ingredients, and mixtures thereof.

One or more perfumes and/or perfumery ingredients may be included in the filaments of the present invention. A wide variety of natural and synthetic chemical ingredients useful as perfumes and/or perfumery ingredients include but not limited to aldehydes, ketones, esters, and mixtures thereof. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. In one example, a finished perfume typically comprises from about 0.01% to about 2%, by weight on a dry filament basis.

Perfume Delivery Systems

Certain perfume delivery systems, methods of making certain perfume delivery systems and the uses of such perfume delivery systems are disclosed in USPA 2007/0275866 A1. Non-limiting examples of perfume delivery systems include the following:

I. Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

a.) Matrix Systems: The fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are know that may control perfume release. Absorption and/or adsorption into or onto polymeric particles, films, solutions, and the like are aspects of this technology. Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded perfume associated with the polymer until the moment or moments of perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and release is typically via perfume diffusion. The use of such equilibrium system polymers has the potential to decrease the neat product odor intensity of the neat product (usually more so in the case of pre-loaded standard system). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that perfume release occurs within the time frame of the application to impact the desired consumer touch point or touch points. Suitable microparticles and micro-latexes as well as methods of making same may be found in USPA 2005/0003980 A1. Matrix systems also include hot melt adhesives and perfume plastics. In addition, hydrophobically modified polysaccharides may be formulated into the perfumed product to increase perfume deposition and/or modify perfume release. All such matrix systems, including for example polysaccarides and nanolatexes may be combined with other PDTs, including other PAD systems such as PAD reservoir systems in the form of a perfume microcapsule (PMC). Polymer Assisted Delivery (PAD) matrix systems may include those described in the following references: U.S. Patent Applications 2004/0110648 A1; 2004/0092414 A1; 2004/0091445 A1 and 2004/0087476 A1; and U.S. Pat. Nos. 6,531,444; 6,024,943; 6,042,792; 6,051,540; 4,540,721 and 4,973,422.

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Suitable silicones as well as making same may be found in WO 2005/102261; USPA 20050124530A1; USPA 20050143282A1; and WO 2003/015736. Functionalized silicones may also be used as described in USPA 2006/003913 A1. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP). Other such examples may be found in U.S. Pat. No. 4,911,852; USPA 2004/0058845 A1; USPA 2004/0092425 A1 and USPA 2005/0003980 A1.

b.) Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Stable shell materials include polyacrylate-based materials obtained as reaction product of an oil soluble or dispersible amine with a multifunctional acrylate or methacrylate monomer or oligomer, an oil soluble acid and an initiator, in presence of an anionic emulsifier comprising a water soluble or water dispersible acrylic acid alkyl acid copolymer, an alkali or alkali salt. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged. Scratch and sniff technologies are yet another example of PAD. Perfume microcapsules (PMC) may include those described in the following references: U.S. Patent Applications: 2003/0125222 A1; 2003/215417 A1; 2003/216488 A1; 2003/158344 A1; 2003/165692 A1; 2004/071742 A1; 2004/071746 A1; 2004/072719 A1; 2004/072720 A1; 2006/0039934 A1; 2003/203829 A1; 2003/195133 A1; 2004/087477 A1; 2004/0106536 A1; and U.S. Pat. Nos. 6,645,479 B1; 6,200,949 B1; 4,882,220; 4,917,920; 4,514,461; 6,106,875 and 4,234,627, 3,594,328 and U.S. RE 32713, PCT Patent Application: WO 2009/134234 A1, WO 2006/127454 A2, WO 2010/079466 A2, WO 2010/079467 A2, WO 2010/079468 A2, WO 2010/084480 A2.

II. Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a CLogP greater than about 2. Molecule-Assisted Delivery (MAD) may also include those described in U.S. Pat. Nos. 7,119,060 and 5,506,201.

III. Fiber-Assisted Delivery (FAD): The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be woven and non-woven as well as natural or synthetic. Natural fibers include those produced by plants, animals, and geological processes, and include but are not limited to cellulose materials such as cotton, linen, hemp jute, flax, ramie, and sisal, and fibers used to manufacture paper and cloth. Fiber-Assisted Delivery may consist of the use of wood fiber, such as thermomechanical pulp and bleached or unbleached kraft or sulfite pulps. Animal fibers consist largely of particular proteins, such as silk, sinew, catgut and hair (including wool). Polymer fibers based on synthetic chemicals include but are not limited to polyamide nylon, PET or PBT polyester, phenol-formaldehyde (PF), polyvinyl alcohol fiber (PVOH), polyvinyl chloride fiber (PVC), polyolefins (PP and PE), and acrylic polymers. All such fibers may be pre-loaded with a perfume, and then added to a product that may or may not contain free perfume and/or one or more perfume delivery technologies. In one aspect, the fibers may be added to a product prior to being loaded with a perfume, and then loaded with a perfume by adding a perfume that may diffuse into the fiber, to the product. Without wishing to be bound by theory, the perfume may absorb onto or be adsorbed into the fiber, for example, during product storage, and then be released at one or more moments of truth or consumer touch points.

IV. Amine Assisted Delivery (AAD): The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one aspect, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one aspect, such materials contain at least one primary amine. This technology will allow increased longevity and controlled release also of low ODT perfume notes (e.g., aldehydes, ketones, enones) via amine functionality, and delivery of other PRMs, without being bound by theory, via polymer-assisted delivery for polymeric amines. Without technology, volatile top notes can be lost too quickly, leaving a higher ratio of middle and base notes to top notes. The use of a polymeric amine allows higher levels of top notes and other PRMS to be used to obtain freshness longevity without causing neat product odor to be more intense than desired, or allows top notes and other PRMs to be used more efficiently. In one aspect, AAD systems are effective at delivering PRMs at pH greater than about neutral. Without wishing to be bound by theory, conditions in which more of the amines of the AAD system are deprotonated may result in an increased affinity of the deprotonated amines for PRMs such as aldehydes and ketones, including unsaturated ketones and enones such as damascone. In another aspect, polymeric amines are effective at delivering PRMs at pH less than about neutral. Without wishing to be bound by theory, conditions in which more of the amines of the AAD system are protonated may result in a decreased affinity of the protonated amines for PRMs such as aldehydes and ketones, and a strong affinity of the polymer framework for a broad range of PRMs. In such an aspect, polymer-assisted delivery may be delivering more of the perfume benefit; such systems are a subspecies of AAD and may be referred to as Amine-Polymer-Assisted Delivery or APAD. In some cases when the APAD is employed in a composition that has a pH of less than seven, such APAD systems may also be considered Polymer-Assisted Delivery (PAD). In yet another aspect, AAD and PAD systems may interact with other materials, such as anionic surfactants or polymers to form coacervate and/or coacervates-like systems. In another aspect, a material that contains a heteroatom other than nitrogen, for example sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. Suitable AAD systems as well as methods of making same may be found in U.S. Patent Applications 2005/0003980 A1; 2003/0199422 A1; 2003/0036489 A1; 2004/0220074 A1 and U.S. Pat. No. 6,103,678.

V. Cyclodextrin Delivery System (CD): This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit. Suitable CDs as well as methods of making same may be found in USPA 2005/0003980 A1 and 2006/0263313 A1 and U.S. Pat. Nos. 5,552,378; 3,812,011; 4,317,881; 4,418,144 and 4,378,923.

VI. Starch Encapsulated Accord (SEA): The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid. Suitable SEAs as well as methods of making same may be found in USPA 2005/0003980 A1 and U.S. Pat. No. 6,458,754 B1.

VII. Inorganic Carrier Delivery System (ZIC): This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Suitable zeolite and inorganic carriers as well as methods of making same may be found in USPA 2005/0003980 A1 and U.S. Pat. Nos. 5,858,959; 6,245,732 B1; 6,048,830 and 4,539,135. Silica is another form of ZIC. Another example of a suitable inorganic carrier includes inorganic tubules, where the perfume or other active material is contained within the lumen of the nano- or micro-tubules. In one aspect, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded perfume. Monomeric and/or polymeric materials, including starch encapsulation, may be used to coat, plug, cap, or otherwise encapsulate the PLT. Suitable PLT systems as well as methods of making same may be found in U.S. Pat. No. 5,651,976.

VIII. Pro-Perfume (PP): This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Pro-perfumes may provide enhanced perfume delivery properties such as increased perfume deposition, longevity, stability, retention, and the like. Pro-perfumes include those that are monomeric (non-polymeric) or polymeric, and may be pre-fooled or may be formed in-situ under equilibrium conditions, such as those that may be present during in-product storage or on the wet or dry situs. Nonlimiting examples of pro-perfumes include Michael adducts (e.g., beta-amino ketones), aromatic or non-aromatic imines (Schiff bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester. The typical trigger for perfume release is exposure to water; although other triggers may include enzymes, heat, light, pH change, autoxidation, a shift of equilibrium, change in concentration or ionic strength and others. For aqueous-based products, light-triggered pro-perfumes are particularly suited. Such photo-pro-perfumes (PPPs) include but are not limited to those that release coumarin derivatives and perfumes and/or pro-perfumes upon being triggered. The released pro-perfume may release one or more PRMs by means of any of the above mentioned triggers. In one aspect, the photo-pro-perfume releases a nitrogen-based pro-perfume when exposed to a light and/or moisture trigger. In another aspect, the nitrogen-based pro-perfume, released from the photo-pro-perfume, releases one or more PRMs selected, for example, from aldehydes, ketones (including enones) and alcohols. In still another aspect, the PPP releases a dihydroxy coumarin derivative. The light-triggered pro-perfume may also be an ester that releases a coumarin derivative and a perfume alcohol. In one aspect the pro-perfume is a dimethoxybenzoin derivative as described in USPA 2006/0020459 A1. In another aspect the pro-perfume is a 3',5'-dimethoxybenzoin (DMB) derivative that releases an alcohol upon exposure to electromagnetic radiation. In yet another aspect, the pro-perfume releases one or more low ODT PRMs, including tertiary alcohols such as linalool, tetrahydrolinalool, or dihydromyrcenol, Suitable pro-perfumes and methods of making same can be found in U.S. Pat. Nos. 7,018,978 B2; 6,987,084 B2; 6,956,013 B2; 6,861,402 B1; 6,544,945 B1; 6,093,691; 6,277,796 B1; 6,165,953; 6,316,397 B1; 6,437,150 B1; 6,479,682 B1; 6,096,918; 6,218,355 B1; 6,133,228; 6,147,037; 7,109,153 B2; 7,071,151 B2;

6,987,084 B2; 6,610,646 B2 and 5,958,870, as well as can be found in USPA 2005/0003980 A1 and USPA 2006/0223726 A1.

a.) Amine Reaction Product (ARP): For purposes of the present application, ARP is a subclass or species of PP. One may also use "reactive" polymeric amines in which the amine functionality is pre-reacted with one or more PRMs to form an amine reaction product (ARP). Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxylamines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen, for example oxygen, sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Bleaching Agents

The filaments of the present invention may comprise one or more bleaching agents. Non-limiting examples of suitable bleaching agents include peroxyacids, perborate, percarbonate, chlorine bleaches, oxygen bleaches, hypohalite bleaches, bleach precursors, bleach activators, bleach catalysts, hydrogen peroxide, bleach boosters, photobleaches, bleaching enzymes, free radical initiators, peroxygen bleaches, and mixtures thereof.

One or more bleaching agents may be included in the filaments of the present invention may be included at a level from about 1% to about 30% and/or from about 5% to about 20% by weight on a dry filament basis. If present, bleach activators may be present in the filaments of the present invention at a level from about 0.1% to about 60% and/or from about 0.5% to about 40% by weight on a dry filament basis.

Non-limiting examples of bleaching agents include oxygen bleach, perborate bleach, percarboxylic acid bleach and salts thereof, peroxygen bleach, persulfate bleach, percarbonate bleach, and mixtures thereof. Further, non-limiting examples of bleaching agents are disclosed in U.S. Pat. No. 4,483,781, European Patent Application 0 133 354, U.S. Pat. Nos. 4,412,934, and 4,634,551.

Non-limiting examples of bleach activators (e.g., acyl lactam activators) are disclosed in U.S. Pat. Nos. 4,915,854; 4,412,934; 4,634,551; 4,634,551; and 4,966,723.

In one example, the bleaching agent comprises a transition metal bleach catalyst, which may be encapsulated. The transition metal bleach catalyst typically comprises a transition metal ion, for example a transition metal ion from a transition metal selected from the group consisting of: Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV). In one example, the transition metal is selected from the group consisting of: Mn(II), Mn(III), Mn(IV), Fe(II), Fe(III), Cr(II), Cr(III), Cr(IV), Cr(V), and Cr(VI). The transition metal bleach catalyst typically comprises a ligand, for example a macropolycyclic ligand, such as a cross-bridged macropolycyclic ligand. The transition metal ion may be coordinated with the ligand. Further, the ligand may comprise at least four donor atoms, at least two of which are bridgehead donor atoms. Non-limiting examples of suitable transition metal bleach catalysts are described in U.S. Pat. Nos 5,580,485, 4,430,243; 4,728,455; 5,246,621; 5,244,594; 5,284,944; 5,194,416; 5,246,612; 5,256,779; 5,280,117; 5,274,147;5,153,161; 5,227,084; 5,114,606; 5,114,611, EP 549,271 A1; EP 544,490 A1; EP 549,272 A1; and EP 544,440 A2. In one example, a suitable transition metal bleach catalyst comprises a manganese-based catalyst, for example disclosed in U.S. Pat. No. 5,576,282. In another example, suitable cobalt bleach catalysts are described, in U.S. Pat. Nos. 5,597,936 and 5,595,967. Such cobalt catalysts are readily prepared by known procedures, such as taught for example in U.S. Pat. Nos. 5,597,936, and 5,595,967. In yet another, suitable transition metal bleach catalysts comprise a transition metal complex of ligand such as bispidones described in WO 05/042532 A1.

Bleaching agents other than oxygen bleaching agents are also known in the art and can be utilized herein (e.g., photoactivated bleaching agents such as the sulfonated zinc and/or aluminum phthalocyanines (U.S. Pat. No. 4,033,718, incorporated herein by reference)), and/or pre-formed organic peracids, such as peroxycarboxylic acid or salt thereof, and/or peroxysulphonic acids or salts thereof. In one example, a suitable organic peracid comprises phthaloylimidoperoxycaproic acid or salt thereof. When present, the photoactivated bleaching agents, such as sulfonated zinc phthalocyanine, may be present in the filaments of the present invention at a level from about 0.025% to about 1.25% by weight on a dry filament basis.

Brighteners

Any optical brighteners or other brightening or whitening agents known in the art may be incorporated in the filaments of the present invention at levels from about 0.01% to about 1.2% by weight on a dry filament basis. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. Nos. 4,790,856 and 3,646,015.

Fabric Hueing Agents

The filaments of the present invention my include fabric hueing agents. Non-limiting examples of suitable fabric hueing agents include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. In another example, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Non-limiting examples of useful hueing dyes include those found in U.S. Pat. Nos. 7,205,269; 7,208,459; and 7,674,757 B2. For example, fabric hueing dyes may be selected from the group consisting of: triarylmethane blue and violet basic dyes, methine blue and violet basic dyes, anthraquinone blue and violet basic dyes, azo dyes basic blue 16, basic blue 65, basic blue 66 basic blue 67, basic blue 71, basic blue 159, basic violet 19, basic violet 35, basic violet 38, basic violet 48, oxazine dyes, basic blue 3, basic blue 75, basic blue 95, basic blue 122, basic blue 124, basic blue 141, Nile blue A and xanthene dye basic violet 10, an alkoxylated triphenyl-methane polymeric colorant; an alkoxylated thiopene polymeric colorant; thiazolium dye; and mixtures thereof.

In one example, a fabric hueing dye includes the whitening agents found in WO 08/87497 A1. These whitening agents may be characterized by the following structure (I):

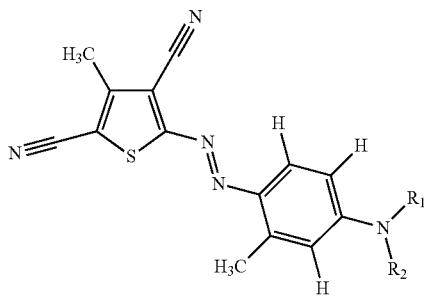

wherein $R_1$ and $R_2$ can independently be selected from:
a) $[(CH_2CR'HO)_x(CH_2CR''HO)_yH]$
   wherein R' is selected from the group consisting of H, $CH_3$, $CH_2$—O—$(CH_2CH_2O)_zH$, and mixtures thereof; wherein R'' is selected from the group consisting of H, $CH_2$—O—$(CH_2CH_2O)_zH$, and mixtures thereof; wherein $x+y \leq 5$; wherein $y \geq 1$; and wherein $z=0$ to 5;
b) $R_1$=alkyl, aryl or aryl alkyl and $R_2$=$[(CH_2CR'HO)_x(CH_2CR''HO)_yH]$
   wherein R' is selected from the group consisting of H, $CH_3$, $CH_2$—O—$(CH_2CH_2O)_zH$, and mixtures thereof; wherein R'' is selected from the group consisting of H, $CH_2$—O—$(CH_2CH_2O)_zH$, and mixtures thereof; wherein $x+y \leq 10$; wherein $y \geq 1$; and wherein $z=0$ to 5;
c) $R_1$=$[CH_2CH_2(OR_3)CH_2OR_4]$ and $R_2$=$[CH_2CH_2(OR_3)CH_2OR_4]$
   wherein $R_3$ is selected from the group consisting of H, $(CH_2CH_2O)_zH$, and mixtures thereof; and wherein $z=0$ to 10;
   wherein $R_4$ is selected from the group consisting of $(C_1\text{-}C_{16})$alkyl, aryl groups, and mixtures thereof; and
d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

In another example, a suitable whitening agent may be characterized by the following structure (II):

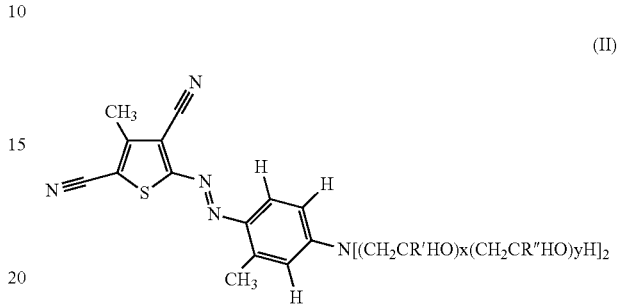

wherein R' is selected from the group consisting of H, $CH_3$, $CH_2$—O—$(CH_2CH_2O)_zH$, and mixtures thereof; wherein R'' is selected from the group consisting of H, $CH_2$—O—$(CH_2CH_2O)_zH$, and mixtures thereof; wherein $x+y \leq 5$; wherein $y \geq 1$; and wherein $z=0$ to 5.

In yet another example, a suitable whitening agent may be characterized by the following structure (III):

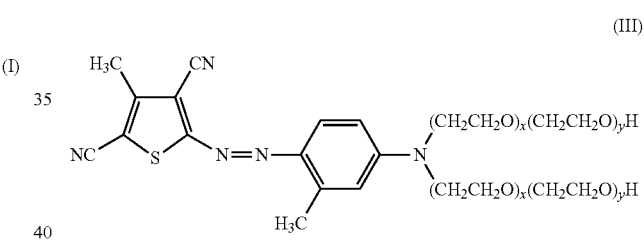

This whitening agent is commonly referred to as "Violet DD". Violet DD is typically a mixture having a total of 5 EO groups. This structure is arrived by the following selection in Structure I of the following pendant groups shown in Table I below in "part a" above:

TABLE I

| | R1 | | | | R2 | | | |
| | R' | R'' | X | y | R' | R'' | x | y |
|---|---|---|---|---|---|---|---|---|
| a | H | H | 3 | 1 | H | H | 0 | 1 |
| b | H | H | 2 | 1 | H | H | 1 | 1 |
| c = b | H | H | 1 | 1 | H | H | 2 | 1 |
| d = a | H | H | 0 | 1 | H | H | 3 | 1 |

Further whitening agents of use include those described in US2008134511A1 (Unilever). In one example, the whitening agent comprises "Violet 13".

Dye Transfer Inhibiting Agents

The filaments of the present invention may include one or more dye transfer inhibiting agents that inhibit transfer of dyes from one fabric to another during a cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% and/or from about 0.01% to about 5% and/or from about 0.05% to about 2% by weight on a dry filament basis.

Chelating Agents

The filaments of the present invention may contain one or more chelating agents, for example one or more iron and/or manganese and/or other metal ion chelating agents. Such chelating agents can be selected from the group consisting of: amino carboxylates, amino phosphonates, polyfunctionally-substituted aromatic chelating agents and mixtures thereof. If utilized, these chelating agents will generally comprise from about 0.1% to about 15% and/or from about 0.1% to about 10% and/or from about 0.1% to about 5% and/or from about 0.1% to about 3% by weight on a dry filament basis.

The chelating agents may be chosen by one skilled in the art to provide for heavy metal (e.g. Fe) sequestration without negatively impacting enzyme stability through the excessive binding of calcium ions. Non-limiting examples of chelating agents of use in the present invention are found in U.S. Pat. Nos. 7,445,644, 7,585,376 and US 2009/0176684A1.

Useful chelating agents include heavy metal chelating agents, such as diethylenetriaminepentaacetic acid (DTPA) and/or a catechol including, but not limited to, Tiron. In embodiments in which a dual chelating agent system is used, the chelating agents may be DTPA and Tiron.

DTPA has the following core molecular structure:

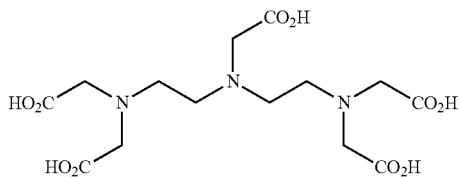

Tiron, also known as 1,2-dihydroxybenzene-3,5-disulfonic acid, is one member of the catechol family and has the core molecular structure shown below:

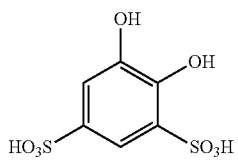

Other sulphonated catechols are of use. In addition to the disulfonic acid, the term "tiron" may also include mono- or di-sulfonate salts of the acid, such as, for example, the disodium sulfonate salt, which shares the same core molecular structure with the disulfonic acid.

Other chelating agents suitable for use herein can be selected from the group consisting of: aminocarboxylates, aminophosphonates, polyfunctionally-substituted aromatic chelating agents and mixtures thereof. In one example, the chelating agents include but are not limited to: HEDP (hydroxyethanedimethylenephosphonic acid); MGDA (methylglycinediacetic acid); and mixtures thereof.

Without intending to be bound by theory, it is believed that the benefit of these materials is due in part to their exceptional ability to remove heavy metal ions from washing solutions by formation of soluble chelates; other benefits include inorganic film or scale prevention. Other suitable chelating agents for use herein are the commercial DEQUEST series, and chelants from Monsanto, DuPont, and Nalco, Inc.

Aminocarboxylates useful as chelating agents include, but are not limited to, ethylenediaminetetracetates, N-(hydroxyethyl)ethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and substituted ammonium salts thereof and mixtures thereof. Aminophosphonates are also suitable for use as chelating agents in the compositions of the invention when at least low levels of total phosphorus are permitted in the filaments of the present invention, and include ethylenediaminetetrakis (methylenephosphonates). In one example, these aminophosphonates do not contain alkyl or alkenyl groups with more than about 6 carbon atoms. Polyfunctionally-substituted aromatic chelating agents are also useful in the compositions herein. See U.S. Pat. No. 3,812,044, issued May 21, 1974, to Connor et al. Non-limiting examples of compounds of this type in acid form are dihydroxydisulfobenzenes such as 1,2-dihydroxy-3,5-disulfobenzene.

In one example, a biodegradable chelating agent comprises ethylenediamine disuccinate ("EDDS"), for example the [S,S] isomer as described in U.S. Pat. No. 4,704,233. The trisodium salt of EDDS may be used. In another example, the magnesium salts of EDDS may also be used.

One or more chelating agents may be present in the filaments of the present invention at a level from about 0.2% to about 0.7% and/or from about 0.3% to about 0.6% by weight on a dry filament basis.

Suds Suppressors

Compounds for reducing or suppressing the formation of suds can be incorporated into the filaments of the present invention. Suds suppression can be of particular importance in the so-called "high concentration cleaning process" as described in U.S. Pat. Nos. 4,489,455 and 4,489,574, and in front-loading-style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols. Suds supressors are described in U.S. Pat. Nos. 2,954,347; 4,265,779; 4,265,779; 3,455,839; 3,933,672; 4,652,392; 4,978,471; 4,983,316; 5,288,431; 4,639,489; 4,749,740; and 4,798,679; 4,075,118; European Patent Application No. 89307851.9; EP 150,872; and DOS 2,124,526.

For any filaments and/or nonwovens comprising such filaments of the present invention designed to be used in automatic laundry washing machines, suds should not form to the extent that they overflow the washing machine. Suds suppressors, when utilized, are preferably present in a "suds suppressing amount." By "suds suppressing amount" is meant that the formulator of the composition can select an amount of this suds controlling agent that will sufficiently control the suds to result in a low-sudsing laundry detergent for use in automatic laundry washing machines.

The filaments herein will generally comprise from 0% to about 10% by weight on a dry filament basis of suds suppressors. When utilized as suds suppressors, for example monocarboxylic fatty acids, and salts therein, may be present in amounts up to about 5% and/or from about 0.5% to about 3% by weight on a dry filament basis. When utilized, silicone suds suppressors are typically used in the filaments at a level up to about 2.0% by weight on a dry filament basis, although higher amounts may be used. When utilized, monostearyl phosphate suds suppressors are typically used in the filaments at a level from about 0.1% to about 2% by weight on a dry filament basis. When utilized, hydrocarbon suds suppressors are typically utilized in the filaments at a level from about 0.01% to about 5.0% by weight on a dry filament basis, although higher levels can be used. When utilized, alcohol suds suppressors are typically used in the filaments at a level from about 0.2% to about 3% by weight on a dry filament basis.

Suds Boosters

If high sudsing is desired, suds boosters such as the $C_{10}$-$C_{16}$ alkanolamides can be incorporated into the filaments, typically at a level from 0% to about 10% and/or from about 1% to about 10% by weight on a dry filament basis. The $C_{10}$-$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgCl_2$, $MgSO_4$, $CaCl_2$, $CaSO_4$ and the like, may be added to the filaments at levels from about 0.1% to about 2% by weight on a dry filament basis to provide additional suds.

Softening Agents

One or more softening agents may be present in the filaments. Non-limiting examples of suitable softening agents include quaternary ammonium compounds for example a quaternary ammonium esterquat compound, silicones such as polysiloxanes, clays such as smectite clays, and mixture thereof.

In one example, the softening agents comprise a fabric softening agent. Non-limiting examples of fabric softening agents include impalpable smectite clays, such as those described in U.S. Pat. No. 4,062,647, as well as other fabric softening clays known in the art. When present, the fabric softening agent may be present in the filaments at a level from about 0.5% to about 10% and/or from about 0.5% to about 5% by weight on a dry filament basis. Fabric softening clays may be used in combination with amine and/or cationic softening agents such as those disclosed in U.S. Pat. Nos. 4,375,416, and 4,291,071. Cationic softening agents may also be used without fabric softening clays.

Conditioning Agents

The filaments of the present invention may include one or more conditioning agents, such as a high melting point fatty compound. The high melting point fatty compound may have a melting point of about 25° C. or greater, and may be selected from the group consisting of: fatty alcohols, fatty acids, fatty alcohol derivatives, fatty acid derivatives, and mixtures thereof. Such fatty compounds that exhibit a low melting point (less than 25° C.) are not intended to be included as a conditioning agent. Non-limiting examples of the high melting point fatty compounds are found in International Cosmetic Ingredient Dictionary, Fifth Edition, 1993, and CTFA Cosmetic Ingredient Handbook, Second Edition, 1992.

One or more high melting point fatty compounds may be included in the filaments of the present invention at a level from about 0.1% to about 40% and/or from about 1% to about 30% and/or from about 1.5% to about 16% and/or from about 1.5% to about 8% by weight on a dry filament basis. The conditioning agents may provide conditioning benefits, such as slippery feel during the application to wet hair and/or fabrics, softness and/or moisturized feel on dry hair and/or fabrics.

The filaments of the present invention may contain a cationic polymer as a conditioning agent. Concentrations of the cationic polymer in the filaments, when present, typically range from about 0.05% to about 3% and/or from about 0.075% to about 2.0% and/or from about 0.1% to about 1.0% by weight on a dry filament basis. Non-limiting examples of suitable cationic polymers may have cationic charge densities of at least 0.5 meq/gm and/or at least 0.9 meq/gm and/or at least 1.2 meq/gm and/or at least 1.5 meq/gm at a pH of from about 3 to about 9 and/or from about 4 to about 8. In one example, cationic polymers suitable as conditioning agents may have cationic charge densities of less than 7 meq/gm and/or less than 5 meq/gm at a pH of from about 3 to about 9 and/or from about 4 to about 8. Herein, "cationic charge density" of a polymer refers to the ratio of the number of positive charges on the polymer to the molecular weight of the polymer. The weight average molecular weight of such suitable cationic polymers will generally be between about 10,000 and 10 million, in one embodiment between about 50,000 and about 5 million, and in another embodiment between about 100,000 and about 3 million.

Suitable cationic polymers for use in the filaments of the present invention may contain cationic nitrogen-containing moieties such as quaternary ammonium and/or cationic protonated amino moieties. Any anionic counterions may be used in association with the cationic polymers so long as the cationic polymers remain soluble in water and so long as the counterions are physically and chemically compatible with the other components of the filaments or do not otherwise unduly impair product performance, stability or aesthetics of the filaments. Non-limiting examples of such counterions include halides (e.g., chloride, fluoride, bromide, iodide), sulfates and methylsulfates.

Non-limiting examples of such cationic polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the filaments of the present invention include cationic polysaccharide polymers, cationic guar gum derivatives, quaternary nitrogen-containing cellulose ethers, cationic synthetic polymers, cationic copolymers of etherified cellulose, guar and starch. When used, the cationic polymers herein are soluble in water. Further, suitable cationic polymers for use in the filaments of the present invention are described in U.S. Pat. Nos. 3,962,418, 3,958,581, and U.S. 2007/0207109A1, which are all incorporated herein by reference.

The filaments of the present invention may include a nonionic polymer as a conditioning agent. Polyalkylene glycols having a molecular weight of more than about 1000 are useful herein. Useful are those having the following general formula:

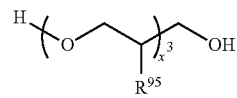

wherein $R^{95}$ is selected from the group consisting of: H, methyl, and mixtures thereof.

Silicones may be included in the filaments as conditioning agents. The silicones useful as conditioning agents typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agents in the filaments may be sufficient to provide the desired conditioning benefits. Such concentration can vary with the conditioning agent, the conditioning performance desired, the average size of the conditioning agent particles, the type and concentration of other components, and other like factors.

The concentration of the silicone conditioning agents typically ranges from about 0.01% to about 10% by weight on a dry filament basis. Non-limiting examples of suitable silicone conditioning agents, and optional suspending agents for the silicone, are described in U.S. Reissue Pat. No. 34,584, U.S. Pat. Nos. 5,104,646; 5,106,609; 4,152,416; 2,826,551; 3,964,500; 4,364,837; 6,607,717; 6,482,969; 5,807,956; 5,981,681; 6,207,782; 7,465,439; 7,041,767; 7,217,777; U.S. Patent Application Nos. 2007/0286837A1; 2005/0048549A1; 2007/0041929A1; British Pat. No. 849,433; German Patent No. DE 10036533, which are all incorporated herein by reference; Chemistry and Technology of Silicones, New York: Academic Press (1968); General Electric Silicone Rubber Product Data Sheets SE 30, SE 33, SE 54 and SE 76; Silicon Compounds, Petrarch Systems, Inc. (1984); and in Encyclopedia of Polymer Science and Engineering, vol. 15, 2d ed., pp 204-308, John Wiley & Sons, Inc. (1989).

In one example, the filaments of the present invention may also comprise from about 0.05% to about 3% by weight on a dry filament basis of at least one organic conditioning oil as a conditioning agent, either alone or in combination with other conditioning agents, such as the silicones (described herein). Suitable conditioning oils include hydrocarbon oils, polyolefins, and fatty esters. Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217,914, 4,381,919, and 4,422,853, which are all incorporated herein by reference.

Humectants

The filaments of the present invention may contain one or more humectants. The humectants herein are selected from the group consisting of polyhydric alcohols, water soluble alkoxylated nonionic polymers, and mixtures thereof. The humectants, when used, may be present in the filaments at a level from about 0.1% to about 20% and/or from about 0.5% to about 5% by weight on a dry filament basis.

Suspending Agents

The filaments of the present invention may further comprise a suspending agent at concentrations effective for suspending water-insoluble material in dispersed form in the compositions or for modifying the viscosity of the composition. Such concentrations of suspending agents range from about 0.1% to about 10% and/or from about 0.3% to about 5.0% by weight on a dry filament basis.

Non-limiting examples of suitable suspending agents include anionic polymers and nonionic polymers (e.g., vinyl polymers, acyl derivatives, long chain amine oxides, and mixtures thereof, alkanol amides of fatty acids, long chain esters of long chain alkanol amides, glyceryl esters, primary amines having a fatty alkyl moiety having at least about 16 carbon atoms, secondary amines having two fatty alkyl moieties each having at least about 12 carbon atoms). Examples of suspending agents are described in U.S. Pat. No. 4,741,855.

Enzymes

One or more enzymes may be present in the filaments of the present invention. Non-limiting examples of suitable enzymes include proteases, amylases, lipases, cellulases, carbohydrases including mannanases and endoglucanases, pectinases, hemicellulases, peroxidases, xylanases, phopholipases, esterases, cutinases, keratanases, reductases, oxidases, phenoloxidases, lipoxygenases, ligninases, pullulanases, tannases, penosanases, malanases, glucanases, arabinosidases, hyaluraonidases, chrondroitinases, laccases, and mixtures thereof.

Enzymes may be included in the filaments of the present invention for a variety of purposes, including but not limited to removal of protein-based, carbohydrate-based, or triglyceride-based stains from substrates, for the prevention of refugee dye transfer in fabric laundering, and for fabric restoration. In one example, the filaments of the present invention may include proteases, amylases, lipases, cellulases, peroxidases, and mixtures thereof of any suitable origin, such as vegetable, animal, bacterial, fungal and yeast origin. Selections of the enzymes utilized are influenced by factors such as pH-activity and/or stability optima, thermostability, and stability to other additives, such as active agents, for example builders, present within the filaments. In one example, the enzyme is selected from the group consisting of: bacterial enzymes (for example bacterial amylases and/or bacterial proteases), fungal enzymes (for example fungal cellulases), and mixtures thereof.

When present in the filaments of the present invention, the enzymes may be present at levels sufficient to provide a "cleaning-effective amount". The term "cleaning effective amount" refers to any amount capable of producing a cleaning, stain removal, soil removal, whitening, deodorizing, or freshness improving effect on substrates such as fabrics, dishware and the like. In practical terms for current commercial preparations, typical amounts are up to about 5 mg by weight, more typically 0.01 mg to 3 mg, of active enzyme per gram of the filament and/or fiber of the present invention. Stated otherwise, the filaments of the present invention will typically comprise from about 0.001% to about 5% and/or from about 0.01% to about 3% and/or from about 0.01% to about 1% by weight on a dry filament basis.

One or more enzymes may be applied to the filament and/or nonwoven web and/or film after the filament and/or nonwoven web and/or film are produced.

A range of enzyme materials and means for their incorporation into the filament-forming composition of the present invention, which may be a synthetic detergent composition, is also disclosed in WO 9307263 A; WO 9307260 A; WO 8908694 A; U.S. Pat. Nos. 3,553,139; 4,101,457; and 4,507,219.

Enzyme Stabilizing System

When enzymes are present in the filaments and/or fibers of the present invention, an enzyme stabilizing system may also be included in the filaments. Enzymes may be stabilized by various techniques. Non-limiting examples of enzyme stabilization techniques are disclosed and exemplified in U.S. Pat. Nos. 3,600,319 and 3,519,570; EP 199,405, EP 200,586; and WO 9401532 A.

In one example, the enzyme stabilizing system may comprise calcium and/or magnesium ions.

The enzyme stabilizing system may be present in the filaments of the present invention at a level of from about 0.001% to about 10% and/or from about 0.005% to about 8% and/or from about 0.01% to about 6% by weight on a dry filament basis. The enzyme stabilizing system can be any stabilizing system which is compatible with the enzymes present in the filaments. Such an enzyme stabilizing system may be inherently provided by other formulation actives, or be added separately, e.g., by the formulator or by a manufacturer of enzymes. Such enzyme stabilizing systems may, for example, comprise calcium ion, magnesium ion, boric acid, propylene glycol, short chain carboxylic acids, boronic acids, and mixtures thereof, and are designed to address different stabilization problems.

Builders

The filaments of the present invention may comprise one or more builders. Non-limiting examples of suitable builders include zeolite builders, aluminosilicate builders, silicate builders, phosphate builders, citric acid, citrates, nitrilo triacetic acid, nitrilo triacetate, polyacrylates, acrylate/maleate copolymers, and mixtures thereof.

In one example, a builder selected from the group consisting of: aluminosilicates, silicates, and mixtures thereof, may be included in the filaments of the present invention. The builders may be included in the filaments to assist in controlling mineral, especially calcium and/or magnesium hardness in wash water or to assist in the removal of particulate soils from surfaces. Also suitable for use herein are synthesized crystalline ion exchange materials or hydrates thereof having chain structure and a composition represented by the following general Formula I an anhydride form: $x(M_2O).ySiO_2.zM'O$ wherein M is Na and/or K, M' is Ca and/or Mg; y/x is 0.5 to 2.0 and z/x is 0.005 to 1.0 as taught in U.S. Pat. No. 5,427,711.

Non-limiting examples of other suitable builders that may be included in the filaments include phosphates and polyphosphates, for example the sodium salts thereof; carbonates, bicarbonates, sesquicarbonates and carbonate minerals other than sodium carbonate or sesquicarbonate; organic mono-, di-, tri-, and tetracarboxylates for example water-soluble non-surfactant carboxylates in acid, sodium, potassium or alkanolammonium salt form, as well as oligomeric or water-soluble low molecular weight polymer carboxylates including aliphatic and aromatic types; and phytic acid. These builders may be complemented by borates, e.g., for pH-buffering purposes, or by sulfates, for example sodium sulfate and any other fillers or carriers which may be important to the engineering of stable surfactant and/or builder-containing filaments of the present invention.

Still other builders may be selected from polycarboxylates, for example copolymers of acrylic acid, copolymers of acrylic acid and maleic acid, and copolymers of acrylic acid and/or maleic acid and other suitable ethylenic monomers with various types of additional functionalities.

Builder level can vary widely depending upon end use. In one example, the filaments of the present invention may comprise at least 1% and/or from about 1% to about 30% and/or from about 1% to about 20% and/or from about 1% to about 10% and/or from about 2% to about 5% by weight on a dry fiber basis of one or more builders.

Clay Soil Removal/Anti-Redeposition Agents

The filaments of the present invention may contain water-soluble ethoxylated amines having clay soil removal and anti-redeposition properties. Such water-soluble ethoxylated amines may be present in the filaments of the present invention at a level of from about 0.01% to about 10.0% and/or from about 0.01% to about 7% and/or from about 0.1% to about 5% by weight on a dry filament basis of one or more water-soluble ethoxylates amines. Non-limiting examples of suitable clay soil removal and antiredeposition agents are described in U.S. Pat. Nos. 4,597,898; 548,744; 4,891,160; European Patent Application Nos. 111,965; 111,984; 112, 592; and WO 95/32272.

Polymeric Soil Release Agent

The filaments of the present invention may contain polymeric soil release agents, hereinafter "SRAs." If utilized, SRA's will generally comprise from about 0.01% to about 10.0% and/or from about 0.1% to about 5% and/or from about 0.2% to about 3.0% by weight on a dry filament basis.

SRAs typically have hydrophilic segments to hydrophilize the surface of hydrophobic fibers such as polyester and nylon, and hydrophobic segments to deposit upon hydrophobic fibers and remain adhered thereto through completion of washing and rinsing cycles thereby serving as an anchor for the hydrophilic segments. This can enable stains occurring subsequent to treatment with SRA to be more easily cleaned in later washing procedures.

SRAs can include, for example, a variety of charged, e.g., anionic or even cationic (see U.S. Pat. No. 4,956,447), as well as non-charged monomer units and structures may be linear, branched or even star-shaped. They may include capping moieties which are especially effective in controlling molecular weight or altering the physical or surface-active properties. Structures and charge distributions may be tailored for application to different fiber or textile types and for varied detergent or detergent additive products. Non-limiting examples of SRAs are described in U.S. Pat. Nos. 4,968,451; 4,711,730; 4,721,580; 4,702,857; 4,877,896; 3,959,230; 3,893,929; 4,000,093; 5,415,807; 4,201,824; 4,240,918; 4,525,524; 4,201,824; 4,579,681; and 4,787,989; European Patent Application 0 219 048; 279,134 A; 457,205 A; and DE 2,335,044.

Polymeric Dispersing Agents

Polymeric dispersing agents can advantageously be utilized in the filaments of the present invention at levels from about 0.1% to about 7% and/or from about 0.1% to about 5% and/or from about 0.5% to about 4% by weight on a dry filament basis, especially in the presence of zeolite and/or layered silicate builders. Suitable polymeric dispersing agents may include polymeric polycarboxylates and polyethylene glycols, although others known in the art can also be used. For example, a wide variety of modified or unmodified polyacrylates, polyacrylate/mealeates, or polyacrylate/methacrylates are highly useful. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition. Non-limiting examples of polymeric dispersing agents are found in U.S. Pat. No. 3,308,067, European Patent Application No. 66915, EP 193,360, and EP 193,360.

Alkoxylated Polyamine Polymers

Alkoxylated polyamines may be included in the filaments of the present invention for providing soil suspending, grease cleaning, and/or particulate cleaning. Such alkoxylated polyamines include but are not limited to ethoxylated polyethyleneimines, ethoxylated hexamethylene diamines, and sulfated versions thereof. Polypropoxylated derivatives of polyamines may also be included in the filaments of the present invention. A wide variety of amines and polyaklyeneimines can be alkoxylated to various degrees, and optionally further modified to provide the abovementioned benefits. A useful example is 600 g/mol polyethyleneimine core ethoxylated to 20 EO groups per NH and is available from BASF.

Alkoxylated Polycarboxylate Polymers

Alkoxylated polycarboxylates such as those prepared from polyacrylates may be included in the filaments of the present invention to provide additional grease removal performance. Such materials are described in WO 91/08281 and PCT 90/01815. Chemically, these materials comprise polyacrylates having one ethoxy side-chain per every 7-8 acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10% by weight on a dry filament basis.

Amphilic Graft Co-Polymers

The filaments of the present invention may include one or more amphilic graft co-polymers. An example of a suitable amphilic graft co-polymer comprises (i) a polyethyelene glycol backbone; and (ii) and at least one pendant moiety selected from polyvinyl acetate, polyvinyl alcohol and mixtures thereof. A non-limiting example of a commercially available amphilic graft co-polymer is Sokalan HP22, supplied from BASF.

Dissolution Aids

The filaments of the present invention may incorporate dissolution aids to accelerate dissolution when the filament contains more the 40% surfactant to mitigate formation of insoluble or poorly soluble surfactant aggregates that can sometimes form or surfactant compositions are used in cold water. Non-limiting examples of dissolution aids include sodium chloride, sodium sulfate, potassium chloride, potassium sulfate, magnesium chloride, and magnesium sulfate.

Ingestible Active Agents

The filaments of the present invention may comprise one or more ingestible active agents. In one example, the ingestible active agents may comprise one or more health care active agents.

Health Care Active Agents

In one example, one or more health care actives (health care active agents) may be uniformly distributed or substantially uniformly distributed throughout the filament. In another example, one or more health care actives may be distributed as discrete regions within the filament. In still another example, at least one health care active is distributed uniformly or substantially uniformly throughout the filament and at least another health care active is distributed as one or more discrete regions within the filament. In still yet another example, at least one health care active is distributed as one or more discrete regions within the filament and at least another health care active is distributed as one or more discrete regions different from the first discrete regions within the filament.

The one or more health care actives can include respiratory agents, gastrointestinal agents, central nervous system (CNS) agents, anti-infective agents, nutritional agents, overall wellbeing agents and combinations thereof. The one or more health care actives of the present invention can also be selected from the group consisting of delayed delivery health care actives, extended delivery health care actives, immediate delivery health care actives, targeted delivery health care actives, and combinations thereof. In one example, one or more health care actives are encapsulated. In one example the health care active is selected from the group consisting of dextromethorphan, fexofenadine, famotidine, naproxen, vitamin $B_9$, and combinations thereof.

The personal health care articles of the present invention may also treat one or more health conditions. Non-limiting examples of health conditions can include respiratory conditions, gastrointestinal conditions, CNS conditions, pathogenic infections, nutritional deficiencies, and combinations thereof.

The personal health care articles of the present invention may also provide one or more health benefits. Non-limiting examples of health benefits can include respiratory benefits, gastrointestinal benefits, CNS benefits, anti-infection benefits, nutritional benefits, overall wellbeing benefits, and combinations thereof.

In one example, the health care actives wherein the health care actives comprise particles. The particles of the health care article are less than about 1 µm, in another example the particles are less than about 750 nanometers (nm), in a different example less than about 500 nm, in yet another example less than about 250 nm, in another example less than about 100 nm, in yet another example less than about 50 nm, in another example less than about 25 nm, in another example less than about 10 nm, in another example less than about 5 nm, and in yet another example less than about 1 nm.

All health care actives may be present from about 10% to about 90%, by weight on a dry filament basis, in another example from about 15% to about 80%, by weight on a dry filament basis, in a different example from about 20% to about 75%, by weight on a dry filament basis, in another example from about 25% to about 70%, by weight on a dry filament basis, in a different example from about 30% to about 60%, by weight on a dry filament basis, and in another example from about 35% to about 60%, by weight on a dry filament basis. In another example, the filament comprises greater than about 10%, by weight on a dry filament basis, health care actives, in yet another example greater than about 15%, by weight on a dry filament basis, health care actives, in another example, greater than about 25%, by weight on a dry filament basis, health care actives, in still another example greater than 35%, by weight on a dry filament basis, health care actives, in another example greater than about 40%, by weight on a dry filament basis, health care actives, in another example greater than about 45%, by weight on a dry filament basis, health care actives, an in yet another example greater than about 50%, by weight on a dry filament basis, health care actives.

Respiratory Agents

In an example one or more health care actives can be a respiratory agent. Non-limiting examples of respiratory agents can include nasal decongestants, mucolytics, expectorants, antihistamines, non-narcotic antitussives, demulcents, anesthetics, plant-derived respiratory agents, and combinations thereof. Respiratory agents may be used to treat respiratory conditions. Non-limiting examples of respiratory conditions can include influenza, the common cold, pneumonia, bronchitis, and other viral infections; pneumonia, bronchitis, and other bacterial infections; allergies; sinusitis; rhinitis; and combinations thereof. Respiratory agents may provide a respiratory benefit. Non-limiting examples of respiratory benefits can include treating, respiratory symptoms. Non-limiting examples of respiratory symptoms include nasal congestion, chest congestion, rhinorrhea, coughing, sneezing, headache, body aches, fever, fatigue or malaise, sore throat, difficulty breathing, sinus pressure, sinus pain, and combinations thereof.

Non-limiting examples of decongestants can include phenylephrine, 1-desoxyephedrine, ephedrine, propylhexedrine, pseudoephedrine, phenylpropanolamine, and combinations thereof.

Non-limiting mucolytics can include ambroxol, bromhexine, N-acetylcysteine, and combinations thereof.

Non-limiting expectorants can include guaifenesin, terpin hydrate, and combinations thereof.

Non-limiting examples of antihistamines can include chlorpheniramine, diphenhydramine, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenhydramine, tranilast, carbinoxamine, traxanox, chlorphenoxamine, diphenylpyaline, embramine, p-methyldiphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine, and combinations thereof. In one example, the health care active can be fexofenadine.

Non-limiting examples of antitussives can include benzonatate, chlophedianol, dextromethorphan, levodropropizine, and combinations thereof. In one example the health care active can be dextromethorphan.

Non-limiting examples of demulcents can include glycerin, honey, pectin, gelatin, liquid sugar, and combinations thereof.

Non-limiting examples of anesthetics can include menthol, phenol, benzocaine, lidocaine, hexylresorcinol, and combinations thereof.

Non-limiting examples of plant-derived respiratory agents can include andrographis (*Andrographis paniculata*), garlic (*Allium sativum* L.), *Eleutherococcus senticosus*, a guaiacol component (from oils of cassia (*Cinnamomum aromaticum*), clove (*Syzygium aromaticum, Eugenia aromaticum, Eugenia caryophyllata*), or cinnamon (*Cinnamomum zeylanicum, Cinnamomum verum, Cinnamomum loureiroi, Cinnamomum camphora, Cinnamomum tamala, Cinnamomum burmannii*)), borage seed oil (*Borago officinalis*), sage (*Salvia officinalis, Salvia lavandulaefolia, Salvia lavandulifolia*), astragalus (*Astragalus membraneceus*), boneset (*Eupatorium perfoliatum*), chamomile (*Matricaria recutita, Chamaemelum nobile*), cordyceps (*Cordyceps sinensis*), echinacea (*Echinacea angustifolia* DC, *Echinacea pallida, Echinacea purpurea*), elder (*Sambucus nigra* L.), euphorbia, ginseng (American ginseng, Asian ginseng, Chinese ginseng, Korean red ginseng, *Panax ginseng: Panax* ssp. Including *P. ginseng* C.C. Meyer, and *P. quinquefolius* L.), goldenseal (*Hydrastis canadensis* L.), greater celandine (*Chelidonium majus*), horseradish (*Armoracia rusticana, Cochlearia armoracia*), maitake mushrooms (*Grifola frondosa*) mistletoe (*Visvum album* L.), geranium (*Pelargonium sidoides*), peppermint/peppermint oil (*Menthaxpeperita* L.), propolis, slippery elm (*Ulmus rubra* Muhl, *Ulmus fulva* Michx), Sorrel (*Rumex acetosa* L., *Rumex acetosella* L.), thyme/thymus extract (*Thymus vulgaris* L.), wild indigo (*Baptisia australis*), quercetin (a flavanol), and combinations thereof.

Gastrointestinal Agents

In one example the one or more health care actives can be a gastrointestinal agent. Non-limiting examples of gastrointestinal agents can include anti-diarrheals, lower gastrointestinal agents, laxatives, anti-emetics, antacids, anti-flattulents, $H_2$ receptor antagonists, proton pump inhibitors, lipase inhibitors, rafting agents, probiotics, prebiotics, dietary fiber, enzymes, plant-derived gastrointestinal agents, anesthetics, and combinations thereof. Gastrointestinal agents may be used to treat gastrointestinal conditions. Non-limiting examples of gastrointestinal conditions can include, gastroesophogeal reflux disease, gastritis, peptic ulcers, dyspepsia, irritable bowel syndrome, colitis, Crohn's disease, Barrett's esophagus, gastrinoma, diarrhea, indigestion, constipation, obesity, pouchitis, diverticulitis, enteritis, enterocolitis, dysphagia, inflamed hemorrhoids, food poisoning and other bacterial infections, influenza and other viral infections, and combinations thereof. Gastrointestinal agents may provide gastrointestinal benefits. Non-limiting examples of gastrointestinal benefits can include restoring digestive balance, treating gastrointestinal symptoms, and combinations thereof. Non-limiting examples of gastrointestinal symptoms can include diarrhea, constipation, upset stomach, vomiting, sour stomach, cramps, gas, bloating, stomach ache, sore throat, difficulty swallowing, unintentional weight loss, visceral hypersensitivity, feeling of fullness, indigestion, nausea, heartburn, urgency to have a bowel movement, lack of appetite, regurgitation, belching, flatulence, blood in stool, dehydration, and combinations thereof.

Non-limiting examples of anti-diarrheals can include loperamide, pharmaceutically acceptable salts of bismuth, attapulgite, activated charcoal, bentonite, and combinations thereof.

Non-limiting examples of lower gastrointestingal agents can include mesalamine, olsalazine sodium, balsalazide disodium, sulfasalazine, tegaserod maleate, and combinations thereof.

Non-limiting examples of laxatives can include bisacodyl, cascara sagrada, castor oil, dietary fiber, resistant starch, resistant maltodextrin, docusate calcium, docusate sodium, lactulose, sennosides, mineral oil, polyethylene glycol 400, polyethylene glycol 3350, and combinations thereof.

Non-limiting examples of anti-emetics can include cyclizine, meclizine, buclizine, dimenhydrinate, scopolamine, trimethobenzamide, dronabinol, 5-$HT_3$ receptor antagonists, aprepitant, and combinations thereof.

Non-limiting examples of antacids can include sodium bicarbonate, sodium carbonate, calcium carbonate, magnesium carbonate, magnesium hydroxide, aluminum hydroxide, magaldrate, and combinations thereof.

Non-limiting examples of anti-flatulents can include simethicone.

Non-limiting examples of $H_2$ receptor antagonists can include famotidine, ranitidine, cimetidine, nizatidine, and combinations thereof. In one example, the health care active can be famotidine.

Non-limiting examples of proton pump inhibitors can include omeprazole, lansoprazole, esomeprazole, pantoprazole, rabeprazole, and combinations thereof.

Non-limiting examples of lipase inhibitors can include orlistat.

The filament of the present invention may comprise rafting agents. Non-limiting examples of rafting agents can include alginates, fenugreek, guar gum, xanthan gum, carrageenan, and combinations thereof.

The filament of the present invention may comprise probiotics. Non-limiting examples of probiotics can include microorganisms of the genera *Bacillus, Bacteroides, Bifidobacterium, Enterococcus* (e.g., *Enterococcus faecium*), *Lactobacillus, Leuconostoc, Saccharomyces*, and combinations thereof. In another example of the invention, the probiotic is selected from bacteria of the genera *Bifidobacterium, Lactobacillus*, and combinations thereof.

Non-limiting examples of microorganisms can include strains of *Streptococcus lactis, Streptococcus cremoris, Streptococcus diacetylactis, Streptococcus thermophilus, Lactobacillus bulgaricus, Lactobacillus acidophilus* (e.g., *Lactobacillus acidophilus* strain), *Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Bifidobacterium longum, Bifidobacterium infantis, Bifidobacterium bifidum, Bifidobacterium animalis, Bifidobacterium pseudolongum, Saccharomyces boulardii, Pediococcus cerevisiae, Lactobacillus salivarius, Bacillus coagulans*, and combinations thereof.

Non-limiting examples of prebiotics can include carob bean, citrus pectin, rice bran, locust bean, fructooligosaccharide, oligofructose, galactooligosaccharide, citrus pulp, mannanoligosaccharides, arabinogalactan, lactosucrose, glucomannan, polydextrose, apple pomace, tomato pomace, carrot pomace, *cassia* gum, gum karaya, gum talha, gum arabic, and combinations thereof.

Non-limiting examples of dietary fibers can include, but are not limited to inulin, agar, beta-glucans, chitins, dextrins, lignin, cellulose, modified cellulose, cellulose ethers, hemicelluloses, non-starch polysaccharides, reduced starch, polycarbophil, partially hydrolyzed guar gum, wheat dextrin, and combinations thereof.

In one example, the dietary fiber comprises glucose polymers, preferably those which have branched chains. Among such suitable dietary fibers is one marketed under the tradename "Fibersol2", commercially available from Matsutani Chemical Industry Co., Itami City, Hyogo, Japan.

Other non-limiting examples of suitable dietary fibers can include oligosaccharides, such as inulin and its hydrolysis products commonly known as fructooligosaccharides, galacto-oligosaccharides, xylo-oligosaccharides, oligo derivatives of starch, and combinations thereof.

The dietary fiber can be provided in any suitable form. A non-limiting example is in the form of a plant material which contains the fiber. Non-limiting examples of suitable plant materials can include asparagus, artichoke, onion, wheat, chicory, beet pulp, residues of these plant materials, and combinations thereof.

A non-limiting example of a dietary fiber from such a plant material is inulin extract from extract of chicory. Suitable inulin extracts can be obtained from Orafti SA of Belgium under the trademark Raftiline®. Alternatively the dietary fiber can be in the form of a fructo-oligosaccharide which can be obtained from Orafti SA of Belgium under the trademark Raftilose®. Alternatively, an oliogo-saccharide can be obtained by hydrolyzing inulin, by enzymatic methods, or by using microorganisms as will be understood by those of skill in the art. Alternatively the dietary fiber can be inulin and/or de-sugared inulin available from Cargill Health & Food Technologies, Wayzata, Minn., USA, or from Cosucra SA, Warcoing, Belgium.

In another example, the dietary fiber can be psyllium, available, which can be obtained from The Procter & Gamble Company, Cincinnati, Ohio, under the trademark Metamucil®.

The filament of the present invention can comprise enzymes which can include purified enzymes, partially purified enzymes, extracts containing enzymes, and combinations thereof. Enzymes can be produced synthetically, through genetic modification, or they can be produced naturally by plants, animals, or microorganisms. In some examples the enzymes are produced by plants such as peppermint, pineapple, or papaya. In other examples the enzymes are produced by fungi such as *Aspergillus, Candida, Saccharomyces*, and *Rhizopus*. In another example the enzymes are produced by an animal such as a pig or bovine. In certain examples, the enzymes help support a more complete digestion of food for gastrointestinal health, regularity, and normal bowel function. In other examples, the enzymes can provide wellness benefits or health benefits.

Non-limiting examples of enzymes can include, but are not limited to, proteases, amylases, lipases, and combinations thereof.

Other non-limiting examples of enzymes can include bromelain, pepsin, papain, amyloglucosidase, glucoamylase, malt diastase, maltase, lactase, $\alpha$-galactosidase, $\beta$-glucanase, cellusase, hemilase, hemicellulase, cellulase, xylanase, invertase, pectinase, pancreatin, rennet, phytase, pancrelipase, and combinations thereof.

Non-limiting examples of plant-derived gastrointestinal agents can include materials from the Ginger family (Zigiberaceae), licorice root (*Glycyrrhizin glabra*), marshmallow root (*Althea officinalis, Althea radix*), fennel oil, fennel seed (*Foeniculum vulgare*), caraway oil, caraway seed (*Carum carvi, Carvi fructus, Carvi aetheroleum*), lemon balm (*Melissae folium*, Melissa), horehound herb (*Murrubii herba*), and flaxseed alpha-linoleic acid (*Lini semen*).

Central Nervous System Agents

In one example the one or more health care actives can be a central nervous system (CNS) agent. Non-limiting examples of CNS agents can include sleep aids, nonsteroidal anti-inflammatory drugs, salicylates, opioid analgesics, miscellaneous central nervous system stimulants, anti-emetics, and combinations thereof. Anti-emetics are described herein. CNS agents may be used to treat CNS conditions. Non-limiting examples of CNS conditions can include insomnia, restless leg syndrome, narcolepsy, pain, tobacco dependence, depression, attention deficit disorder, attention deficit hyperactivity disorder, and combinations thereof. Non-limiting examples of pain can include headaches, migraines, arthritis, post-operative pain, dental pain, and combinations thereof. CNS agents may provide CNS benefits. Non-limiting examples of CNS benefits can include increasing alertness, restoring normal circadian rhythm, treating CNS symptoms, and combinations thereof. Non-limiting examples of CNS symptoms can include insomnia, abnormal circadian rhythm, pain, inflammation, fatigue, drowsiness, difficulty concentrating, irritation, vomiting, nausea, and combinations thereof.

The filament of the present invention can comprise sleep aids. Non-limiting examples of sleep aids can include aolpidem, eszopiclone, zaleplon, doxepin, doxylamine, melatonin, ramelteon, estazolam, flurazepam hydrochloride, quazepam, temazepam, triazolam, and combinations thereof.

Non-limiting examples of nonsteroidal anti-inflammatory drugs (NSAIDs) can include acetaminophen, celecoxib, diclofenac, etodolac, fenoprofen calcium, ibuprofen, ketoprofen, mefenamic acid, meloxicam, naproxen, tolmetin sodium, indomethacin, and combinations thereof. In one example, the health care active can be naproxen.

Non-limiting examples of salicylates can include aspirin, magnesium salicylate, salsalate, diflunisal, and combinations thereof.

Non-limiting examples of opioid analgesics can include codeine, hydromorphone hydrochloride, methadone hydrochloride, morphine sulfate, oxycodone hydrochloride, and combinations thereof.

The filament of the present invention can comprise miscellaneous central nervous system stimulants. Non-limiting examples of miscellaneous CNS stimulants can include nicotine, picrotoxin, pentylenetetrazol, and combinations thereof.

Anti-Infective Agents

In one example the one or more health care actives can be an anti-infective agent. Non-limiting examples of anti-infective agents can include antivirals, antimicrobials, and combinations thereof. Anti-infective agents can be used to treat pathogenic infections. Non-limiting examples of pathogenic infections can include tuberculosis, pneumonia, food poisoning, tetanus, typhoid fever, diphtheria, syphilis, meningitis, sepsis, leprosy, whooping cough, lyme disease, gangrene, urinary tract infections, traveler's diarrhea, methicillin-resistant *Staphylococcus aureus* (MRSA), gonorrhea, scarlet fever, cholera, herpes, hepatitis, human immunodeficiency virus (HIV), influenza, measles, mumps, human papillomavirus, polio virus, *giardia*, malaria, tapeworm, roundworm, and combinations thereof. Anti-infective agents may provide anti-infective benefits. Non-limiting examples of anti-infective benefits can include treat pathogenic infection symptoms. Non-limiting examples of pathogenic infection symptoms can include fever, inflammation, nausea, vomiting, loss of appetite, abnormal white blood cell count, diarrhea, rash, skin lesions, sore throat, headache, stomach ache, muscle pain, fatigue, cough, chest pain, difficulty breathing, burning during urination, and combinations thereof.

Non-limiting examples of antivirals can include ganciclovir, valganciclovir, acyclovir, famciclovir, valacyclovir, amantadine, ribavirin, rimantidine HCl, oseltamivir phosphate, adefovir dipivoxil, entecavir, and combinations thereof.

Non-limiting examples of antimicrobials can include nitroimidazole antibiotics, tetracyclines, penicillin-based antibiotics such as amoxicillin, cephalosporins, carbopenems, aminoglycosides, macrolide antibiotics, lincosamide antibiotics, 4-quinolones, fluoroquinolones, rifamycins, rifaximi, macrolides, nitrofurantoin, and combinations thereof.

Nutritional Agents

In one example the one or more health care actives can be a nutritional agent. Non-limiting examples of nutritional agents can include vitamins, minerals and electrolytes, dietary fiber, fatty acids, and combinations thereof. Nutritional agents can be used to treat nutritional deficiencies. Non-limiting examples of nutritional deficiencies can include a depressed immune system, birth defects in newborns, heart disease, cancer, Alzheimer's disease, eye diseases, nightblindness, osteoporosis, beriberi, pellagra, scurvy, rickets, alcoholism, irritable bowel syndrome (IBS), low hormone levels, hypertension, and combinations thereof. Nutritional agents may provide a nutritional benefit. Non-limiting examples of nutritional benefits can include disease prevention, lowering cholesterol, increased energy and alertness, preventing aging, restoring digestive balance, and treat nutritional deficiency symptoms and combinations thereof. Non-limiting examples of nutritional deficiency symptoms can include fatigue, muscle weakness, irritability, hair loss, unintentional weight loss, unintentional weight gain, slow wound healing, decreased mental ability, stress, bone fractures, decreased eyesight, decreased rate of wound healing, hyperactivity, dermatitis, muscle cramping, cardiac arrhythmias, depression, and combinations thereof.

Non-limiting examples of vitamins can include vitamin C, vitamin $D_2$ (cholecalciferol), vitamin $D_3$ (ergocalciferol), vitamin A, vitamin $B_1$ (thiamine), vitamin $B_2$ (riboflavin), vitamin $B_3$ (niacin), $B_5$ (pantothenic acid), vitamin $B_6$ (pyridoxine, pyridoxal, or pyridoxamine), vitamin $B_7$ (biotin), vitamin $B_9$ (folic acid), Vitamin $B_{12}$ (cyanocobalmin), vitamin E, and combinations thereof. In one example, the health care active can be vitamin $B_9$.

Non-limiting examples of minerals and electrolytes can include zinc, iron, calcium, iodine, copper, magnesium, potassium, chromium, selenium, and combinations thereof.

Non-limiting examples of antioxidants can include, but are not limited to, polyphenols, superfruits, and combinations thereof.

Non-limiting examples of health care actives containing polyphenols can include tea extract, coffee extract, turmeric extract, grapeseed extract, blueberry extract, and combinations thereof. Nonlimiting examples of superfruits can include açai, blueberry, cranberry, grape, guarana, mangosteen, noni, pomegranate, seabuckthorn, wolfberry (goji), acerola (Barbados cherry, *Malpighia emarginate, Malpighia glabra*), bayberry (yumberry, *Myrica rubra*), bilberry (*Vaccinium myrtillus*), black raspberry (*Rubus occidentalis*), black chokeberry ("aronia", *Aronia melanocarpa*), blackcurrant (*Ribes nigrum*), camu camu (*Myrciaria dubia*), sour (tart) cherry (*Prunus cerasus*), cupuaçu (*Theobroma grandiflorum*), durian (*Durio kutejensis*), elderberry (*Sambucus canadensis, Sambucus nigra*), red guava (*Psidium guajava*, many species), Indian gooseberry (amalaka, amla, *Phyllanthus emblica*), kiwifruit (*Actinidia deliciosa*), lingonberry (*Vaccinium vitis-idaea*), lychee (*Litchi chinensis*), muscadine grape (*Vitis rotundifolia*), papaya (*Carica papaya*), pomelo (*Citrus maxima*), saskatoon berry (*Amelanchier alnifolia*, Nutt), tamarind (*Tamarindus indica*), wild cherry (*Prunus avium*) and yuzu (*Citrus ichangensis, C. reticulata*) and combinations thereof.

Non-limiting examples of fatty acids can include Omega-3 fatty acids, Omega-6 fatty acids, and combinations thereof.

Non-limiting examples of Omega-3 fatty acids can include alpha-linolenic acid, alpha-linolenic acid, stearidonic acid, eicosatrienoic acid, eicosatetraenoic acid, eicosapentaenoic acid, docosapentaenoic acid, docosahexaenoic acid, tetracosapentaenoic acid, tetracosahexaenoic acid, and combinations thereof.

Non-limiting examples of Omega-6 fatty acids can include linoleic acid, gamma-linolenic acid, eicosadienoic acid, dihomo-gamma-linolenic acid, arachidonic acid, docosadienoic acid, adrenic acid, docosapentaenoic acid, and combinations thereof.

Overall Wellbeing Agents

In one example the one or more health care actives can be an overall wellbeing agent. Non-limiting examples of overall wellbeing agents can include energy boosting agents, probiotics, prebiotics, dietary fiber, enzymes, vitamins, minerals and electrolytes, antioxidants, fatty acids, and combinations thereof. Probiotics, prebiotics, dietary fiber, enzymes, vitamins, minerals and electrolyntes, antioxidants, and fatty acids are described herein.

Overall wellbeing agents can be used to provide one or more overall wellbeing benefits. Non-limiting examples of overall wellbeing benefits can include improving and/or maintaining respiratory health, gastrointestinal health, immune health, mobility and joint health, cardiovascular health, skin health, oral/dental health, hair health, eye health, reproductive health including menstrual health, ear, nose and throat health, mental health, energy, normal blood glucose levels, muscle strength, and combinations thereof.

The filament of the present invention can comprise energy boosting agents. Energy boosting actives may provide mammals with more energy or a perception of more energy.

Non-limiting examples of energy boosting agents can include, but are not limited to, caffeine, green and black tea, taurine, *rhodiola rosea*, Siberian ginseng (*Eleutherococcus senticosus*), CoQ10, L-carnitine, L-Theanine, guarana (*Paullinia cupana*), *Schizandra chinensis*, yerba mate (*Ilex paraguariensis*), goji berry/Wolfberry (*Lycium barbarum* and *L. chinense*), quercetin (a plant-derived flavonol), amalaki/Indian gooseberry (*Phyllanthus emblica*), açai (from genus *Euterpe*), maca (*Lepidium meyenii*), ginkgo biloba, glucuronolactone, *panax ginseng* (from species within *Panax*, a genus of 11 species of slow-growing perennial plants with fleshy roots, in the family Araliaceae), *Echinacea* (genus of nine species of herbaceous plants in the Family Asteraceae), rooibos (*Aspalathus linearis*), DHEA, aromas and aromatherapy, noni (*Morinda citrifolia*), mangosteen (*Garcinia mangostana*), and combinations thereof.

Excipients

The filament and/or nonwoven web of the present invention can include one or more excipients. Non-limiting examples of excipients can include filament-forming materials, aesthetic agents, and combinations thereof. Non-limiting examples filament-forming materials can include backbone materials, extensional aids, rheology modifiers, crosslinking agents, and combinations thereof. Non-limiting examples of aesthetic agents can include flavors, colorants, sensates (cooling and/or heating agents), sweeteners, salivation agents, and combinations thereof.

Non-limiting examples of other ingestible active agents include essential oils such as antimicrobial and/or flavoring agents, saliva stimulating agents, cooling agents, sweeteners, color agents, sulfur precipitating agents, vitamins, minerals, dietary agents, medicinal agents, and mixtures thereof.

a. Flavoring Agents

The flavorings that can be used include those known to the skilled artisan, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit and fruit essences including apple, pear, peach, strawberry, raspberry, cherry, plum, pineapple, apricot and so forth. These flavorings can be used individually or in admixture. Commonly used flavors include mints such as peppermint, artificial vanilla, cinnamon derivatives, and various fruit flavors, whether employed individually or in admixture. Flavorings such as aldehydes and esters including cinnamyl acetate, cinnamaldehyde, citral, diethylacetal, dihydrocarvyl acetate, eugenyl formate, p-methylanisole, and so forth may also be used. Generally, any flavoring or food additive, such as those described in Chemicals Used in Food Processing, publication 1274 by the National Academy of Sciences, pages 63-258, may be used. Further examples of aldehyde flavorings include, but are not limited to acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; mixtures thereof; and the like.

b. Saliva Stimulating Agents

Non-limiting examples of saliva stimulating agents include food acids such as citric, lactic, malic, succinic, ascorbic, adipic, fumaric and tartaric acids.

c. Cooling Agents

Non-limiting examples of cooling agents, which may be an essential oil, include monomenthyl succinate, menthol (such as L-menthol), camphor, eucalyptus oil, lavender oil (such as Bulgarian Lavender Oil), thymol, methyl salicylate, and mixtures thereof.

d. Sweeteners

Non-limiting examples of suitable sweeteners that can be included in the filaments of the present invention include both natural and artificial sweeteners. In one example, the sweetener is selected from the group consisting of:

A. water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin;

B. water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like;

C. dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, and the like;

D. water-soluble sweeteners derived from naturally occurring water-soluble sweeteners, such as a chlorinated derivative of ordinary sugar (sucrose), known, for example, under the product description of sucralose; and E. protein based sweeteners such as *thaumatoccous danielli* (Thaumatin I and II), and mixtures thereof.

e. Sulfur Precipitating Agents (malodor reducing agents)

Sulfur precipitating agents useful in the present invention include metal salts such as copper salts and zinc salts. In one example, the sulfur precipitating agents are selected from the group consisting of copper gluconate, zinc citrate, zinc gluconate, and mixtures thereof.

f. Medicinal Agents

Any suitable medicine or medicinal composition, prescription or over-the-counter, that is ingestible by an animal, such as a human, may be delivered by a filament according to the present invention. For example, cough syrup or one or more of its ingredients may be delivered by ingesting one or more filaments comprising the cough syrup or one or more of its ingredients. Likewise, an upset stomach reliever such as Pepto-BISMOL® or ingredients therein, such as bismuth subsalicylate, may be delivered by a filament according to the present invention. In addition, antiseptics and/or antibacterial and/or antimicrobial for example alcohol and/or acids may be delivered by a filament according to the present invention.

g. Color Agents

The filaments of the present invention may comprise one or more color agents or colorants. The color agents may be used in amounts effective to produce a desired color. The color agents useful in the present invention, include pigments such as titanium dioxide, natural food colors and dyes suitable for food, drug and cosmetic applications, and mixtures thereof. Some color agents (colorants) are known as FD&C dyes and lakes. In one example, the color agents are water-soluble. Non-limiting examples of suitable color agents include FD&C Blue No. 2, which is the disodium salt of 5,5-indigotindisulfonic acid, the dye known as Green No. 3 comprises a triphenylmethane dye and is the monosodium salt of 4-[4-N-ethyl-p-sulfobenzylamino) diphenyl-methylene]-[1-N-ethyl-N-p-sulfonium benzyl)-2,5-cyclo-hexadienimine], and mixtures thereof. A full recitation of other suitable FD&C and D&C dyes and their corresponding chemical structures may be found in the Kirk-Othmer Encyclopedia of Chemical Technology, Volume 5, Pages 857-884, which text is accordingly incorporated herein by reference.

Other Additives

A wide variety of other ingredients useful in the filaments can be included in the filaments. Non-limiting examples of such other ingredients include carriers, hydrotropes, processing aids, dyes or pigments, solvents, and solid or other liquid fillers, erythrosine, colliodal silica, waxes, probiotics, surfactin, aminocellulosic polymers, Zinc Ricinoleate, perfume microcapsules, rhamnolipds, sophorolipids, glycopeptides, methyl ester sulfonates, methyl ester ethoxylates, sulfonated estolides, cleavable surfactants, biopolymers, silicones, modified silicones, aminosilicones, deposition aids, locust bean gum, cationic hydroxyethylcellulose polymers, cationic guars, hydrotropes (especially cumenesulfonate salts, toluenesulfonate salts, xylenesulfonate salts, and naphalene salts), antioxidants, BHT, PVA particle-encapsulated dyes or perfumes, pearlescent agents, effervescent agents, color change systems, silicone polyurethanes, opacifiers, tablet disintegrants, biomass fillers, fast-dry silicones, glycol distearate, hydroxyethylcellulose polymers, hydrophobically modified cellulose polymers or hydroxyethylcellulose polymers, starch perfume encapsulates, emulsified oils, bisphenol antioxidants, microfibrous cellulose structurants, properfumes, styrene/acrylate polymers, triazines, soaps, superoxide dismutase, benzophenone protease inhibitors, functionalized TiO2, dibutyl phosphate, silica perfume capsules, and other adjunct ingredients, diethylenetriaminepentaacetic acid, Tiron (1,2-dihydroxybenzene-3,5-disulfonic acid), hydroxyethanedimethylenephosphonic acid, methylglycinediacetic acid, choline oxidase, pectate lyase, triarylmethane blue and violet basic dyes, methine blue and violet basic dyes, anthraquinone blue and violet basic dyes, azo dyes basic blue 16, basic blue 65, basic blue 66 basic blue 67, basic blue 71, basic blue 159, basic violet 19, basic violet 35, basic violet 38, basic violet 48, oxazine dyes, basic blue 3, basic blue 75, basic blue 95, basic blue 122, basic blue 124, basic blue 141, Nile blue A and xanthene dye basic violet 10, an alkoxylated triphenylmethane polymeric colorant; an alkoxylated thiopene polymeric colorant; thiazolium dye, mica, titanium dioxide coated mica, bismuth oxychloride, and other actives.

The filaments of the present invention may also contain vitamins and amino acids such as: water soluble vitamins and their derivatives, water soluble amino acids and their salts and/or derivatives, water insoluble amino acids viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, heat transfer agents, chelants, proteins, skin active agents, sunscreens, UV absorbers, vitamins, niacinamide, caffeine and minoxidil.

The filaments of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C.I. Names. The compositions of the present invention may also contain antimicrobial agents which are useful as cosmetic biocides.

In one example, the filaments of the present invention may comprise processing aids and/or materials that provide a signal (visual, audible, smell, feel, taste) that identifies when one or more of the active agents within the filament and/or fiber has been released from the filament and/or fiber.

Buffer System

The filaments of the present invention may be formulated such that, during use in an aqueous cleaning operation, for example washing clothes or dishes, the wash water will have a pH of between about 5.0 and about 12 and/or between about 7.0 and 10.5. In the case of a dishwashing operation, the pH of the wash water typically is between about 6.8 and about 9.0. In the case of washing clothes, the pH of the was water typically is between 7 and 11. Techniques for controlling pH at recommended usage levels include the use of buffers, alkalis, acids, etc., and are well known to those skilled in the art. These include the use of sodium carbonate, citric acid or sodium citrate, monoethanol amine or other amines, boric acid or borates, and other pH-adjusting compounds well known in the art.

Filaments useful as "low pH" detergent compositions are included in the present invention and are especially suitable for the surfactant systems of the present invention and may provide in-use pH values of less than 8.5 and/or less than 8.0 and/or less than 7.0 and/or less than 7.0 and/or less than 5.5 and/or to about 5.0.

Dynamic in-wash pH profile filaments are included in the present invention. Such filaments may use wax-covered citric acid particles in conjunction with other pH control agents such that (i) 3 minutes after contact with water, the pH of the wash liquor is greater than 10; (ii) 10 mins after contact with water, the pH of the wash liquor is less than 9.5; (iii) 20 mins after contact with water, the pH of the wash liquor is less than 9.0; and (iv) optionally, wherein, the equilibrium pH of the wash liquor is in the range of from above 7.0 to 8.5.

Release of Active Agent

One or more active agents may be released from the filament when the filament is exposed to a triggering condition. In one example, one or more active agents may be released from the filament or a part of the filament when the filament or the part of the filament loses its identity, in other words, loses its physical structure. For example, a filament loses its physical structure when the filament-forming material dissolves, melts or undergoes some other transformative step such that the filament structure is lost. In one example, the one or more active agents are released from the filament when the filament's morphology changes.

In another example, one or more active agents may be released from the filament or a part of the filament when the filament or the part of the filament alters its identity, in other words, alters its physical structure rather than loses its physical structure. For example, a filament alters its physical structure when the filament-forming material swells, shrinks, lenthens, and/or shortens, but retains its filament-forming properties.

In another example, one or more active agents may be released from the filament with the filament's morphology not changing (not losing or altering its physical structure).

In one example, the filament may release an active agent upon the filament being exposed to a triggering condition that results in the release of the active agent, such as by causing the filament to lose or alter its identity as discussed above. Non-limiting examples of triggering conditions include exposing the filament to solvent, a polar solvent, such as alcohol and/or water, and/or a non-polar solvent, which may be sequential, depending upon whether the filament-forming material comprises a polar solvent-soluble material and/or a non-polar solvent-soluble material; exposing the filament to heat, such as to a temperature of greater than 75° F. and/or greater than 100° F. and/or greater than 150° F. and/or greater than 200° F. and/or greater than 212° F.; exposing the filament to cold, such as to a temperature of less than 40° F. and/or less than 32° F. and/or less than 0° F.; exposing the filament to a force, such as a stretching force applied by a consumer using the filament; and/or exposing the filament to a chemical reaction; exposing the filament to a condition that results in a phase change; exposing the filament to a pH change and/or a pressure change and/or temperature change; exposing the filament to one or more chemicals that result in the filament releasing one or more of its active agents; exposing the filament to ultrasonics; exposing the filament to light and/or certain wavelengths; exposing the filament to a different ionic strength; and/or exposing the filament to an active agent released from another filament.

In one example, one or more active agents may be released from the filaments of the present invention when a nonwoven web comprising the filaments is subjected to a triggering step selected from the group consisting of: pre-treating stains on a fabric article with the nonwoven web; forming a wash liquor by contacting the nonwoven web with water; tumbling the nonwoven web in a dryer; heating the nonwoven web in a dryer; and combinations thereof.

Filament-Forming Composition

The filaments of the present invention are made from a filament-forming composition. The filament-forming composition is a polar-solvent-based composition. In one example, the filament-forming composition is an aqueous composition comprising one or more filament-forming materials and one or more active agents.

The filament-forming composition of the present invention may have a shear viscosity as measured according to the Shear Viscosity Test Method described herein of from about 1 Pascal·Seconds to about 25 Pascal·Seconds and/or from about 2 Pascal·Seconds to about 20 Pascal·Seconds and/or from about 3 Pascal·Seconds to about 10 Pascal·Seconds, as measured at a shear rate of 3,000 sec$^{-1}$ and at the processing temperature (50° C. to 100° C.).

The filament-forming composition may be processed at a temperature of from about 50° C. to about 100° C. and/or from about 65° C. to about 95° C. and/or from about 70° C. to about 90° C. when making filaments from the filament-forming composition.

In one example, the filament-forming composition may comprise at least 20% and/or at least 30% and/or at least 40% and/or at least 45% and/or at least 50% to about 90% and/or to about 85% and/or to about 80% and/or to about 75% by weight of one or more filament-forming materials, one or more active agents, and mixtures thereof. The filament-forming composition may comprise from about 10% to about 80% by weight of a polar solvent, such as water.

The filament-forming composition may exhibit a Capillary Number of at least 1 and/or at least 3 and/or at least 5 such that the filament-forming composition can be effectively polymer processed into a hydroxyl polymer fiber.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time), $\eta$ is the fluid viscosity at the conditions of the die (units of Mass per Length*Time), $\sigma$ is the surface tension of the fluid (units of mass per Time$^2$).

When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length$^3$ per Time),
Area=cross-sectional area of the die exit (units of Length$^2$).

When the die opening is a circular hole, then the fluid velocity can be defined as $$V = \frac{Vol'}{\pi * R^2}$$

R is the radius of the circular hole (units of length).

The fluid viscosity will depend on the temperature and may depend of the shear rate. The definition of a shear thinning fluid includes a dependence on the shear rate. The surface tension will depend on the makeup of the fluid and the temperature of the fluid.

In a fiber spinning process, the filaments need to have initial stability as they leave the die. The Capillary number is used to characterize this initial stability criterion. At the conditions of the die, the Capillary number should be greater than 1 and/or greater than 4.

In one example, the filament-forming composition exhibits a Capillary Number of from at least 1 to about 50 and/or at least 3 to about 50 and/or at least 5 to about 30.

The filament-forming composition of the present invention may have a shear viscosity of from about 1 Pascal·Seconds to about 25 Pascal·Seconds and/or from about 2 Pascal·Seconds to about 20 Pascal·Seconds and/or from about 3

Pascal·Seconds to about 10 Pascal·Seconds, as measured at a shear rate of 3,000 sec$^{-1}$ and at the processing temperature (50° C. to 100° C.).

The filament-forming composition may be processed at a temperature of from about 50° C. to about 100° C. and/or from about 65° C. to about 95° C. and/or from about 70° C. to about 90° C. when making fibers from the filament-forming composition.

In one example, the non-volatile components of the spinning composition may comprise from about 20% and/or 30% and/or 40% and/or 45% and/or 50% to about 75% and/or 80% and/or 85% and/or 90%. The non-volatile components may be composed of filament-forming materials, such as backbone polymers, actives and combinations thereof. The volatile component of the spinning composition will comprise the remaining percentage and range from 10% to 80%.

The filament-forming composition may exhibit a Capillary Number of at least 1 and/or at least 3 and/or at least 5 such that the filament-forming composition can be effectively polymer processed into a hydroxyl polymer fiber.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time),
η is the fluid viscosity at the conditions of the die (units of Mass per Length*Time),
σ is the surface tension of the fluid (units of mass per Time$^2$).
When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length$^3$ per Time),
Area=cross-sectional area of the die exit (units of Length).
When the die opening is a circular hole, then the fluid velocity can be defined as $$V = \frac{Vol'}{\pi * R^2}$$

R is the radius of the circular hole (units of length).
The fluid viscosity will depend on the temperature and may depend of the shear rate. The definition of a shear thinning fluid includes a dependence on the shear rate. The surface tension will depend on the makeup of the fluid and the temperature of the fluid.

In a filament spinning process, the filaments need to have initial stability as they leave the die. The Capillary number is used to characterize this initial stability criterion. At the conditions of the die, the Capillary number should be greater than 1 and/or greater than 4.

In one example, the filament-forming composition exhibits a Capillary Number of from at least 1 to about 50 and/or at least 3 to about 50 and/or at least 5 to about 30.

In one example, the filament-forming composition may comprise one or more release agents and/or lubricants. Non-limiting examples of suitable release agents and/or lubricants include fatty acids, fatty acid salts, fatty alcohols, fatty esters, sulfonated fatty acid esters, fatty amine acetates and fatty amides, silicones, aminosilicones, fluoropolymers and mixtures thereof.

In one example, the filament-forming composition may comprise one or more antiblocking and/or detackifying agents. Non-limiting examples of suitable antiblocking and/or detackifying agents include starches, modified starches, crosslinked polyvinylpyrrolidone, crosslinked cellulose, microcrystalline cellulose, silica, metallic oxides, calcium carbonate, talc and mica.

Active agents of the present invention may be added to the filament-forming composition prior to and/or during filament formation and/or may be added to the filament after filament formation. For example, a perfume active agent may be applied to the filament and/or nonwoven web comprising the filament after the filament and/or nonwoven web according to the present invention are formed. In another example, an enzyme active agent may be applied to the filament and/or nonwoven web comprising the filament after the filament and/or nonwoven web according to the present invention are formed. In still another example, one or more particulate active agents, such as one or more ingestible active agents, such as bismuth subsalicylate, which may not be suitable for passing through the spinning process for making the filament, may be applied to the filament and/or nonwoven web comprising the filament after the filament and/or nonwoven web according to the present invention are formed.

Extensional Aids

In one example, the filament comprises an extensional aid. Non-limiting examples of extensional aids can include polymers, other extensional aids, and combinations thereof.

In one example, the extensional aids have a weight-average molecular weight of at least about 500,000 Da. In another example, the weight average molecular weight of the extensional aid is from about 500,000 to about 25,000,000, in another example from about 800,000 to about 22,000,000, in yet another example from about 1,000,000 to about 20,000,000, and in another example from about 2,000,000 to about 15,000,000. The high molecular weight extensional aids are preferred in some examples of the invention due to the ability to increase extensional melt viscosity and reducing melt fracture.

The extensional aid, when used in a meltblowing process, is added to the composition of the present invention in an amount effective to visibly reduce the melt fracture and capillary breakage of fibers during the spinning process such that substantially continuous fibers having relatively consistent diameter can be melt spun. Regardless of the process employed to produce filaments, the extensional aids, when used, can be present from about 0.001% to about 10%, by weight on a dry filament basis, in one example, and in another example from about 0.005 to about 5%, by weight on a dry filament basis, in yet another example from about 0.01 to about 1%, by weight on a dry filament basis, and in another example from about 0.05% to about 0.5%, by weight on a dry filament basis.

Non-limiting examples of polymers that can be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include carboxyl modified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Method for Making Filament

The filaments of the present invention may be made by any suitable process. A non-limiting example of a suitable process for making the filaments is described below.

In one example, a method for making a filament according to the present invention comprises the steps of:
 a. providing a filament-forming composition comprising one or more filament-forming materials and one or more active agents; and
 b. spinning the filament-forming composition into one or more filaments comprising the one or more filament-forming materials and the one or more active agents that are releasable from the filament when exposed to conditions of intended use, wherein the total level of the one or more filament-forming materials present in the filament is less than 65% and/or 50% or less by weight on a dry filament basis and the total level of the one or more active agents present in the filament is greater than 35% and/or 50% or greater by weight on a dry filament basis.

In one example, during the spinning step, any volatile solvent, such as water, present in the filament-forming composition is removed, such as by drying, as the filament is formed. In one example, greater than 30% and/or greater than 40% and/or greater than 50% of the weight of the filament-forming composition's volatile solvent, such as water, is removed during the spinning step, such as by drying the filament being produced.

The filament-forming composition may comprise any suitable total level of filament-forming materials and any suitable level of active agents so long as the filament produced from the filament-forming composition comprises a total level of filament-forming materials in the filament of from about 5% to 50% or less by weight on a dry filament basis and a total level of active agents in the filament of from 50% to about 95% by weight on a dry filament basis.

In one example, the filament-forming composition may comprise any suitable total level of filament-forming materials and any suitable level of active agents so long as the filament produced from the filament-forming composition comprises a total level of filament-forming materials in the filament of from about 5% to 50% or less by weight on a dry filament basis and a total level of active agents in the filament of from 50% to about 95% by weight on a dry filament basis, wherein the weight ratio of filament-forming material to additive is 1 or less.

In one example, the filament-forming composition comprises from about 1% and/or from about 5% and/or from about 10% to about 50% and/or to about 40% and/or to about 30% and/or to about 20% by weight of the filament-forming composition of filament-forming materials; from about 1% and/or from about 5% and/or from about 10% to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of a volatile solvent, such as water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more filaments by any suitable spinning process, such as meltblowing and/or spunbonding. In one example, the filament-forming composition is spun into a plurality of filaments by meltblowing. For example, the filament-forming composition may be pumped from an extruder to a meltblown spinneret. Upon exiting one or more of the filament-forming holes in the spinneret, the filament-forming composition is attenuated with air to create one or more filaments. The filaments may then be dried to remove any remaining solvent used for spinning, such as the water.

The filaments of the present invention may be collected on a belt, such as a patterned belt to form a nonwoven web comprising the filaments.

Nonwoven Web

One or more, and/or a plurality of filaments of the present invention may form a nonwoven web by any suitable process known in the art. The nonwoven web may be used to deliver the active agents from the filaments of the present invention when the nonwoven web is exposed to conditions of intended use of the filaments and/or nonwoven web.

Even though the filament and/or nonwoven web and/or film of the present invention are in solid form, the filament-forming composition used to make the filaments of the present invention may be in the form of a liquid.

In one example, the nonwoven web comprises a plurality of identical or substantially identical from a compositional perspective filaments according to the present invention. In another example, the nonwoven web may comprise two or more different filaments according to the present invention. Non-limiting examples of differences in the filaments may be physical differences such as differences in diameter, length, texture, shape, rigidity, elasticity, and the like; chemical differences such as crosslinking level, solubility, melting point, Tg, active agent, filament-forming material, color, level of active agent, level of filament-forming material, presence of any coating on filament, biodegradable or not, hydrophobic or not, contact angle, and the like; differences in whether the filament loses its physical structure when the filament is exposed to conditions of intended use; differences in whether the filament's morphology changes when the filament is exposed to conditions of intended use; and differences in rate at which the filament releases one or more of its active agents when the filament is exposed to conditions of intended use. In one example, two or more filaments within the nonwoven web may comprise the same filament-forming material, but have different active agents. This may be the case where the different active agents may be incompatible with one another, for example an anionic surfactant (such as a shampoo active agent) and a cationic surfactant (such as a hair conditioner active agent).

Figure 4:
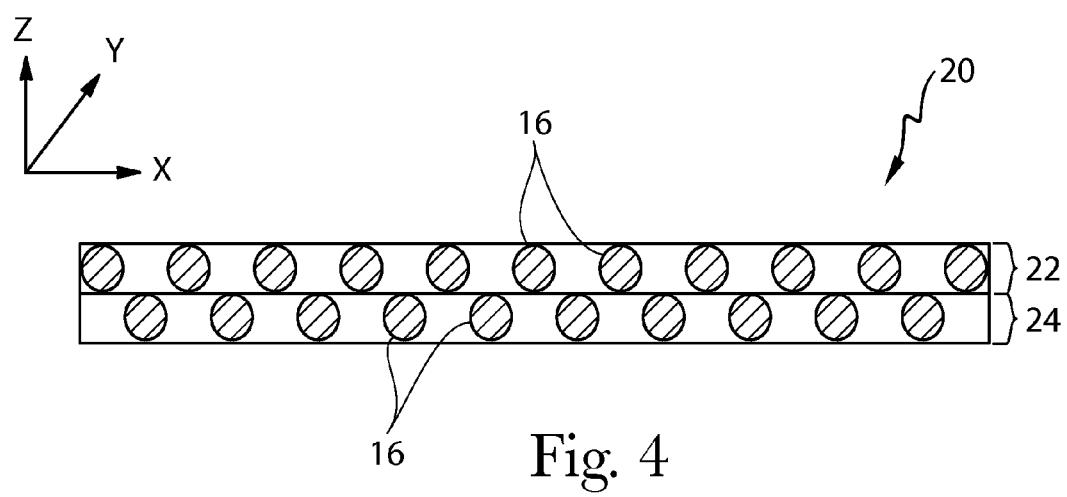
FIG. 4 is a schematic representation of an example of a nonwoven web according to the present invention.

In another example, as shown in FIG. 4, the nonwoven web 20 may comprise two or more different layers 22, 24 (in the z-direction of the nonwoven web 20 of filaments 16 of the present invention that form the nonwoven web 20. The filaments 16 in layer 22 may be the same as or different from the filaments 16 of layer 24. Each layer 22, 24 may comprise a plurality of identical or substantially identical or different filaments. For example, filaments that may release their active agents at a faster rate than others within the nonwoven web may be positioned to an external surface of the nonwoven web.

In another example, the nonwoven web may exhibit different regions, such as different regions of basis weight, density and/or caliper. In yet another example, the nonwoven web may comprise texture on one or more of its surfaces. A surface of the nonwoven web may comprise a pattern, such as a non-random, repeating pattern. The nonwoven web may be embossed with an emboss pattern. In another example, the nonwoven web may comprise apertures. The apertures may be arranged in a non-random, repeating pattern.

In one example, the nonwoven web may comprise discrete regions of filaments that differ from other parts of the nonwoven web.

Non-limiting examples of use of the nonwoven web of the present invention include, but are not limited to a laundry dryer substrate, washing machine substrate, washcloth, hard surface cleaning and/or polishing substrate, floor cleaning and/or polishing substrate, as a component in a battery, baby wipe, adult wipe, feminine hygiene wipe, bath tissue wipe, window cleaning substrate, oil containment and/or scavenging substrate, insect repellant substrate, swimming pool chemical substrate, food, breath freshener, deodorant, waste disposal bag, packaging film and/or wrap, wound dressing, medicine delivery, building insulation, crops and/or plant cover and/or bedding, glue substrate, skin care substrate, hair care substrate, air care substrate, water treatment substrate and/or filter, toilet bowl cleaning substrate, candy substrate, pet food, livestock bedding, teeth whitening substrates, carpet cleaning substrates, and other suitable uses of the active agents of the present invention.

The nonwoven web of the present invention may be used as is or may be coated with one or more active agents.

In another example, the nonwoven web of the present invention may be pressed into a film, for example by applying a compressive force and/or heating the nonwoven web to convert the nonwoven web into a film. The film would comprise the active agents that were present in the filaments of the present invention. The nonwoven web may be completely converted into a film or parts of the nonwoven web may remain in the film after partial conversion of the nonwoven web into the film. The films may be used for any suitable purposes that the active agents may be used for including, but not limited to the uses exemplified for the nonwoven web.

In one example, the nonwoven web of the present invention exhibits an average disintegration time per g of sample of less than 120 and/or less than 100 and/or less than 80 and/or less than 55 and/or less than 50 and/or less than 40 and/or less than 30 and/or less than 20 seconds/gram (s/g) as measured according to the Dissolution Test Method described herein.

In another example, the nonwoven web of the present invention exhibits an average dissolution time per g of sample of less than 950 and/or less than 900 and/or less than 800 and/or less than 700 and/or less than 600 and/or less than 550 s/g as measured according to the Dissolution Test Method described herein.

In one example, the nonwoven web of the present invention exhibits a thickness of greater than 0.01 mm and/or greater than 0.05 mm and/or greater than 0.1 mm and/or to about 20 mm and/or to about 10 mm and/or to about 5 mm and/or to about 2 mm and/or to about 0.5 mm and/or to about 0.3 mm as measured by the Thickness Test Method described herein.

Automatic Dishwashing Articles

Automatic dishwashing articles comprise one or more filaments and/or fibers and/or nonwoven webs and/or films of the present invention and a surfactant system, and optionally one or more optional ingredients known in the art of cleaning, for example useful in cleaning dishware in an automatic dishwashing machine. Examples of these optional ingredients include: anti-scalants, bleaching agents, perfumes, dyes, antibacterial agents, enzymes (e.g., protease), cleaning polymers (e.g., alkoxylated polyethyleneimine polymer), hydrotropes, suds inhibitors, carboxylic acids, thickening agents, preservatives, disinfecting agents, pH buffering means so that the automatic dishwashing liquor generally has a pH of from 3 to 14 (alternatively 8 to 11), or mixtures thereof. Examples of automatic dishwashing actives are described in U.S. Pat. Nos. 5,679,630; 5,703,034; 5,703,034; 5,705,464; 5,962,386; 5,968,881; 6,017,871; 6,020,294.

Scale formation can be a problem. It can result from precipitation of alkali earth metal carbonates, phosphates, and silicates. Examples of anti-scalants include polyacrylates and polymers based on acrylic acid combined with other moieties. Sulfonated varieties of these polymers are particular effective in nil phosphate formulation executions. Examples of anti-sealants include those described in U.S. Pat. No. 5,783,540, col. 15, l. 20-col. 16, l. 2; and EP 0 851 022 A2, pg. 12, l. 1-20.

In one embodiment, an automatic dishwashing article is provided comprising a filament and/or fiber and/or nonwoven web of the present invention, a nonionic surfactant, a sulfonated polymer, optionally a chelant, optionally a builder, and optionally a bleaching agent, and mixtures thereof. A method of cleaning dishware is provided comprising the step of dosing an automatic dishwashing article of the present invention into an automatic dishwashing machine.

Hand Dishwashing Articles

Hand dish washing articles comprise one or more filaments and/or fibers and/or nonwoven webs and/or films of the present invention and a surfactant system, and optionally one or more optional ingredients known in the art of cleaning, for example useful in cleaning dishware by hand. Examples of these optional ingredients include: perfume, dyes, antibacterial agents, enzymes (e.g., protease), cleaning polymers (e.g., alkoxylated polyethyleneimine polymer), hydrotropes, polymeric suds stabilizers, bleaching agent, diamines, carboxylic acids, thickening agents, preservatives, disinfecting agents, pH buffering means so that the dish washing liquor generally has a pH of from 3 to 14 (preferably from 8 to 11), or mixtures thereof. Examples of hand dishwashing actives are described in U.S. Pat. Nos. 5,990,065; and 6,060,122.

In one embodiment, the surfactant of the hand dishwashing article comprises an alkyl sulfate, an alkoxy sulfate, an alkyl sulfonate, an alkoxy sulfonate, an alkyl aryl sulfonate, an amine oxide, a betaine or a derivative of aliphatic or heterocyclic secondary and ternary amine, a quaternary ammonium surfactant, an amine, a singly or multiply alkoxylated alcohol, an alkyl polyglycoside, a fatty acid amide surfactant, a $C_8$-$C_{20}$ ammonia amide, a monoethanolamide, a diethanolamide, an isopropanolamide, a polyhydroxy fatty acid amide, or a mixture thereof.

A method of washing dishware is provided comprising the step of dosing a hand dishwashing article of the present invention in a sink or basin suitable for containing soiled dishware. The sink or basin may contain water and/or soiled dishware.

Hard Surface Cleaning Article

Hard surface cleaning articles comprise one or more filaments and/or fibers and/or nonwoven webs and/or films of the present invention and optionally one or more optional ingredients known in the art of cleaning, for example useful in cleaning hard surfaces, such as an acid constituent, for example an acid constituent that provides good limescale removal performance (e.g., formic acid, citric acid, sorbic acid, acetic acid, boric acid, maleic acid, adipic acid, lactic acid malic acid, malonic acid, glycolic acid, or mixtures thereof). Examples of ingredients that may be included an acidic hard surface cleaning article may include those described in U.S. Pat. No. 7,696,143. Alternatively the hard surface cleaning article comprises an alkalinity constituent (e.g., alkanolmine, carbonate, bicarbonate compound, or mixtures thereof). Examples of ingredients that may be included in an alkaline hard surface cleaning article may include those described in US 2010/0206328 A1. A method of cleaning a hard surface includes using or dosing a hard surface cleaning article in a method to clean a hard surface. In one embodiment, the method comprises dosing a hard surface cleaning article in a bucket or similar container, optionally adding water to the bucket before or after dosing the article to the bucket. In another embodiment, the method comprising dosing a hard surface cleaning article in a toilet bowl, optionally scrubbing the surface of the toilet bowl after the article has dissolved in the water contained in the toilet bowl.

Toilet Bowl Cleaning Head

A toilet bowl cleaning head for a toilet bowl cleaning implement comprising one or more filaments and/or fibers and/or nonwoven webs and/or films of the present invention is provided. The toilet bowl cleaning head may be disposable. The toilet bowl cleaning head may be removably attached to a handle, so that the user's hands remain remote from the toilet bowl. In one embodiment, the toilet bowl cleaning head may contain a water dispersible shell. In turn, the water dispersible shell may comprise one or more filaments and/or fibers and/or nonwoven webs and/or films of the present invention. This water dispersible shell may encase a core. The core may comprise at least one granular material. The granular material of the core may comprise surfactants, organic acids, perfumes, disinfectants, bleaches, detergents, enzymes, particulates, or mixtures thereof. Optionally, the core may be free from cellulose, and may comprise one or more filaments and/or fibers and/or nonwoven webs and/or films of the present invention. Examples a suitable toilet bowl cleaning head may be made according to commonly assigned US patent application publication number 20120084933 (P&G Case 11892). A suitable toilet bowl cleaning head containing starch materials may be made according to commonly assigned US patent application publication numbers 20120246853 (P&G case 12048), 20120246850 (P&G case 12049) and/or 20120246854 (P&G case 12054). A method of cleaning a toilet bowl surface is provided comprising the step of contacting the toilet bowl surface with a toilet bowl cleaning head of the present invention.

Methods of Use

The nonwoven webs or films comprising one or more fabric care active agents according the present invention may be utilized in a method for treating a fabric article. The method of treating a fabric article may comprise one or more steps selected from the group consisting of: (a) pre-treating the fabric article before washing the fabric article; (b) contacting the fabric article with a wash liquor formed by contacting the nonwoven web or film with water; (c) contacting the fabric article with the nonwoven web or film in a dryer; (d) drying the fabric article in the presence of the nonwoven web or film in a dryer; and (e) combinations thereof.

In some embodiments, the method may further comprise the step of pre-moistening the nonwoven web or film prior to contacting it to the fabric article to be pre-treated. For example, the nonwoven web or film can be pre-moistened with water and then adhered to a portion of the fabric comprising a stain that is to be pre-treated. Alternatively, the fabric may be moistened and the web or film placed on or adhered thereto. In some embodiments, the method may further comprise the step of selecting of only a portion of the nonwoven web or film for use in treating a fabric article. For example, if only one fabric care article is to be treated, a portion of the nonwoven web or film may be cut and/or torn away and either placed on or adhered to the fabric or placed into water to form a relatively small amount of wash liquor which is then used to pre-treat the fabric. In this way, the user may customize the fabric treatment method according to the task at hand. In some embodiments, at least a portion of a nonwoven web or film may be applied to the fabric to be treated using a device. Exemplary devices include, but are not limited to, brushes and sponges. Any one or more of the aforementioned steps may be repeated to achieve the desired fabric treatment benefit.

Process for Making a Film

The nonwoven web of the present invention may be converted into a film. An example of a process for making a film from a nonwoven web according to the present invention comprises the steps of:

a. providing a nonwoven web comprising a plurality of filaments comprising a filament-forming material, for example a polar solvent-soluble filament-forming material; and b. converting the nonwoven web into a film.

In one example of the present invention, a process for making a film from a nonwoven web comprises the steps of providing a nonwoven web and converting the nonwoven web into a film.

The step of converting the nonwoven web into a film may comprise the step of subjecting the nonwoven web to a force. The force may comprise a compressive force. The compressive force may apply from about 0.2 MPa and/or from about 0.4 MPa and/or from about 1 MPa and/or to about 10 MPa and/or to about 8 MPa and/or to about 6 MPa of pressure to the nonwoven web.

The nonwoven web may be subjected to the force for at least 20 milliseconds and/or at least 50 milliseconds and/or at least 100 milliseconds and/or to about 800 milliseconds and/or to about 600 milliseconds and/or to about 400 milliseconds and/or to about 200 milliseconds. In one example, the nonwoven web is subjected to the force for a time period of from about 400 milliseconds to about 800 milliseconds.

The nonwoven web may be subjected to the force at a temperature of at least 50° C. and/or at least 100° C. and/or at least 140° C. and/or at least 150° C. and/or at least 180° C. and/or to about 200° C. In one example, the nonwoven web is subjected to the force at a temperature of from about 140° C. to about 200° C.

The nonwoven web may be supplied from a roll of nonwoven web. The resulting film may be wound into a roll of film.

Non-Limiting Examples

Figure 5:
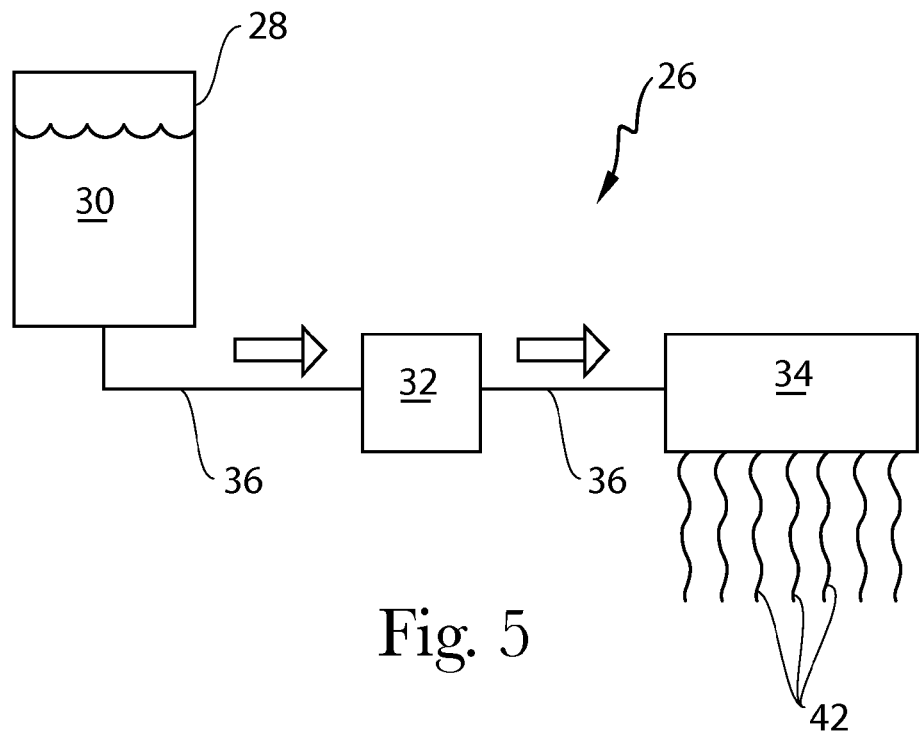
FIG. 5 is a schematic representation of an apparatus suitable for making a filament according to the present invention.
Figure 6:
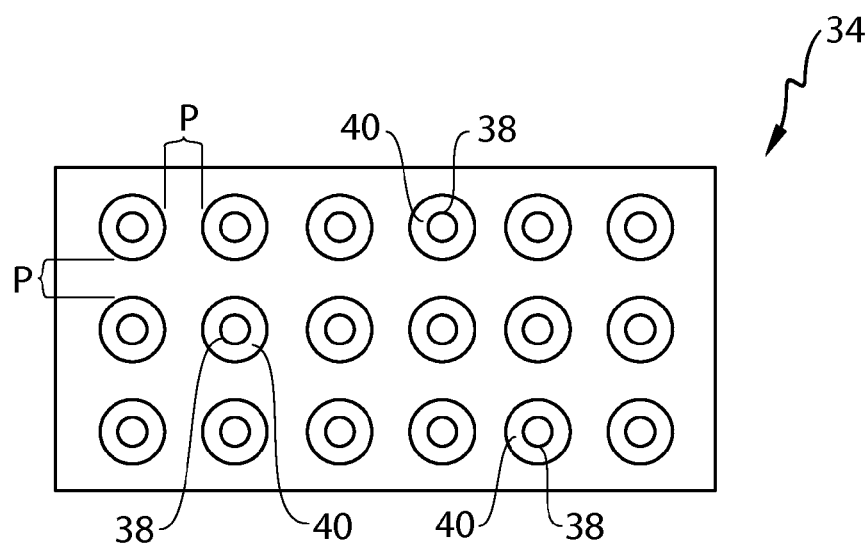
FIG. 6 is a schematic representation of a die suitable for spinning a filament according to the present invention.

Non-limiting examples of filaments according to the present invention are produced by using a small-scale apparatus 26, a schematic representation of which is shown in FIGS. 5 and 6. A pressurized tank 28 suitable for batch operations is filled with a filament-forming composition 30, for example a filament-forming composition that is suitable for making filaments useful as fabric care compositions and/or dishwashing compositions.

In a first example as set forth in Example 1 below, a filament-forming composition 30 according to the present invention is made as follows: two separate parts are combined to produce the filament-forming composition 30. A first part, Part A, containing 15% by weight solids solution of polyvinyl alcohol is made by mixing dry polyvinyl alcohol with 85% by weight deionized water and heating the mixture to about 90°

C. and adding mechanical mixing, if needed, until all or substantially all of the polyvinyl alcohol is dissolved in the deionized water. This material is then allowed to cool to about 73° F.±4° F. (about 23° C.±2.2° C.). Next, a second part, Part B, containing 24.615% by weight deionized water and the balance additives, including active agents such as surfactants, pH adjusting agents and chelating agents that exhibit a combined total weight % of greater than 50% is then added to Part A. The resulting mixture is hand mixed to form the filament-forming composition. This filament-forming is suitable for spinning into filaments according to the present invention.

In a second example as set forth in Example 2 below, a filament-forming composition 30 combines Part A and Part B at the indicated weight percentages set forth in Table 2A below. The weight percent of ingredients of a filament resulting from the filament-forming composition of Table 2A is shown in Table 2B below.

In a third example as set forth in Example 3 below, a filament-forming composition combines Part A and Part B at the indicated weight percentages set forth in Table 3A below. The weight percent of ingredients of a filament resulting from the filament-forming composition of Table 3A is shown in Table 3B below.

In a fourth example as set forth in Example 4 below, a filament-forming composition contains the ingredients as set forth in Table 4 below.

In a fifth example as set forth in Example 5 below, a filament-forming composition contains the ingredients as set forth in Table 5 below.

In a sixth example as set forth in Example 6 below, a filament-forming composition contains the ingredients as set forth in Table 6 below.

In a seventh example as set forth in Example 7 below, a filament-forming composition contains the ingredients as set forth in Table 7 below.

Additional examples are set forth in Examples 8-12 below.

A pump 32 (for example a Zenith®, type PEP II pump having a capacity of 5.0 cubic centimeters per revolution (cc/rev), manufactured by Parker Hannifin Corporation, Zenith Pumps division, of Sanford, N.C., USA) is used to pump the filament-forming composition 30 to a die 34. The filament-forming composition's material flow to a die 34 is controlled by adjusting the number of revolutions per minute (rpm) of the pump 32. Pipes 36 are connected the tank 28, the pump 32, and the die 34 in order to transport (as represented by the arrows) the filament-forming composition 30 from the tank 28 to the pump 32 and into the die 34. The die 34 as shown in FIG. 6 has two or more rows of circular extrusion nozzles 38 spaced from one another at a pitch P of about 1.524 millimeters (about 0.060 inches). The nozzles 38 have individual inner diameters of about 0.305 millimeters (about 0.012 inches) and individual outside diameters of about 0.813 millimeters (about 0.032 inches). Each individual nozzle 38 is encircled by an annular and divergently flared orifice 40 to supply attenuation air to each individual nozzle 38. The filament-forming composition 30 that is extruded through the nozzles 38 is surrounded and attenuated by generally cylindrical, humidified air streams supplied through the orifices 40 encircling the nozzles 38 to produce the filaments 42. Attenuation air is provided by heating compressed air from a source by an electrical-resistance heater, for example, a heater manufactured by Chromalox, Division of Emerson Electric, of Pittsburgh, Pa., USA. An appropriate quantity of steam is added to the attenuation air to saturate or nearly saturate the heated air at the conditions in the electrically heated, thermostatically controlled delivery pipe. Condensate is removed in an electrically heated, thermostatically controlled, separator.

The filaments 42 are dried by a drying air stream having a temperature of from about 149° C. (about 300° F.) to about 315° C. (about 600° F.) by an electrical resistance heater (not shown) supplied through drying nozzles (not shown) and discharged at an angle of about 90° relative to the general orientation of the filaments 42 being spun.

The filaments may be collected on a collection device, such as a belt or fabric, in one example a belt or fabric capable of imparting a pattern, for example a non-random repeating pattern to a nonwoven web formed as a result of collecting the filaments on the belt or fabric.

EXAMPLE 1

An example of a filament and/or nonwoven web of the present invention suitable for providing a beauty benefit is shown in Table 1 below.

TABLE 1

| | % by weight of filament-forming composition (i.e., premix) | Filament-Forming Composition (g) | Filament (i.e., components remaining upon drying) (g) | % by weight on a dry filament basis |
|---|---|---|---|---|
| PART A | | | | |
| Polyvinyl alcohol[1] | 15.000 | 178.170 | 178.170 | 24.7% |
| Deionized water | 85.000 | 1009.630 | | |
| PART B | | | | |
| Deionized water | 24.615 | 195.394 | | |
| Anionic surfactants | 45.180 | 322.815 | 322.815 | 49.8% |
| Nonionic surfactants | 1.241 | 9.851 | 9.851 | 1.4% |
| pH adjusting agent | 7.114 | 56.471 | 56.471 | 7.8% |
| Chelants | 2.154 | 17.098 | 17.098 | 2.4% |
| Other ingredients | | | | Balance |
| Combined A and B | | | | |
| Solids | | 720.923 | 36.4% | |
| Deionized water | | 1260.701 | 63.6% | |

[1]Sigma-Aldrich Catalog No. 363081, MW 85,000-124,000, 87-89% hydrolyzed

EXAMPLE 2

Table 2A below sets forth another example of a filament-forming composition of the present invention for making filaments and/or nonwoven web of the present invention suitable for providing a beauty benefit.

TABLE 2A

| | % by weight of filament-forming composition (i.e., premix) |
|---|---|
| PART A | |
| Glycerin | 3.2 |
| Polyvinyl alcohol[1] | 8.1 |
| Distilled water | 88.7 |
| PART B | |
| Sodium Lauroamphoacetate (26% activity)[2] | 31.8 |
| Ammonium Laureth-3 sulfate (25% activity) | 4.9 |
| Ammonium Undecyl sulfate (24% activity) | 19.9 |
| Ammonium Laureth-1 sulfate (70% activity) | 8.0 |
| Cationic cellulose[3] | 0.5 |

TABLE 2A-continued

| | % by weight of filament-forming composition (i.e., premix) |
|---|---|
| Citric Acid | 1.6 |
| Distilled water | 33.3 |

[1] Sigma-Aldrich Catalog No. 363081, MW 85,000-124,000, 87-89% hydrolyzed
[2] McIntyre Group Ltd, University Park, IL, Mackam HPL-28ULS
[3] UCARE ™ Polymer LR-400, available from Amerchol Corporation (Plaquemine, Louisiana)

The resulting filaments from the filament-forming composition of Table 2A exhibits the following levels of active agents and of filament-forming materials as set forth in Table 2B below.

TABLE 2B

| Solid Fibers Compositional Parameter | Estimated Value % by weight on a dry filament basis |
|---|---|
| Active Agents (Surfactants) | 60.6 wt. % |
| Filament-forming Material (Polyvinylalcohol) | 23.7 wt. % |
| Weight Ratio of Filament-forming Material to Active Agent | 0.39 |

EXAMPLE 3

Table 3A below sets forth another example of a filament-forming composition of the present invention for making filaments and/or nonwoven web of the present invention suitable for providing a beauty benefit.

TABLE 3A

| | % by weight of filament-forming composition (i.e., premix) |
|---|---|
| PART A | |
| Glycerin | 13.5 |
| Polyvinyl alcohol[1] | 8.1 |
| Distilled water | 78.4 |
| PART B | |
| Sodium Lauroamphoacetate (26% activity)[2] | 38.2 |
| Ammonium Laureth-3 sulfate (70% activity) | 2.9 |
| Ammonium Undecyl sulfate (70% activity) | 9.8 |
| Ammonium Laureth-1 sulfate (70% activity) | 9.8 |
| Cationic cellulose[3] | 0.5 |
| Poly(ethylene oxide)[4] | 2.0 |
| Distilled water | 36.8 |

[1] Sigma-Aldrich Catalog No. 363081, MW 85,000-124,000, 87-89% hydrolyzed
[2] McIntyre Group Ltd, University Park, IL, Mackam HPL-28ULS
[3] UCARE ™ Polymer LR-400, available from Amerchol Corporation (Plaquemine, Louisiana)
[4] Average MW 8,000,000, available from Sigma Aldrich, Catalog Number 372838

The resulting filaments from the filament-forming composition of Table 3A exhibits the following levels of active agents and of filament-forming materials as set forth in Table 3B below.

TABLE 3B

| Solid Fibers Compositional Parameter | Estimated Value % by weight on a dry filament basis |
|---|---|
| Active Agents (Surfactants) | 49.4 wt. % |
| Filament-forming Material (Polyvinylalcohol) | 15.5 wt. % |
| Weight Ratio of Filament-forming Material to Active Agent | 0.31 |

EXAMPLE 4

Table 4 below sets forth another example of a filament-forming composition of the present invention for making filaments and/or a nonwoven web of the present invention suitable for use as a laundry detergent.

TABLE 4

| | % by weight of filament-forming composition (i.e., premix) | Filament-Forming Composition (%) | Filament (i.e., components remaining upon drying) (%) | % by weight on a dry filament basis |
|---|---|---|---|---|
| C12-15 AES | 28.45 | 11.38 | 11.38 | 28.07 |
| C11.8 HLAS | 12.22 | 4.89 | 4.89 | 12.05 |
| MEA | 7.11 | 2.85 | 2.85 | 7.02 |
| N67HSAS | 4.51 | 1.81 | 1.81 | 4.45 |
| Glycerol | 3.08 | 1.23 | 1.23 | 3.04 |
| PE-20, Polyethyleneimine Ethoxylate, PEI 600 E20 | 3.00 | 1.20 | 1.20 | 2.95 |
| Ethoxylated/Propoxylated Polyethyleneimine | 2.95 | 1.18 | 1.18 | 2.91 |
| Brightener 15 | 2.20 | 0.88 | 0.88 | 2.17 |
| Amine Oxide | 1.46 | 0.59 | 0.59 | 1.44 |
| Sasol 24,9 Nonionic Surfactant | 1.24 | 0.50 | 0.50 | 1.22 |
| DTPA (Chelant) | 1.08 | 0.43 | 0.43 | 1.06 |
| Tiron (Chelant) | 1.08 | 0.43 | 0.43 | 1.06 |
| Celvol 523 PVOH[1] | 0.000 | 13.20 | 13.20 | 32.55 |
| Water | 31.629 | 59.43 | | Trace |

[1] Celvol 523, Celanese/Sekisui, MW 85,000-124,000, 87-89% hydrolyzed

EXAMPLE 5

Table 5 below sets forth another example of a filament-foaming composition of the present invention for making filaments and/or a nonwoven web of the present invention suitable for use as a laundry detergent.

TABLE 5

| | % by weight of filament-forming composition (i.e., premix) | Filament-Forming Composition (%) | Filament (i.e., components remaining upon drying) (%) | % by weight on a dry filament basis |
|---|---|---|---|---|
| C12-15 AES | 23.13 | 9.25 | 9.25 | 24.05 |
| C11.8 HLAS | 13.55 | 5.42 | 5.42 | 14.10 |
| MEA | 6.91 | 2.76 | 2.76 | 7.20 |
| N67HSAS | 3.66 | 1.46 | 1.46 | 3.82 |
| Glycerol | 2.97 | 1.19 | 1.19 | 3.09 |
| PE-20, | 2.81 | 1.12 | 1.12 | 3.92 |

TABLE 5-continued

| | % by weight of filament-forming composition (i.e., premix) | Filament-Forming Composition (%) | Filament (i.e., components remaining upon drying) (%) | % by weight on a dry filament basis |
|---|---|---|---|---|
| Polyethyleneimine Ethoxylate, PEI 600 E20 | | | | |
| Ethoxylated/Propoxylated Polyethyleneimine | 2.81 | 1.12 | 1.12 | 2.92 |
| Brightener 15 | 0.25 | 0.15 | 0.15 | 0.26 |
| Amine Oxide | 1.26 | 0.50 | 0.50 | 1.32 |
| Sasol 24,9 Nonionic Surfactant | 2.17 | 0.87 | 0.87 | 2.26 |
| DTPA (Chelant) | 1.01 | 0.40 | 0.40 | 1.06 |
| Tiron (Chelant) | 1.01 | 0.40 | 0.40 | 1.05 |
| Celvol 523 PVOH[1] | 0.00 | 13.80 | 13.80 | 32.92 |
| Water | 38.46 | 61.53 | | Trace |

[1]Celvol 523, Celanese/Sekisui, MW 85,000-124,000, 87-89% hydrolyzed

EXAMPLE 6

Table 6 below sets forth another example of a filament-forming composition of the present invention for making filaments and/or a nonwoven web of the present invention suitable for use as a hand dishwashing detergent.

TABLE 6

| | % by weight of filament-forming composition (i.e., premix) | Filament-Forming Composition (%) | Filament (i.e., components remaining upon drying) (%) | % by weight on a dry filament basis |
|---|---|---|---|---|
| NaAE0.6S | 31.09 | 12.43 | 12.43 | 24.05 |
| 1,3-BAC Diamine | 0.35 | 0.14 | 0.14 | 14.10 |
| PGC Amine Oxide | 7.20 | 2.88 | 2.88 | 7.20 |
| Tridecylalcohol-EO9 | 6.00 | 2.40 | 2.40 | 3.82 |
| Sodium cumene sulfonate | 2.22 | 0.89 | 0.89 | 3.09 |
| GLDA | 2.22 | 0.89 | 0.89 | 3.92 |
| Ethanol | 2.17 | 0.87 | 0.87 | 2.92* |
| Sodium Chloride | 1.40 | 0.56 | 0.56 | 0.26 |
| Magnesium chloride | 0.61 | 0.24 | 0.24 | 1.32 |
| pH Trim | 0.50 | 0.20 | 0.20 | 2.26 |
| NaOH | 0.46 | 0.18 | 0.18 | 1.06 |
| Acticide | 0.05 | 0.02 | 0.02 | 1.05 |
| Celvol 523 PVOH[1] | 0.000 | 13.20 | 13.20 | 32.97 |
| Water | 45.74 | 65.10 | | Trace |

[1]Celvol 523, Celanese/Sekisui, MW 85,000-124,000, 87-89% hydrolyzed
*Calculated

EXAMPLE 7

Table 7 below sets forth another example of a filament-forming composition of the present invention for making filaments and/or a nonwoven web of the present invention suitable for use as a laundry detergent.

TABLE 7

| | % by weight of filament-forming composition (i.e., premix) | Filament-Forming Composition (%) | Filament (i.e., components remaining upon drying) (%) | % by weight on a dry filament basis |
|---|---|---|---|---|
| C12-15 AES | 23.13 | 9.25 | 9.25 | 24.04 |
| C11.8 HLAS | 13.55 | 5.42 | 5.42 | 14.10 |
| MEA | 6.91 | 2.76 | 2.76 | 7.20 |
| N67HSAS | 3.66 | 1.46 | 1.46 | 3.80 |
| Glycerol | 2.97 | 1.19 | 1.19 | 3.09 |
| PE-20, Polyethyleneimine Ethoxylate, PEI 600 E20 | 2.81 | 1.12 | 1.12 | 3.92 |
| Ethoxylated/Propoxylated Polyethyleneimine | 2.81 | 1.12 | 1.12 | 2.92 |
| Brightener 15 | 0.25 | 0.15 | 0.15 | 0.26 |
| Amine Oxide | 1.26 | 0.50 | 0.50 | 1.32 |
| Sasol 24,9 Nonionic Surfactant | 2.17 | 0.87 | 0.87 | 2.26 |
| DTPA (Chelant) | 1.01 | 0.40 | 0.40 | 1.06 |
| Tiron (Chelant) | 1.01 | 0.40 | 0.40 | 1.05 |
| Suds Suppressor AC8016 | 0.06 | 0.03 | 0.03 | 0.07 |
| Celvol 523 PVOH[1] | 0.00 | 13.80 | 13.80 | 32.92 |
| Water | 38.46 | 61.51 | | Trace |

[1]Celvol 523, Celanese/Sekisui, MW 85,000-124,000, 87-89% hydrolyzed

EXAMPLE 8

Table 8 below sets forth another example of a filament-forming composition of the present invention for making filaments and/or a nonwoven web of the present invention suitable for use as a laundry detergent.

TABLE 8

| | % by weight of filament-forming composition (i.e., premix) | Filament-Forming Composition (%) | Filament (i.e., components remaining upon drying) (%) | % by weight on a dry filament basis |
|---|---|---|---|---|
| C12-15 AES | 23.13 | 9.25 | 9.25 | 24.04 |
| C11.8 HLAS | 13.55 | 5.42 | 5.42 | 14.10 |
| MEA | 6.91 | 2.76 | 2.76 | 7.20 |
| N67HSAS | 3.66 | 1.46 | 1.46 | 3.80 |
| Glycerol | 2.97 | 1.19 | 1.19 | 3.09 |
| PE-20, Polyethyleneimine Ethoxylate, PEI 600 E20 | 2.81 | 1.12 | 1.12 | 3.92 |
| Ethoxylated/Propoxylated Polyethyleneimine | 2.81 | 1.12 | 1.12 | 2.92 |
| Brightener 15 | 0.25 | 0.15 | 0.15 | 0.26 |
| Amine Oxide | 1.26 | 0.50 | 0.50 | 1.32 |
| Sasol 24,9 Nonionic Surfactant | 2.17 | 0.87 | 0.87 | 2.26 |
| DTPA (Chelant) | 2.02 | 0.80 | 0.80 | 2.12 |
| Suds Suppressor AC8016 | 0.06 | 0.03 | 0.03 | 0.07 |
| Celvol 523 PVOH[1] | 0.00 | 13.80 | 13.80 | 32.92 |
| Water | 38.46 | 61.51 | | Trace |

[1]Celvol 523, Celanese/Sekisui, MW 85,000-124,000, 87-89% hydrolyzed

EXAMPLE 9

Table 9 below sets forth another example of a filament-forming composition of the present invention for making filaments and/or a nonwoven web of the present invention suitable for use as a laundry detergent.

TABLE 9

| | % by weight of filament-forming composition (i.e., premix) | Filament-Forming Composition (%) | Filament (i.e., components remaining upon drying) (%) | % by weight on a dry filament basis |
|---|---|---|---|---|
| C12-15 AES | 32.77 | 13.11 | 13.11 | 26.93 |
| C11.8 HLAS | 19.20 | 7.68 | 7.68 | 15.81 |
| Sodium Hydroxide | 7.70 | 3.08 | 3.08 | 6.34 |
| N67HSAS | 5.19 | 2.08 | 2.08 | 4.27 |
| PE-20, Polyethyleneimine Ethoxylate, PEI 600 E20 | 3.98 | 1.59 | 1.59 | 3.27 |
| Ethoxylated/Propoxylated Polyethyleneimine | 3.98 | 1.59 | 1.59 | 3.27 |
| Brightener 15 | 0.36 | 0.21 | 0.21 | 0.44 |
| Amine Oxide | 1.79 | 0.71 | 0.71 | 1.47 |
| Sasol 24,9 Nonionic Surfactant | 3.08 | 1.23 | 1.23 | 2.53 |
| DTPA (Chelant) | 2.87 | 1.15 | 1.15 | 2.38 |
| C12-18 Fatty Acid | 2.51 | 1.00 | 1.00 | 2.07 |
| 1,2-Propanediol | 2.96 | 1.18 | 1.18 | 2.44 |
| Ethanol | 0.34 | 0.14 | 0.14 | 0.28* |
| Suds Suppressor AC8016 | 0.09 | 0.03 | 0.03 | 0.07 |
| Celvol 523 PVOH[1] | 0.00 | 13.80 | 13.80 | 28.41 |
| Water | 17.16 | 51.42 | | Trace |

[1]Celvol 523, Celanese/Sekisui, MW 85,000-124,000, 87-89% hydrolyzed
*Calculated

EXAMPLE 10

Tables 10A-10F set forth another example of a filament-forming composition according to the present invention and the components thereof as well as the final composition of the filaments and/or nonwoven made therefrom. Such filaments and/or nonwoven web are suitable for use as a laundry detergent.

Laundry Detergent Premix

TABLE 10A

| Material | Activity (%) | Parts (%) | Parts (%) | Water (%) |
|---|---|---|---|---|
| MEA:AES | 100% | 29.35 | 29.35 | 0.00 |
| C16-17 AS-MEA | 100% | 4.71 | 4.71 | 0.00 |
| Sasol 24,9 Nonionic Surfactant | 100% | 1.27 | 1.27 | 0.00 |
| Glycerol | 100% | 3.24 | 3.24 | 0.00 |
| Brightener 15 | 51% | 2.26 | 4.46 | 2.20 |
| DTPA (Chelant) | 50% | 2.20 | 4.41 | 2.20 |
| MEA | 100% | 1.79 | 1.79 | 0.00 |
| C11.8 HLAS | 100% | 15.22 | 15.22 | 0.00 |
| PE-20, Polyethyleneimine Ethoxylate, PEI 600 E20 | 80% | 3.06 | 3.82 | 0.76 |
| Ethoxylated/Propoxylated Polyethyleneimine | 100% | 3.06 | 3.06 | 0.00 |
| Amine Oxide | 32% | 1.38 | 4.30 | 2.93 |
| AF8017 Antifoam (Suds Suppressor) | 100% | 0.06 | 0.06 | 0.00 |
| Water | | | 24.30 | 24.30 |
| | | 67.60 | 100.00 | 32.40 |

Polyvinyl Alcohol (PVOH) Premix

TABLE 10B

| Material | Activity (%) | Parts (%) | Parts (%) | Water (%) |
|---|---|---|---|---|
| Polyvinyl alcohol (Celvol 523) | 100% | 23.00 | 23.00 | 0.00 |
| Water | | | 77.00 | 77.00 |
| | | 23.00 | 100.00 | 77.00 |

Brightener 15 Premix

TABLE 10C

| Composition | % in Premix | Parts delivery | Active Basis |
|---|---|---|---|
| Brightener 15 Powder | 6.17 | 0.28% | 12.19% |
| % Nonionic Surfactant, Sasol 23,9 | 24.69 | 1.10% | 48.78% |
| % MEA | 19.75 | 0.88% | 39.02% |
| total | 50.61 | 2.26% | 100.00% |
| Water | 49.39 | 2.20% | |
| | 100.00 | 4.46% | |

Filament-Forming Composition Spun into Filaments

TABLE 10D

| Material | Activity (%) | Parts (%) | Parts (%) | Water (%) |
|---|---|---|---|---|
| PVOH Premix | 23.0% | 34.11 | 148.32 | 114.21 |
| Laundry Detergent Premix | 67.6% | 58.89 | 87.11 | 28.22 |
| | | 93.00 | 235.43 | 142.43 |
| Water Dried Off | | 0.00 | (135.43) | (135.43) |
| | | 93.00 | 100.00 | 7.00 |

Perfume Composition Added (after Formation) to
Filaments/Nonwoven Web Incorporating Filaments

TABLE 10E

| Material | Activity (%) | Parts (%) | Parts (%) | Water (%) |
|---|---|---|---|---|
| Nonwoven Web | 93% | 92.10 | 99.03 | 6.93 |
| Perfume | 100% | 0.97 | 0.97 | 0.00 |
|  |  | 93.07 | 100.00 |  |

Final Composition of Filaments/Nonwoven Web
Incorporating Filaments

TABLE 10F

| Material | Activity (%) | Parts (%) | Parts (%) | Water (%) |
|---|---|---|---|---|
| MEA:AES | 100% | 25.32 | 25.32 | 0.00 |
| C16-17 AS-MEA | 100% | 4.07 | 4.07 | 0.00 |
| Sasol 24,9 Nonionic Surfactant | 100% | 2.04 | 2.04 | 0.00 |
| Glycerol | 100% | 2.79 | 2.79 | 0.00 |
| Brightener 15 | 100% | 0.24 | 0.24 | 0.00 |
| DTPA (Chelant) | 100% | 1.90 | 1.90 | 0.00 |
| MEA | 100% | 2.31 | 2.31 | 0.00 |
| C11.8 HLAS | 100% | 13.13 | 13.13 | 0.00 |
| PE-20, Polyethyleneimine Ethoxylate, PEI 600 E20 | 100% | 2.64 | 2.64 | 0.00 |
| Ethoxylated/Propoxylated Polyethyleneimine | 100% | 2.64 | 2.64 | 0.00 |
| Amine Oxide | 100% | 1.19 | 1.19 | 0.00 |
| AF8017 Antifoam (Suds Suppressor) | 100% | 0.05 | 0.05 | 0.00 |
| Celvol 523 | 100% | 33.78 | 33.78 | 0.00 |
| Perfume | 100% | 0.97 | 0.97 | 0.00 |
| Water |  |  | 6.93 | 6.93 |
| Total |  | 93.07 | 100.00 | 6.93 |

EXAMPLE 11

Table 11A sets forth an example of an enzyme composition; namely an enzyme prill, that can be added to a filament and/or nonwoven web comprising filaments of the present invention. Table 11B sets for an example of a nonwoven web according to the present invention comprising the enzyme prill of Table 11A.

TABLE 11A

| Enzyme Composition | Weight (g) |
|---|---|
| Protease enzyme | 0.0065 |
| First Amylase enzyme | 0.0065 |
| Second Amylase enzyme | 0.0126 |
| Mannanase enzyme | 0.0331 |

TABLE 11B

| Enzyme Composition | Weight (g) | Weight (%) |
|---|---|---|
| Nonwoven web | 6.20 | 99.06 |
| Protease enzyme | 0.0065 | 0.10 |
| First Amylase enzyme | 0.0065 | 0.10 |
| Second Amylase enzyme | 0.0126 | 0.20 |
| Mannanase enzyme | 0.0331 | 0.53 |
| TOTAL | 6.26 | 100 |

EXAMPLE 12

Table 12 sets forth an example of a nonwoven web according to the present invention comprising a ellulose enzyme that is added to the nonwoven web or one or more filaments making up the nonwoven web after the filaments and/or nonwoven web are formed.

TABLE 12

| Enzyme Composition | Weight (g) | Weight (%) |
|---|---|---|
| Nonwoven web | 6.20 | 99.9 |
| Cellulase enzyme | 0.0062 | 0.1 |
| TOTAL | 6.2062 | 100 |

Test Methods

Unless otherwise indicated, all tests described herein including those described under the Definitions section and the following test methods are conducted on samples that have been conditioned in a conditioned room at a temperature of 73° F.±4° F. (about 23° C.±2.2° C.) and a relative humidity of 50%±10% for 2 hours prior to the test unless otherwise indicated. Samples conditioned as described herein are considered dry samples (such as "dry filaments") for purposes of this invention. Further, all tests are conducted in such conditioned room.

Water Content Test Method

The water (moisture) content present in a filament and/or fiber and/or nonwoven web is measured using the following Water Content Test Method.

A filament and/or nonwoven or portion thereof ("sample") is placed in a conditioned room at a temperature of 73° F.±4° F. (about 23° C.±2.2° C.) and a relative humidity of 50%±10% for at least 24 hours prior to testing. The weight of the sample is recorded when no further weight change is detected for at least a 5 minute period. Record this weight as the "equilibrium weight" of the sample. Next, place the sample in a drying oven for 24 hours at 70° C. with a relative humidity of about 4% to dry the sample. After the 24 hours of drying, immediately weigh the sample. Record this weight as the "dry weight" of the sample. The water (moisture) content of the sample is calculated as follows:

$$\% \text{ Water (moisture) in sample} = 100\% \times \frac{\text{(Equilibrium weight of sample} - \text{Dry weight of sample)}}{\text{Dry weight of sample}}$$

The % Water (moisture) in sample for 3 replicates is averaged to give the reported % Water (moisture) in sample.

Dissolution Test Method

Apparatus and Materials:
600 mL Beaker
Magnetic Stirrer (Labline Model No. 1250 or equivalent)
Magnetic Stirring Rod (5 cm)
Thermometer (1 to 100° C.+/−1° C.)
Template, Stainless Steel (3.8 cm×3.2 cm)
Timer (0-300 seconds, accurate to the nearest second)
35 mm Slide Mount having an open area of 3.8 cm×3.2 cm (commercially available from Polaroid Corporation)
35 mm Slide Mount Holder
City of Cincinnati Water or equivalent having the following properties: Total Hardness=155 mg/L as $CaCO_3$; Calcium content=33.2 mg/L; Magnesium content=17.5 mg/L; Phosphate content=0.0462

Sample Preparation:
1. Cut 3 test samples from a film or a nonwoven web to be tested ("sample") using the template to ensure that the sample fits within the 35 mm slide mount with open area dimensions 24×36 mm (i.e. 3.8 cm×3.2 cm specimen). Cut the samples from areas of the film or nonwoven web equally spaced along the transverse direction of the film or nonwoven web.
2. Lock each of the 3 samples in a separate 35 mm slide mount.
3. Place magnetic stirring rod into the 600 mL Beaker.
4. Obtain 500 mL or greater of Cincinnati city water and measure water temperature with thermometer and, if necessary, adjust the temperature of the water to maintain it at the testing temperature; namely, 5° C. Once the water temperature is at 5° C., fill the 600 mL beaker with 500 mL of the water.
5. Next, place the beaker on the magnetic stirrer. Turn the stirrer on, and adjust stir speed until a vortex develops in the water and the bottom of the vortex is at the 400 mL mark on the 600 mL beaker.
6. Secure the 35 mm slide mount with sample locked therein in a holder designed to lower the 35 mm slide mount into the water in the beaker, for example an alligator clamp of a 35 mm slide mount holder designed to position the 35 mm slide mount into the water present in the 600 mL beaker. The 35 mm slide mount is held by the alligator clamp in the middle of one long end of the 35 mm slide mount such that the long ends of the 35 mm slide mount are parallel to the surface of the water present in the 600 mL beaker. This set up will position the film or nonwoven surface perpendicular to the flow of the water. A slightly modified example of an arrangement of a 35 mm slide mount and slide mount holder are shown in FIGS. 1-3 of U.S. Pat. No. 6,787,512.
7. In one motion, the 35 mm slide mount holder, which positions the 35 mm slide mount above the center of the water in the beaker, is dropped resulting in the 35 mm slide mount becoming submerged in the water sufficiently such that the water contacts the entire exposed surface area of the film or nonwoven sample locked in the 35 mm slide mount. As soon as the water contacts the entire exposed surface area of the film or nonwoven start the timer. Disintegration occurs when the film or nonwoven breaks apart. When all of the visible film or nonwoven is released from the slide mount, raise the 35 mm slide mount out of the water while continuing to monitor the water for undissolved film or nonowoven fragments. Dissolution occurs when all film or nonwoven fragments are no longer visible in the water.
8. Three replicates of each sample are run.
9. Each disintegration and dissolution time is normalized by weight of the sample to obtain values of the disintegration and dissolution times per g of sample tested, which is in units of seconds/gram of sample (s/g). The average disintegration and dissolution times per g of sample tested of the three replicates are recorded.

Diameter Test Method

The diameter of a discrete filament or a filament within a nonwoven web or film is determined by using a Scanning Electron Microscope (SEM) or an Optical Microscope and an image analysis software. A magnification of 200 to 10,000 times is chosen such that the filaments are suitably enlarged for measurement. When using the SEM, the samples are sputtered with gold or a palladium compound to avoid electric charging and vibrations of the filament in the electron beam. A manual procedure for determining the filament diameters is used from the image (on monitor screen) taken with the SEM or the optical microscope. Using a mouse and a cursor tool, the edge of a randomly selected filament is sought and then measured across its width (i.e., perpendicular to filament direction at that point) to the other edge of the filament. A scaled and calibrated image analysis tool provides the scaling to get actual reading in µm. For filaments within a nonwoven web or film, several filament are randomly selected across the sample of the nonwoven web or film using the SEM or the optical microscope. At least two portions the nonwoven web or film (or web inside a product) are cut and tested in this manner. Altogether at least 100 such measurements are made and then all data are recorded for statistical analysis. The recorded data are used to calculate average (mean) of the filament diameters, standard deviation of the filament diameters, and median of the filament diameters.

Another useful statistic is the calculation of the amount of the population of filaments that is below a certain upper limit. To determine this statistic, the software is programmed to count how many results of the filament diameters are below an upper limit and that count (divided by total number of data and multiplied by 100%) is reported in percent as percent below the upper limit, such as percent below 1 micrometer diameter or %-submicron, for example. We denote the measured diameter (in µm) of an individual circular filament as di.

In case the filaments have non-circular cross-sections, the measurement of the filament diameter is determined as and set equal to the hydraulic diameter which is four times the cross-sectional area of the filament divided by the perimeter of the cross-section of the filament (outer perimeter in case of hollow filaments). The number-average diameter, alternatively average diameter is calculated as:

$$d_{num} = \frac{\sum_{i=1}^{n} d_i}{n}$$

Thickness Method

Thickness of a nonwoven web or film is measured by cutting 5 samples of a nonwoven web or film sample such that each cut sample is larger in size than a load foot loading surface of a VIR Electronic Thickness Tester Model II available from Thwing-Albert Instrument Company, Philadelphia, Pa. Typically, the load foot loading surface has a circular surface area of about 3.14 in². The sample is confined between a horizontal flat surface and the load foot loading surface. The load foot loading surface applies a confining pressure to the sample of 15.5 g/cm². The caliper of each sample is the resulting gap between the flat surface and the load foot loading surface. The caliper is calculated as the average caliper of the five samples. The result is reported in millimeters (mm).

Shear Viscosity Test Method

The shear viscosity of a filament-forming composition of the present invention is measured using a capillary rheometer, Goettfert Rheograph 6000, manufactured by Goettfert USA of Rock Hill S.C., USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A preheated to die test temperature, 60 g sample of the filament-forming composition is loaded into the barrel section of the rheometer. Rid the sample of any entrapped air. Push the sample from the barrel through the capillary die at a set of chosen rates 1,000-10,000 seconds$^{-1}$. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta = K\gamma^{n-1}$, wherein K is the material's viscosity constant, n is the material's thinning index and $\gamma$ is the shear rate. The reported apparent shear viscosity of the filament-forming composition herein is calculated from an interpolation to a shear rate of 3,000 sec$^{-1}$ using the power law relation.

Basis Weight Test Method

Basis weight of a fibrous structure sample is measured by selecting twelve (12) individual fibrous structure samples and making two stacks of six individual samples each. If the individual samples are connected to one another vie perforation lines, the perforation lines must be aligned on the same side when stacking the individual samples. A precision cutter is used to cut each stack into exactly 3.5 in.×3.5 in. squares. The two stacks of cut squares are combined to make a basis weight pad of twelve squares thick. The basis weight pad is then weighed on a top loading balance with a minimum resolution of 0.01 g. The top loading balance must be protected from air drafts and other disturbances using a draft shield. Weights are recorded when the readings on the top loading balance become constant. The Basis Weight is calculated as follows:

$$\text{Basis Weight (lbs/3000 ft}^2\text{)} = \frac{\text{Weight of basis weight pad (g)} \times 3000 \text{ ft}^2}{453.6 \text{ g/lbs} \times 12 \text{ samples} \times [12.25 \text{ in}^2 \text{ (Area of basis weight pad)}/144 \text{ in}^2]}$$

$$\text{Basis Weight (g/m}^2\text{)} = \frac{\text{Weight of basis weight pad (g)} \times 10{,}000 \text{ cm}^2/\text{m}^2}{79.0321 \text{ cm}^2 \text{ (Area of basis weight pad)} \times 12 \text{ samples}}$$

Weight Average Molecular Weight

The weight average molecular weight (Mw) of a material, such as a polymer, is determined by Gel Permeation Chromatography (GPC) using a mixed bed column. A high performance liquid chromatograph (HPLC) having the following components: Millenium®, Model 600E pump, system controller and controller software Version 3.2, Model 717 Plus autosampler and CHM-009246 column heater, all manufactured by Waters Corporation of Milford, Mass., USA, is utilized. The column is a PL gel 20 μm Mixed A column (gel molecular weight ranges from 1,000 g/mol to 40,000,000 g/mol) having a length of 600 mm and an internal diameter of 7.5 mm and the guard column is a PL gel 20 μm, 50 mm length, 7.5 mm ID. The column temperature is 55° C. and the injection volume is 200 μL. The detector is a DAWN® Enhanced Optical System (EOS) including Astra® software, Version 4.73.04 detector software, manufactured by Wyatt Technology of Santa Barbara, Calif., USA, laser-light scattering detector with K5 cell and 690 nm laser. Gain on odd numbered detectors set at 101. Gain on even numbered detectors set to 20.9. Wyatt Technology's Optilab® differential refractometer set at 50° C. Gain set at 10. The mobile phase is HPLC grade dimethylsulfoxide with 0.1% w/v LiBr and the mobile phase flow rate is 1 mL/min, isocratic. The run time is 30 minutes.

A sample is prepared by dissolving the material in the mobile phase at nominally 3 mg of material/1 mL of mobile phase. The sample is capped and then stirred for about 5 minutes using a magnetic stirrer. The sample is then placed in an 85° C. convection oven for 60 minutes. The sample is then allowed to cool undisturbed to room temperature. The sample is then filtered through a 5 μm Nylon membrane, type Spartan-25, manufactured by Schleicher & Schuell, of Keene, N.H., USA, into a 5 milliliter (mL) autosampler vial using a 5 mL syringe.

For each series of samples measured (3 or more samples of a material), a blank sample of solvent is injected onto the column. Then a check sample is prepared in a manner similar to that related to the samples described above. The check sample comprises 2 mg/mL of pullulan (Polymer Laboratories) having a weight average molecular weight of 47,300 g/mol. The check sample is analyzed prior to analyzing each set of samples. Tests on the blank sample, check sample, and material test samples are run in duplicate. The final run is a run of the blank sample. The light scattering detector and differential refractometer is run in accordance with the "Dawn EOS Light Scattering Instrument Hardware Manual" and "Optilab® DSP Interferometric Refractometer Hardware Manual," both manufactured by Wyatt Technology Corp., of Santa Barbara, Calif., USA, and both incorporated herein by reference.

The weight average molecular weight of the sample is calculated using the detector software. A do/dc (differential change of refractive index with concentration) value of 0.066 is used. The baselines for laser light detectors and the refractive index detector are corrected to remove the contributions from the detector dark current and solvent scattering. If a laser light detector signal is saturated or shows excessive noise, it is not used in the calculation of the molecular mass. The regions for the molecular weight characterization are selected such that both the signals for the 90° detector for the laser-light scattering and refractive index are greater than 3 times their respective baseline noise levels. Typically the high molecular weight side of the chromatogram is limited by the refractive index signal and the low molecular weight side is limited by the laser light signal.

The weight average molecular weight can be calculated using a "first order Zimm plot" as defined in the detector software. If the weight average molecular weight of the sample is greater than 1,000,000 g/mol, both the first and second order Zimm plots are calculated, and the result with the least error from a regression fit is used to calculate the molecular mass. The reported weight average molecular weight is the average of the two runs of the material test sample.

Filament Composition Test Method

In order to prepare filaments for filament composition measurement, the filaments must be conditioned by removing any coating compositions and/or materials present on the external surfaces of the filaments that are removable. An example of a method for doing so is washing the filaments 3 times with distilled water. The filaments are then air dried at 73° F.±4° F. (about 23° C.±2.2° C.) until the filaments comprises less than 10% moisture. A chemical analysis of the conditioned filaments is then completed to determine the compositional make-up of the filaments with respect to the filament-forming materials and the active agents and the level of the filament-forming materials and active agents present in the filaments.

The compositional make-up of the filaments with respect to the filament-forming material and the active agents can also be determined by completing a cross-section analysis using TOF-SIMs or SEM. Still another method for determining compositional make-up of the filaments uses a fluorescent dye as a marker. In addition, as always, a manufacturer of filaments should know the compositions of their filaments.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples and/or embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for delivering one or more active agents to fabric articles or hard surfaces, the method comprising the steps:
    a. providing a nonwoven web comprising a plurality of inter-entangled filaments, wherein at least one of the filaments exhibits a diameter of greater than 1 µm and comprises a filament-forming composition comprising one or more water-soluble filament-forming materials comprising a hydroxyl polymer and one or more active agents that are releasable from the filament when the filament is exposed to conditions of intended use, wherein the total level of the one or more filament-forming materials present in the filament is less than 40% by weight on a dry filament basis and the total level of the one or more active agents present in the filament is greater than 60% by weight on a dry filament basis; wherein the one or more active agents are selected from the group consisting of fabric care active agents, dishwashing active agents, and hard surface active agents; with the proviso that when the active agent comprises an enzyme, the enzyme is present in an amount from about 0.001% to 5% by weight on a dry filament basis; and
    b. triggering the release of one or more of the active agents from the filament.

2. The method according to claim 1 wherein the triggering step comprises exposing the filament to moisture.

3. The method according to claim 1 wherein the triggering step comprises exposing the filament to a temperature of greater than 75° F.

4. The method according to claim 1 wherein the triggering step comprises the step of applying a force to the filament.

5. The method according to claim 4 wherein the step of applying a force to the filament comprises stretching the filament.

6. The method according to claim 1 wherein the triggering step comprises exposing the filament to a chemical reaction.

7. The method according to claim 1 wherein the triggering step results in the filament losing its filament structure.

8. The method according to claim 7 wherein the filament loses its filament structure as a result of at least a part of the filament swelling.

9. The method according to claim 7 wherein the filament loses its filament structure as a result of at least a part of the filament shrinking.

10. The method according to claim 1 wherein the active agent is a fabric care active agent.

11. The method according to claim 1 wherein the step of triggering comprises one or more steps selected from the group consisting of:
    a. pre-treating stains on a fabric article with the nonwoven web;
    b. forming a wash liquor by contacting the nonwoven web with water;
    c. tumbling the nonwoven web in a dryer;
    d. heating the nonwoven web in a dryer; and
    e. combinations thereof.

12. A method for delivering one or more active agents to fabric articles or hard surfaces, the method comprising the steps:
    a. providing a nonwoven web comprising a plurality of inter-entangled filaments, wherein at least one of the filaments exhibits a diameter of greater than 1 µm and comprises a filament-forming composition comprising one or more water-soluble filament-forming materials comprising a hydroxyl polymer and one or more active agents that are releasable from the filament as the filament's morphology changes, wherein the total level of the one or more filament-forming materials present in the filament is less than 40% by weight on a dry filament basis and the total level of the one or more active agents present in the filament is greater than 60% by weight on a dry filament basis;

wherein the one or more active agents are selected from the group consisting of fabric care active agents, dishwashing active agents, and hard surface active agents; with the proviso that when the active agent comprises an enzyme, the enzyme is present in an amount from about 0.001% to 5% by weight on a dry filament basis; and b. triggering the release of one or more of the active agents from the filament.

13. The method according to claim 12 wherein the triggering step comprises exposing the filament to moisture.

14. The method according to claim 12 wherein the triggering step comprises exposing the filament to a temperature of greater than 75° F.

15. The method according to claim 12 wherein the triggering step comprises the step of applying a force to the filament.

16. The method according to claim 15 wherein the step of applying a force to the filament comprises stretching the filament.

17. The method according to claim 12 wherein the triggering step comprises exposing the filament to a chemical reaction.

18. The method according to claim 12 wherein the triggering step results in the filament losing its filament structure.

19. The method according to claim 18 wherein the filament loses its filament structure as a result of at least a part of the filament swelling.

20. The method according to claim 18 wherein the filament loses its filament structure as a result of at least a part of the filament shrinking.

21. The method according to claim 12 wherein the active agent is a fabric care active agent.

22. The method according to claim 12 wherein the step of triggering comprises one or more steps selected from the group consisting of:
   a. pre-treating stains on a fabric article with the nonwoven web;
   b. forming a wash liquor by contacting the nonwoven web with water;
   c. tumbling the nonwoven web in a dryer;
   d. heating the nonwoven web in a dryer; and
   e. combinations thereof.

* * * * *